US008680272B2

(12) United States Patent
Kamal et al.

(10) Patent No.: US 8,680,272 B2
(45) Date of Patent: Mar. 25, 2014

(54) 3-ARYLETHYNYL SUBSTITUTED QUINAZOLINONE COMPOUNDS

(75) Inventors: Ahmed Kamal, Hyderabad (IN); Farheen Sultana, Hyderabad (IN); Erla Vijaya Bharathi, Hyderabad (IN); Yellamelli Valli Venkata Srikanth, Hyderabad (IN); Arutla Viswanath, Hyderabad (IN); Ponnampalli Swapna, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/984,218

(22) PCT Filed: Mar. 31, 2011

(86) PCT No.: PCT/IN2011/000228
§ 371 (c)(1),
(2), (4) Date: Aug. 7, 2013

(87) PCT Pub. No.: WO2012/111017
PCT Pub. Date: Aug. 23, 2012

(65) Prior Publication Data
US 2013/0317221 A1 Nov. 28, 2013

(30) Foreign Application Priority Data
Feb. 15, 2011 (IN) .............................. 391/DEL/2011

(51) Int. Cl.
C07D 401/00 (2006.01)
(52) U.S. Cl.
USPC ....................................................... 544/284
(58) Field of Classification Search
None
See application file for complete search history.

(56) References Cited

FOREIGN PATENT DOCUMENTS

WO WO-9833802 A1 8/1998
WO WO-0248117 A1 6/2002

OTHER PUBLICATIONS

A. Lord et al. "Design, Synthesis and Evaluation in Vitro of Quinoline-8-carboxamides, a New Class of Poly(adenosine-diphosphate-ribose)polymerase-1 (PARP-1) Inhibitor," J. Med. Chem, 52, 868-877 (2009).
J. Liu et al. "Design and Synthesis of a Quinazolinone Natural Product-Templated Library with Cytotoxic Activity," J. Comb. Chem, 8, 7-10, (2006).
D. Raffa et al. "Synthesis, cytoxicity, and inhibitory effects on tubulin polymerization of a new 3-heterocyclo substituted 2-styrylquinazolinones," European Journal of Medicinal Chemistry 39, 299-304, (2004).
J. Jiang et al. "Synthesis and Biological Evaluation of 2-styrylquinazolin-4(3H)-ones, a New Class of Antimitotic Anticancer Agents Which Inhibit Tubulin Polymerization," J. Med. Chem. 33, 1721-1728, (1990).
International Search Report and Written Opinion issued in PCT/IN2011/000228, 2011.

Primary Examiner — Sun Jae Loewe
(74) Attorney, Agent, or Firm — Edwards Wildman Palmer LLP; Barry Kramer; Nicholas J. DiCeglie, Jr.

(57) ABSTRACT

The present invention provides 3-arylethynyl substituted quinazolinone compounds of formula (A) as potential anticancer agents against sixty human cancer cell lines. $R_1$=H, OH, $OCH_3$; $R_2$=H, OH, $CH_3$, $OCH_3$, $NO_2$; $R_3$=H, OH, $OCH_3$, F, Cl; $R_2+R_3$=—$OCH_2O$—; $R_4$=H, OH, $CH_3$, $OCH_3$; $R^5$=H, OH, $CH_3$, $OCH_3$; $R^6$=H, $OCH_3$.

8 Claims, 2 Drawing Sheets

Scheme 1. *Reagents and conditions*: (i) Substituted phenyl acetylenes, Pd(PPh$_3$)$_4$, CuI, BuNH$_2$, ether, rt, 6h; (ii) Ac$_2$O, 150 °C, 30 min; (iii) Amino acetylenes, AcOH, reflux, 8h (iv) Substituted aldehydes, AcOH, reflux, 8h.

3-ARYLETHYNYL SUBSTITUTED QUINAZOLINONE COMPOUNDS

CROSS REFERENCE TO RELATED APPLICATIONS

This application is a 371 U.S. National Phase Application of PCT/IN2011/000228, filed Mar. 31, 2011, which claims priority to Indian Patent Application No. 391/DEL/2011, filed Feb. 15, 2011, the disclosures of each of which are expressly incorporated herein by reference in their entireties.

FIELD OF THE INVENTION

The present invention relates to 3-Arylethynyl substituted quinazolinone compounds of general formula A as potential anticancer agents and a process for the preparation thereof.

General formula A

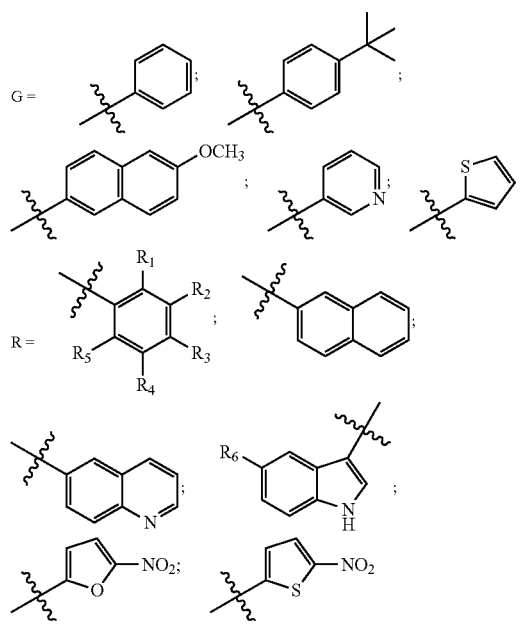

Wherein,

G =

R =

$R_1$ = H, OH, $OCH_3$
$R_2$ = H, OH, $CH_3$, $OCH_3$, $NO_2$
$R_3$ = H, OH, $OCH_3$, F, Cl
$R_2 + R_3$ = —$OCH_2O$—
$R_4$ = H, OH, $CH_3$, $OCH_3$
$R_5$ = H, OH, $CH_3$, $OCH_3$,
$R_6$ = H, $OCH_3$,

The structural formula of the representative compounds of 3-Arylethynyl substituted quinazolinone compounds of general formula A are:

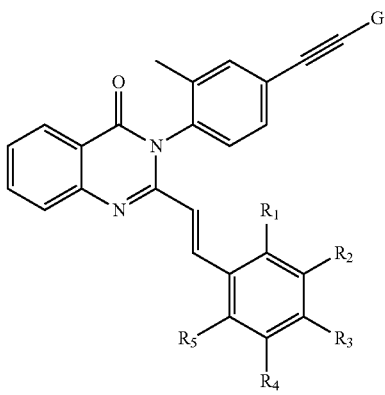

G =

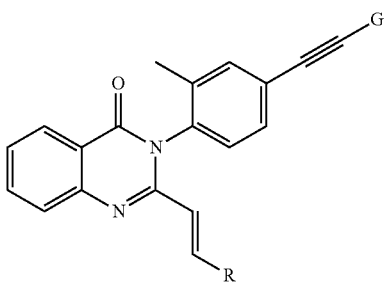

$R_1$ = H, OH, $OCH_3$
$R_2$ = H, OH, $CH_3$, $OCH_3$, $NO_2$
$R_3$ = H, OH, $OCH_3$, F, Cl
$R_2 + R_3$ = —$OCH_2O$— For compounds 4j, 5j, 6j, 7j, 8j
$R_4$ = H, OH, $CH_3$, $OCH_3$
$R_5$ = H, OH, $CH_3$, $OCH_3$, Formula 4a-n to 8a-n

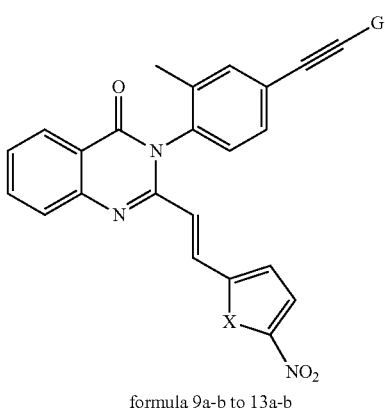

formula 9a-b to 13a-b

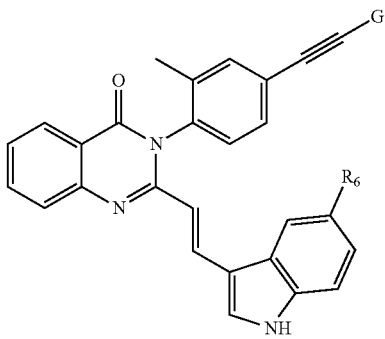

formula 14a-b to 18a-b

-continued

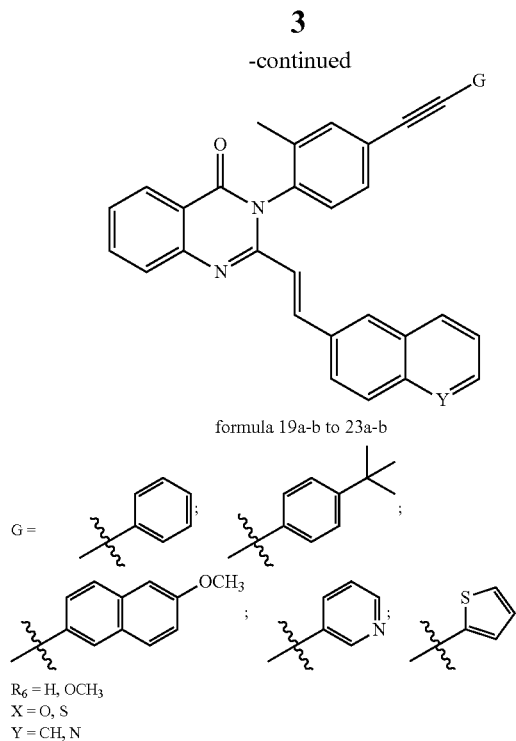

formula 19a-b to 23a-b $R_6$ = H, OCH$_3$
X = O, S
Y = CH, N

BACKGROUND OF THE INVENTION

Poly(ADP-ribose)polymerase-1 (PARP-1) a nuclear enzyme bounded to chromatin involved in a variety of physiological functions related to genomic repair, including DNA replication and repair, cellular proliferation and differentiation, and apoptosis. Inhibition of these PARP enzyme results in genomic dysfunction and finally leading to cell death (Ferraris, D. V. *J. Med. Chem.* 2010, 53, 4561).

Quinazolinone (1) is a naturally occurring alkaloid as well as a core structural subunit in a growing class of bioactive natural products and synthetic compounds (Michael, J. P. *Nat. Prod. Rep.* 2004, 21, 650" and also D'yakonov, A. L.; Telezhenetskaya, M. V. *Chem. Nat. Comput.* 1997, 33, 221). Recently various quinazolinone compounds were identified as dual inhibitors of P-glycoprotein (Pgp) and the multidrug resistance associated protein (MRP1). These proteins cause resistance in tumor cells hence inhibition of these proteins were useful in cancer chemotherapy (Wang, S.; Ryder, H.; Pretswell, I.; Depledge, P.; Milton, J.; Hancox, T. C.; Dale, I.; Dangerfield, W.; Charlton, P.; Faint, R.; Dodda, R.; Hassan, S. *Bioorg. Med. Chem. Lett.* 2002, 12, 571). Recently a library of quinazollinone compounds containing 2-styryl quinazolinone compounds possessing a defining structural feature, containing 3-substituted aliphatic chain bearing basic nitrogen, exhibiting cytotoxicity against various cancer cell lines. (Liu, J. F.; Kaselj, M.; Isome, Y.; Ye, P.; Sargent, K.; Sprague, K.; Chemak, D.; Wilson, C. J.; Si, Y.; Yohannes, D.; Ng, S. C. *J Comb Chem.* 2006, 8, 7-10). Various substituted 2-phenyl-4-quinazolinones and 2,3-dihydro-2-phenyl-4-quinazolinones displayed highly selective cytotoxicity against the ovarian cancer 1A9 and P-gp resistant KB-VIN cell lines and these compounds acts as tubulin polymerization inhibitiors. (Hour, M. J.; Huang, L. J.; Kuo, S. C.; Xia, Y.; Bastow, K.; Nakanishi, Y.; Hamel, E.; Lee, K. H. *J. Med. Chem.* 2000, 43, 4479). Moreover a new class of 4(3H)-quinazolinones 2-styryl substituted derivatives (2) form an important component of pharmacologically active compounds which exhibit anticancer activity by inhibition of tubulin polymerization. (Jiang, J. B.; Hesson, D. P.; Dusak, B. A.; Dexter, D. L.; Kang, G. J.; Hamel, E. *J. Med. Chem.* 1990, 33, 1721" and also Raffa, D.; Edler, M. C.; Daidone, G.; Maggio, B.; Merikech, M.; Plescia, S.; Schillaci, D.; Bai, R.; Hamel, E. *Eur. J. Med. Chem.* 2004, 39, 299). Whereas a novel series containing 2-methyl quinazolinones and 2-aryl quinazolinones act as inhibitors of DNA repair enzyme poly (ADP-ribose) polymerase. (Griffin, R. J.; Srinivasan, S.; Bowman, K.; Calvert, A. H.; Curtin, N. J.; Newell, D. R.; Pemberton, L. C.; Golding, B. T. *J. Med. Chem.* 1998, 41, 5247).

Recently a series of 3-aryl ethynyl substituted quinoline-8-carboxamide were synthesized and identified as a new class of PARP inhibitors. (Lord, A. M.; Mahon, M. F.; Lloyd, M. D.; Threadgill, M. D. J. Med. Chem. 2009, 52, 868-877) and also a new series of 3-ethynyl-1H-indazoles (3) has been synthesized and exhibited low micro molar inhibition against critical components of the PI3K pathway, targeting PI3K, PDK1, and mTOR kinases, These compound displays significant antiproliferative activity both in monolayer human cancer cell cultures and in three dimensional tumor models and these identified as multiple PI3K/PDK1/mTOR inhibitors. (Barile, E.; De, S. K.; Carlson, C. B.; Chen, V.; Knutzen, C.; Riel-Mehan, M.; Yang, L.; Dahl, R.; Chiang, G.; Pellecchia, M.). More recently structure-activity relationship study revealed the rigid triple bond functionality also contributed to the observed antiviral activity and also antiproliferative activity for ethynyltriazole ribonucleosides which are showing potent a poptosis-induced antiproliferative activity against pancreatic cancer MiaPaCa-2 cells both in vitro and in vivo The role of ethynyl group may be due to appended π-conjugated systems to offer helpful binding properties with the corresponding biological targets via the stronger interactions afforded by a larger aromatic binding surface and better shape complementary conjugated system. (Wan J, Xia Y, Liu Y, Wang M, Rocchi P, Yao J, Qu F, Neyts J, Iovanna J L, Peng L. *J. Med. Chem.* 2009, 52, 1144-1155).

Keeping this aspect in mind, various aryl ethynyl groups are incorporated at N-3 position of quinazolinones. Further structural modifications have also been carried out at position 2 of quinazolinone ring. Thereby, the newly designed and synthesized molecules comprising of quinazolinone and phenyl ethynyl moiety could possess promising anticancer activity that might work through inhibition of PARP. Additionally, these are structurally simple small molecules.

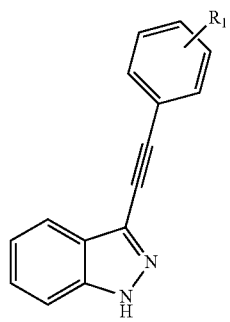

OBJECTIVES OF THE INVENTION

The main objective of the present invention is to provide 3-Arylethynyl substituted quinazolinone compounds of general formula A.

Another objective of the present invention is to provide process for the preparation of 3-Arylethynyl substituted quinazolinone compounds of general formula A.

Still another objective of the present invention is to provide 3-Arylethynyl substituted quinazolinone compounds of general formula A as potential anticancer agents.

SUMMARY OF THE INVENTION

Accordingly, present invention provides 3-Arylethynyl substituted quinazolinone compounds of general formula A General formula A Wherein,

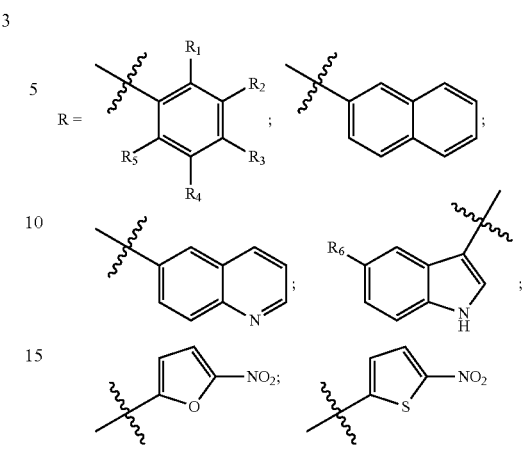

$R_1$ = H, OH, OCH$_3$
$R_2$ = H, OH, CH$_3$, OCH$_3$, NO$_2$
$R_3$ = H, OH, OCH$_3$, F, Cl
$R_2$ + $R_3$ = ——OCH$_2$O——
$R_4$ = H, OH, CH$_3$, OCH$_3$
$R_5$ = H, OH, CH$_3$, OCH$_3$
$R_6$ = H, OCH$_3$

In yet another embodiment of the present invention, structural formulas of the representative group of 3-Arylethynyl substituted quinazolinone compounds are:

Where G =

$R_1$ = H, OH, OCH$_3$
$R_2$ = H, OH, CH$_3$, OCH$_3$, NO$_2$
$R_3$ = H, OH, OCH$_3$, F, Cl
$R_2$ + $R_3$ = ——OCH$_2$O—— For compounds 4j, 5j, 6j, 7j, 8j
$R_4$ = H, OH, CH$_3$, OCH$_3$
$R_5$ = H, OH, CH$_3$, OCH$_3$, -continued Formula 4a-n to 8a-n

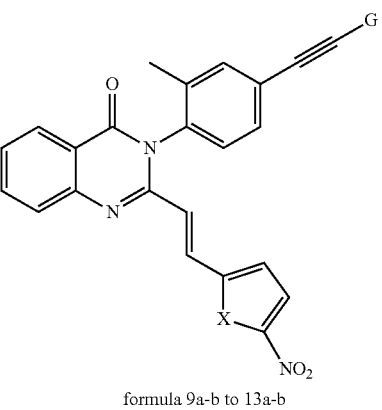

formula 9a-b to 13a-b

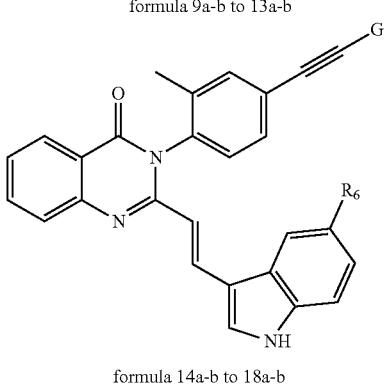

formula 14a-b to 18a-b

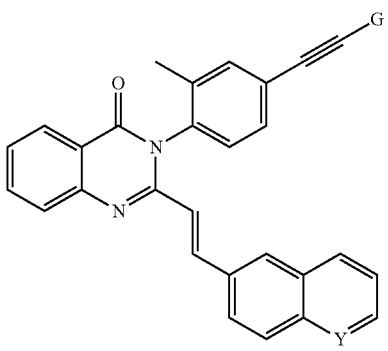

formula 19a-b to 23a-b

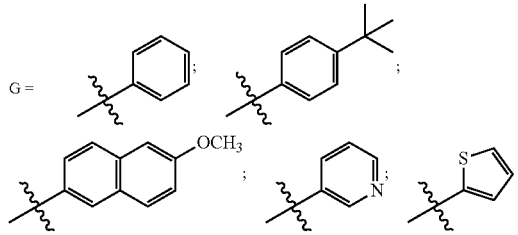

$R_6$ = H, OCH$_3$
X = O, S
Y = CH, N

In yet another embodiment of the present invention, said compounds are useful as anticancer agent. In yet another embodiment of the present invention, 3-Arylethynyl substituted quinazolinone compounds of general formula A, wherein chemical formula of the compounds are:

(E)-3-(2-Methyl-4-(phenylethynyl)phenyl)-2-(2-methylstyryl)quinazolin-4(3H)-one (4a);

(E)-2-(4-Hydroxystyryl)-3-(2-methyl-4-(phenylethynyl)phenyl)quinazolin-4(3H)-one (4b);

(E)-2-(2,5-Dihydroxystyryl)-3-(2-methyl-4-(phenylethynyl)phenyl)quinazolin-4(3H)-one (4c);

(E)-2-(2,4-Dihydroxystyryl)-3-(2-methyl-4-(phenylethynyl)phenyl)quinazolin-4(3H)-one (4d);

(E)-2-(4-Hydroxy-3-nitrostyryl)-3-(2-methyl-4-(phenylethynyl)phenyl)quinazolin-4(3H)-one (4e);

(E)-2-(4-Methoxystyryl)-3-(2-methyl-4-(phenylethynyl)phenyl)quinazolin-4(3H)-one (4f);

(E)-2-(4-Hydroxy-3-methoxystyryl)-3-(2-methyl-4-phenylethynyl)phenyl)quinazolin-4(3H)-one (4g)

(E)-2-(3,4-Dimethoxystyryl)-3-(2-methyl-4-(phenylethynyl)phenyl)quinazolin-4(3H)-one (4h);

(E)-2-(2,4-Dimethoxystyryl)-3-(2-methyl-4-(phenylethynyl)phenyl)quinazolin-4(3H)-one (4i);

(E)-2-(2-(Benzo[d][1,3]dioxol-5-yl)vinyl)-3-(2-methyl-4-(phenylethynyl)phenyl)quinazolin-4(3H)-one (4j);

(E)-2-(4-Hydroxy-3,5-dimethylstyryl)-3-(2-methyl-4-phenylethynyl)phenyl)quinazolin-4(3H)-one (4k);

(E)-3-(2-Methyl-4-(phenylethynyl)phenyl)-2-(3,4,5-trimethoxystyryl)quinazolin-4(3H)-one (4l);

(E)-2-(4-Fluorostyryl)-3-(2-methyl-4-(phenylethynyl)phenyl)quinazolin-4(3H)-one (4m);

(E)-2-(4-Chlorostyryl)-3-(2-methyl-4-(phenylethynyl)phenyl)quinazolin-4(3H)-one (4n);

(E)-3-(4-((4-Tert-butylphenyl)ethynyl)-2-methylphenyl)-2-(2-methylstyryl)quinazolin-4(3H)-one (5a);

(E)-3-(4-((4-Tert-butylphenyl)ethynyl)-2-methylphenyl)-2-(4-hydroxystyryl)quinazolin-4(3H)-one (5b);

(E)-3-(4-((4-Tert-butylphenyl)ethynyl)-2-methylphenyl)-2-(2,5-dihydroxystyryl)quinazolin-4(3H)-one (5c);

(E)-3-(4-((4-Tert-butylphenyl)ethynyl)phenyl)-2-(2,4-dihydroxystyryl)quinazolin-4(3H)-one (5d);

(E)-3-(4-((4-Tert-butylphenyl)ethynyl)-2-methylphenyl)-2-(4-hydroxy-3-nitrostyryl)quinazolin-4(3H)-one (5e);

(E)-3-(4-((4-Tert-butylphenyl)ethynyl)-2-methylphenyl)-2-(4-methoxystyryl)quinazolin-4(3H)-one (5f);

(E)-3-(4-((4-Tert-butylphenyl)ethynyl)-2-methylphenyl)-2-(4-hydroxy-3-methoxystyryl)quinazolin-4(3H)-one (5g);

(E)-3-(4-((4-Tert-butylphenyl)ethynyl)-2-methylphenyl)-2-(3,4-dimethoxystyryl)quinazolin-4(3H)-one (5h);

(E)-3-(4-((4-Tert-butylphenyl)ethynyl)-2-methylphenyl)-2-(2,4-dimethoxystyryl)quinazolin-4(3H)-one (5i);

(E)-2-(2-(Benzo[d][1,3]dioxol-5-yl)vinyl)-3-(4-((4-tert-butylphenyl)ethynyl)-2-methylphenyl)quinazolin-4(3H)-one (5j);

(E)-3-(4-((4-Tert-butylphenyl)ethynyl)-2-methylphenyl)-2-(4-hydroxy-3,5-dimethylstyryl)quinazolin-4(3H)-one (5k);

(E)-3-(4-((4-Tert-butylphenyl)ethynyl)-2-methylphenyl)-2-(3,4,5-trimethoxystyryl)quinazolin-4(3H)-one (5i);

(E)-3-(4-((4-Tert-butylphenyl)ethynyl)-2-methylphenyl)-2-(4-fluorostyryl)quinazolin-4(3H)-one (5m);

(E)-3-(4-((4-Tert-butylphenyl)ethynyl)-2-methylphenyl)-2-(4-chlorostyryl)quinazolin-4(3H)-one (5n);

(E)-3-(4-((6-Methoxynaphthalen-2-yl)ethynyl)-2-methylphenyl)-2-(2-methylstyryl)quinazolin-4(3H)-one (6a);

(E)-2-(4-Hydroxystyryl)-3-(4-((6-methoxynaphthalen-2-yl)ethynyl)-2-methylphenyl)quinazolin-4(3H)-one (6b);

(E)-2-(2,5-Dihydroxystyryl)-3-(4-((6-methoxynaphthalen-2-yl)ethynyl)-2-methylphenyl)quinazolin-4(3H)-one (6c);

(E)-2-(2,4-Dihydroxystyryl)-3-(4-((6-methoxynaphthalen-2-yl)ethynyl)-2-methylphenyl)quinazolin-4(3H)-one (6d);

(E)-2-(4-Hydroxy-3-nitrostyryl)-3-(4-((6-methoxynaphthalen-2-yl)ethynyl)-2-methylphenyl)quinazolin-4(3H)-one (6e);

(E)-2-(4-methoxystyryl)-3-(4-((6-methoxynaphthalen-2-yl)ethynyl)-2-methylphenyl)quinazolin-4(3H)-one (6f);

(E)-2-(4-Hydroxy-3-methoxystyryl)-3-(4-((6-methoxynaphthalen-2-yl)ethynyl)-2-methylphenyl)quinazolin-4(3H)-one (6g);

(E)-2-(3,4-Dimethoxystyryl)-3-(4-((6-methoxynaphthalen-2-yl)ethynyl)-2-methylphenyl)quinazolin-4(3H)-one (6h);

(E)-2-(2,4-Dimethoxystyryl)-3-(4-((6-methoxynaphthalen-2-yl)ethynyl)-2-methylphenyl)quinazolin-4(3H)-one (6i);

(E)-2-(2-(Benzo[d][1,3]dioxol-5-yl)vinyl)-3-(4-((6-methoxynaphthalen-2-yl)ethynyl)-2-methylphenyl)quinazolin-4(3H)-one (6j);

(E)-2-(4-Hydroxy-3,5-dimethylstyryl)-3-(4-((6-methoxynaphthalen-2-yl)ethynyl)-2-methylphenyl)quinazolin-4(3H)-one (6k);

(E)-3-(4-((6-Methoxynaphthalen-2-yl)ethynyl)-2-methylphenyl)-2-(3,4,5-trimethoxystyryl)quinazolin-4(3H)-one (6l);

(E)-2-(4-Fluorostyryl)-3-(4-((6-methoxynaphthalen-2-yl)ethynyl)-2-methylphenyl)quinazolin-4(3H)-one (6m);

(E)-2-(4-Chlorostyryl)-3-(4-((6-methoxynaphthalen-2-yl)ethynyl)-2-methylphenyl)quinazolin-4(3H)-one (6n);

(E)-3-(2-Methyl-4-(pyridin-3-ylethynyl)phenyl)-2-(2-methylstyryl)quinazolin-4(3H)-one (7a);

(E)-2-(4-Hydroxystyryl)-3-(2-methyl-4-(pyridin-3-ylethynyl)phenyl)quinazolin-4(3H)-one (7b);

(E)-2-(2,5-Dihydroxystyryl)-3-(2-methyl-4-(pyridin-3-ylethynyl)phenyl)quinazolin-4(3H)-one (7c);

(E)-2-(2,4-Dihydroxystyryl)-3-(2-methyl-4-(pyridin-3-ylethynyl)phenyl)quinazolin-4(3H)-one (7d);

(E)-2-(4-Hydroxy-3-nitrostyryl)-3-(2-methyl-4-(pyridin-3-ylethynyl)phenyl)quinazolin-4(3H)-one (7e);

(E)-2-(4-Methoxystyryl)-3-(2-methyl-4-(pyridin-3-ylethynyl)phenyl)quinazolin-4(3H)-one (7f);

(E)-2-(4-Hydroxy-3-methoxystyryl)-3-(2-methyl-4-(pyridin-3-ylethynyl)phenyl)quinazolin-4(3H)-one (7g);

(E)-2-(3,4-Dimethoxystyryl)-3-(2-methyl-4-(pyridin-3-ylethynyl)phenyl)quinazolin-4(3H)-one (7h);

(E)-2-(2,4-Dimethoxystyryl)-3-(2-methyl-4-(pyridin-3-ylethynyl)phenyl)quinazolin-4(3H)-one (7i);

(E)-2-(2-(Benzo[d][1,3]dioxol-5-yl)vinyl)-3-(2-methyl-4-(pyridin-3-ylethynyl)phenyl)quinazolin-4(3H)-one (7j);

(E)-2-(4-Hydroxy-3,5-dimethylstyryl)-3-(2-methyl-4-(pyridin-3-ylethynyl)phenyl)quinazolin-4(3H)-one (7k);

(E)-3-(2-Methyl-4-(pyridin-3-ylethynyl)phenyl)-2-(3,4,5-trimethoxystyryl)quinazolin-4(3H)-one (7l);

(E)-2-(4-Fluorostyryl)-3-(2-methyl-4-(pyridin-3-ylethynyl)phenyl)quinazolin-4(3H)-one (7m);

(E)-2-(4-Chlorostyryl)-3-(2-methyl-4-(pyridin-3-ylethynyl)phenyl)quinazolin-4(3H)-one (7n);

(E)-3-(2-Methyl-4-(thiophen-2-ylethynyl)phenyl)-2-(2-methylstyryl)quinazolin-4(3H)-one (8a);

(E)-2-(4-Hydroxystyryl)-3-(2-methyl-4-(thiophen-2-ylethynyl)phenyl)quinazolin-4(3H)-one (8b);

(E)-2-(2,5-Dihydroxystyryl)-3-(2-methyl-4-(thiophen-2-ylethynyl)phenyl)quinazolin-4(3H)-one (8c);

(E)-2-(2,4-Dihydroxystyryl)-3-(2-methyl-4-(thiophen-2-ylethynyl)phenyl)quinazolin-4(3H)-one (8d);

(E)-2-(4-Hydroxy-3-nitrostyryl)-3-(2-methyl-4-(thiophen-2-ylethynyl)phenyl)quinazolin-4(3H)-one (8e);

(E)-2-(4-Methoxystyryl)-3-(2-methyl-4-(thiophen-2-ylethynyl)phenyl)quinazolin-4(3H)-one (8f);

(E)-2-(4-Hydroxy-3-methoxystyryl)-3-(2-methyl-4-(thiophen-2-ylethynyl)phenyl)quinazolin-4(3H)-one (8g);

(E)-2-(3,4-Dimethoxystyryl)-3-(2-methyl-4-(thiophen-2-ylethynyl)phenyl)quinazolin-4(3H)-one (8h);

(E)-2-(2,4-Dimethoxystyryl)-3-(2-methyl-4-(thiophen-2-ylethynyl)phenyl)quinazolin-4(3H)-one (8i);

(E)-2-(2-(Benzo[d][1,3]dioxol-5-yl)vinyl)-3-(2-methyl-4-(thiophen-2-ylethynyl)phenyl)quinazolin-4(3H)-one (8j);

(E)-2-(4-Hydroxy-3,5-dimethylstyryl)-3-(2-methyl-4-(thiophen-2-ylethynyl)phenyl)quinazolin-4(3H)-one (8k);

(E)-3-(2-Methyl-4-(thiophen-2-ylethynyl)phenyl)-2-(3,4,5-trimethoxystyryl)quinazolin-4(3H)-one (8l);

(E)-2-(4-Fluorostyryl)-3-(2-methyl-4-(thiophen-2-ylethynyl)phenyl)quinazolin-4(3H)-one (8m);

(E)-2-(4-Chlorostyryl)-3-(2-methyl-4-(thiophen-2-ylethynyl)phenyl)quinazolin-4(3H)-one (8n);

(E)-3-(2-Methyl-4-(phenylethynyl)phenyl)-2-(2-(5-nitrofuran-2-yl)vinyl)quinazolin-4(3H)-one (9a);

(E)-3-(2-Methyl-4-(phenylethynyl)phenyl)-2-(2-(5-nitrothiophen-2-yl)vinyl)quinazolin-4(3H)-one (9b);

(E)-3-(4-((4-Tert-butylphenyl)ethynyl)-2-methylphenyl)-2-(2-(5-nitrofuran-2-yl)vinyl)quinazolin-4(3H)-one (10a);

(E)-3-(4-((4-Tert-butylphenyl)ethynyl)-2-methylphenyl)-2-(2-(5-nitrothiophen-2-yl)vinyl)quinazolin-4(3H)-one (10b);

(E)-3-(4-((6-Methoxynaphthalen-2-yl)ethynyl)-2-methylphenyl)-2-(2-(5-nitrofuran-2-yl)vinyl)quinazolin-4(3H)-one (11a);

(E)-3-(4-((6-Methoxynaphthalen-2-yl)ethynyl)-2-methylphenyl)-2-(2-(5-nitrothiophen-2-yl)vinyl)quinazolin-4(3H)-one (11b);

(E)-3-(2-Methyl-4-(pyridin-3-ylethynyl)phenyl)-2-(2-(5-nitrofuran-2-yl)vinyl)quinazolin-4(3H)-one (12a);

(E)-3-(2-Methyl-4-(pyridin-3-ylethynyl)phenyl)-2-(2-(5-nitrothiophen-2-yl)vinyl)quinazolin-4(3H)-one (12b);

(E)-3-(2-Methyl-4-(thiophen-2-ylethynyl)phenyl)-2-(2-(5-nitrofuran-2-yl)vinyl)quinazolin-4(3H)-one (13a);

(E)-3-(2-Methyl-4-(thiophen-2-ylethynyl)phenyl)-2-(2-(5-nitrothiophen-2-yl)vinyl)quinazolin-4(3H)-one (13b);

(E)-2-(2-(1H-Indol-3-yl)vinyl)-3-(2-methyl-4-(phenylethynyl)phenyl)quinazolin-4(3H)-one (14a);

(E)-2-(2-(5-Methoxy-1H-indol-3-yl)vinyl)-3-(2-methyl-4-(phenylethynyl)phenyl)quinazolin-4(3H)-one (14b);

(E)-2-(2-(1H-Indol-3-yl)vinyl)-3-(4-((4-tert-butylphenyl)ethynyl)-2-methylphenyl)quinazolin-4(3H)-one (15a);

(E)-3-(4-((4-Tert-butylphenyl)ethynyl)-2-methylphenyl)-2-(2-(5-methoxy-1H-indol-3-yl)vinyl)quinazolin-4(3H)-one (15b);

(E)-2-(2-(1H-Indol-3-yl)vinyl)-3-(4-((6-methoxynaphthalen-2-yl)ethynyl)-2-methylphenyl)quinazolin-4(3H)-one (16a);

(E)-2-(2-(5-Methoxy-1H-indol-3-yl)vinyl)-3-(4-((6-methoxynaphthalen-2-yl)ethynyl)-2-methylphenyl)quinazolin-4(3H)-one (16b);

(E)-2-(2-(1H-Indol-3-yl)vinyl)-3-(2-methyl-4-(pyridin-3-ylethynyl)phenyl)quinazolin-4(3H)-one (17a);

(E)-2-(2-(5-Methoxy-1H-indol-3-yl)vinyl)-3-(2-methyl-4-(pyridin-3-ylethynyl)phenyl)quinazolin-4(3H)-one (17b);

(E)-2-(2-(1H-Indol-3-yl)vinyl)-3-(2-methyl-4-(thiophen-2-ylethynyl)phenyl)quinazolin-4(3H)-one (18a);
(E)-2-(2-(5-Methoxy-1H-indol-3-yl)vinyl)-3-(2-methyl-4-(thiophen-2-ylethynyl)phenyl)quinazolin-4(3H)-one (18b);
(E)-3-(2-Methyl-4-(phenylethynyl)phenyl)-2-(2-(naphthalen-2-yl)vinyl)quinazolin-4(3H)-one (19a);
(E)-3-(2-Methyl-4-(phenylethynyl)phenyl)-2-(2-(quinolin-6-yl)vinyl)quinazolin-4(3H)-one (19b);
(E)-3-(4-((4-Tert-butylphenyl)ethynyl)-2-methylphenyl)-2-(2-(naphthalen-2-yl)vinyl)quinazolin-4(3H)-one (20a);
(E)-3-(4-((4-Tert-butylphenyl)ethynyl)-2-methylphenyl)-2-(2-(quinolin-6-yl)vinyl)quinazolin-4(3H)-one (20b);
(E)-3-(4-((6-Methoxynaphthalen-2-yl)ethynyl)-2-methylphenyl)-2-(2-(naphthalen-2-yl)vinyl)quinazolin-4(3H)-one (21a);
(E)-3-(4-((6-Methoxynaphthalen-2-yl)ethynyl)-2-methylphenyl)-2-(2-(quinolin-6-yl)vinyl)quinazolin-4(3H)-one (21b);
(E)-3-(2-Methyl-4-(pyridin-3-ylethynyl)phenyl)-2-(2-(naphthalen-2-yl)vinyl)quinazolin-4(3H)-one (22a);
(E)-3-(2-Methyl-4-(pyridin-3-ylethynyl)phenyl)-2-(2-(quinolin-6-yl)vinyl)quinazolin-4(3H)-one (22b);
(E)-3-(2-Methyl-4-(thiophen-2-ylethynyl)phenyl)-2-(2-(naphthalen-2-yl)vinyl)quinazolin-4(3H)-one (23a);
(E)-3-(2-Methyl-4-(thiophen-2-ylethynyl)phenyl)-2-(2-(quinolin-6-yl)vinyl)quinazolin-4(3H)-one (23b).

In yet another embodiment of the present invention, structural formulae of the 3-Arylethynyl substituted quinazolinone compounds of general formula A are:

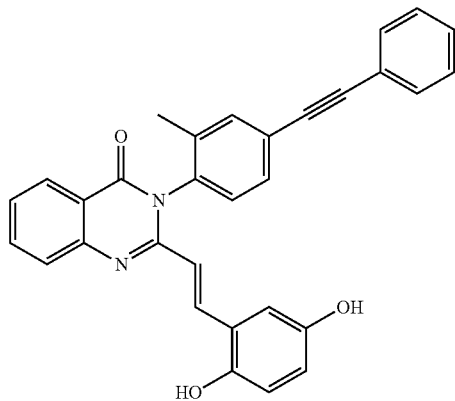

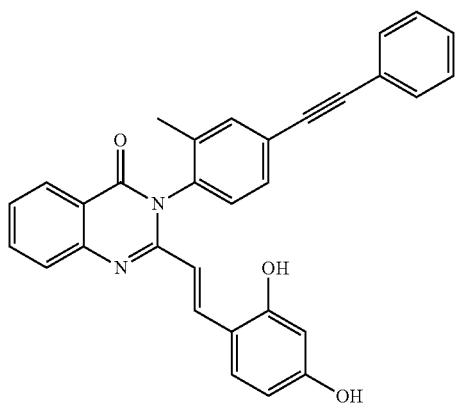

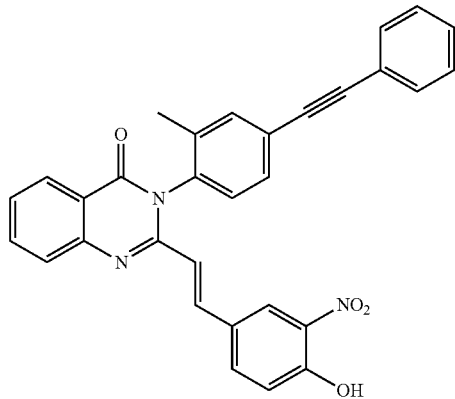

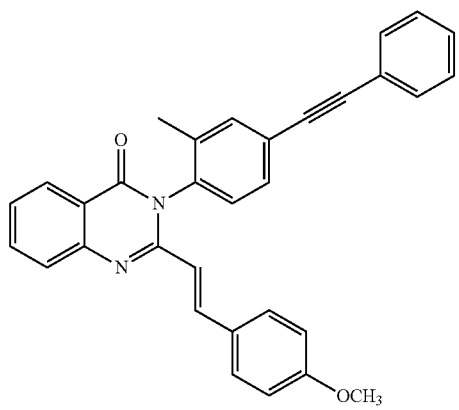

4g
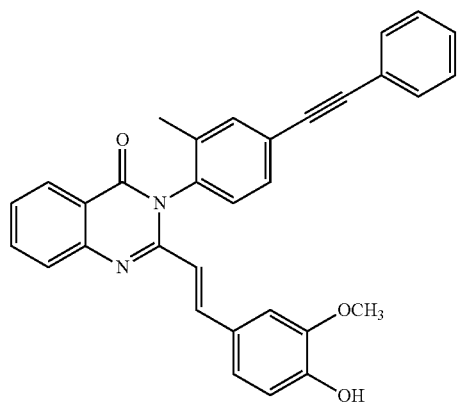
4h
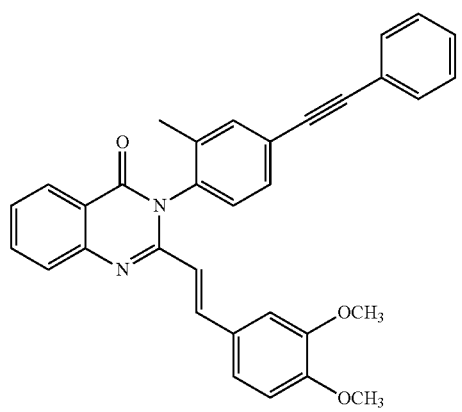
4i
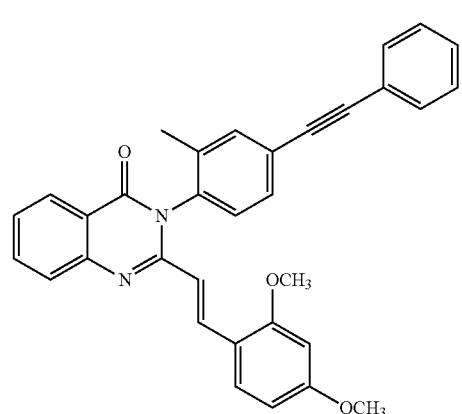
4j
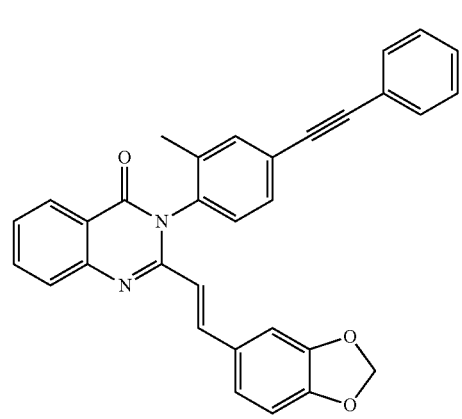
4k
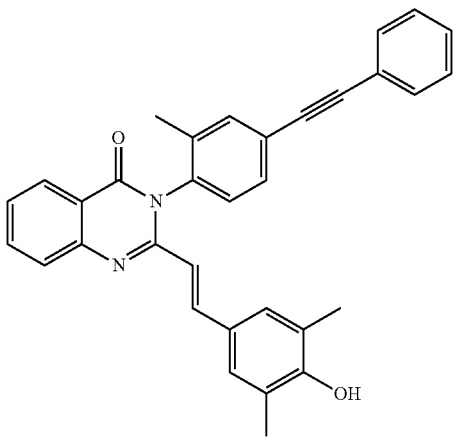
4l
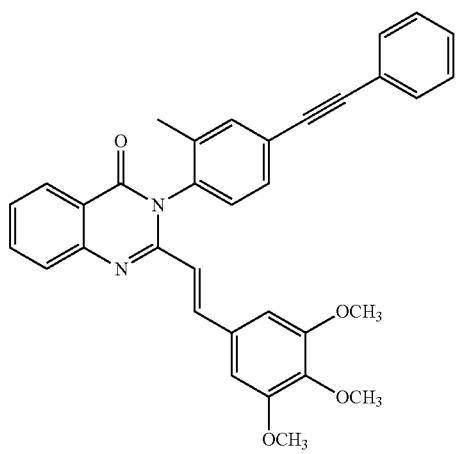
4m
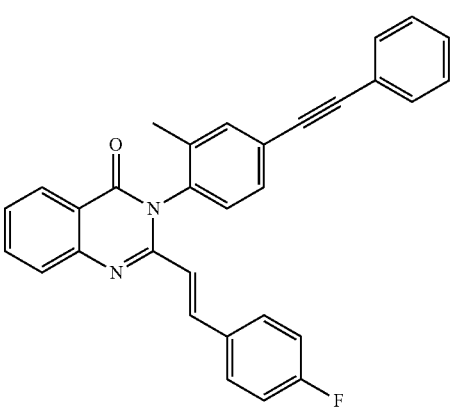

4n
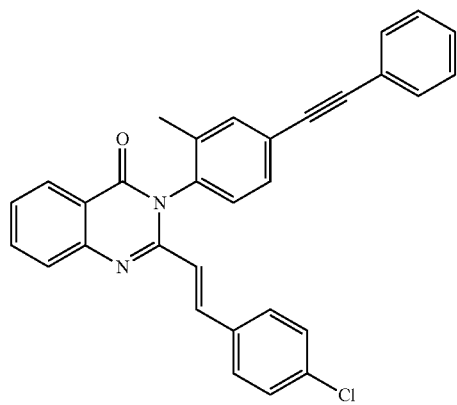
5a
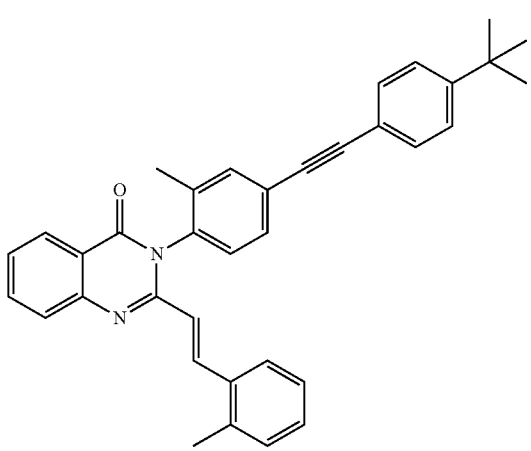
5b
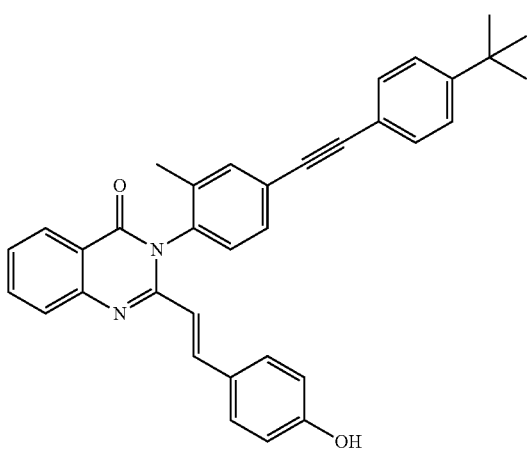
5c
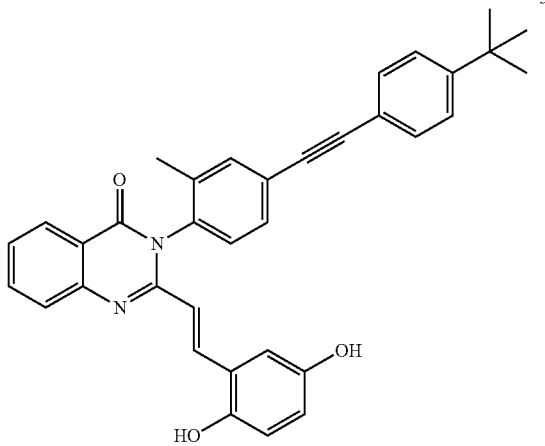
5d
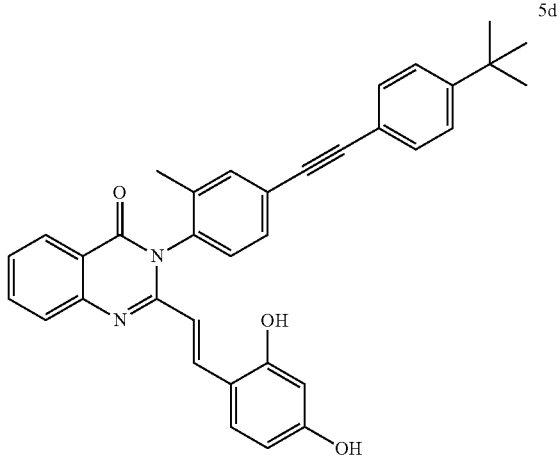
5e
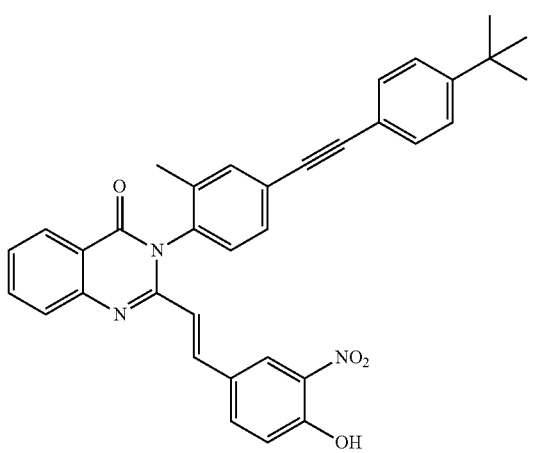

-continued

5f

5g

5h

-continued

5i

5j

5k

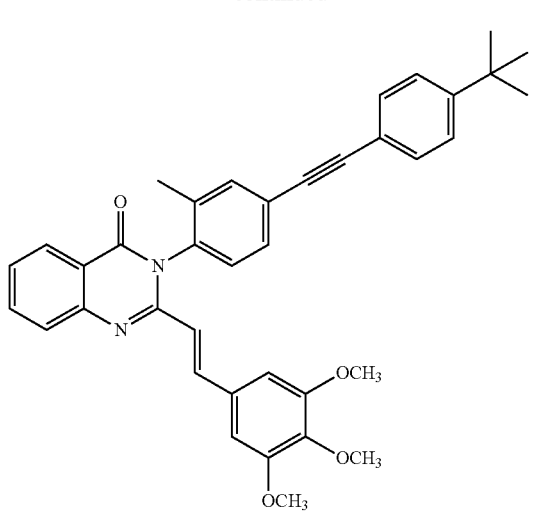
5l
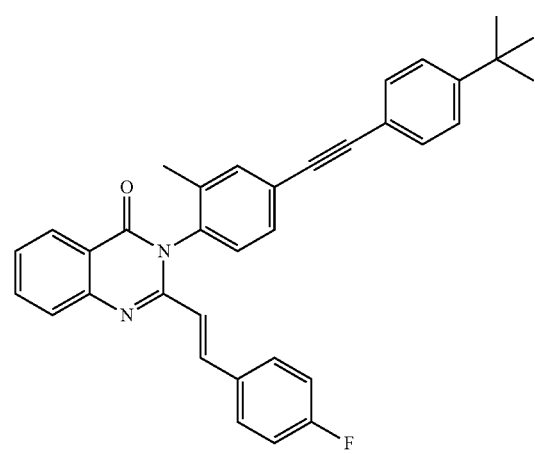
5m
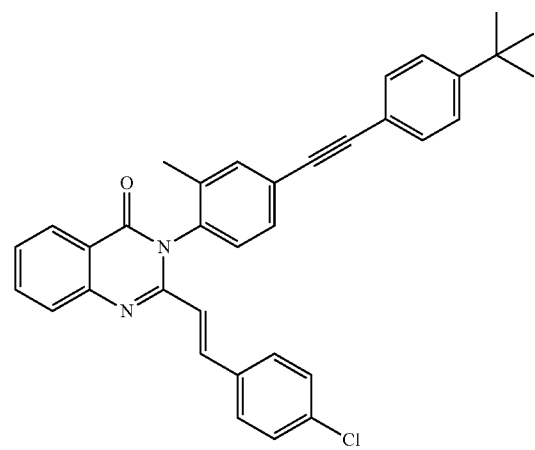
5n
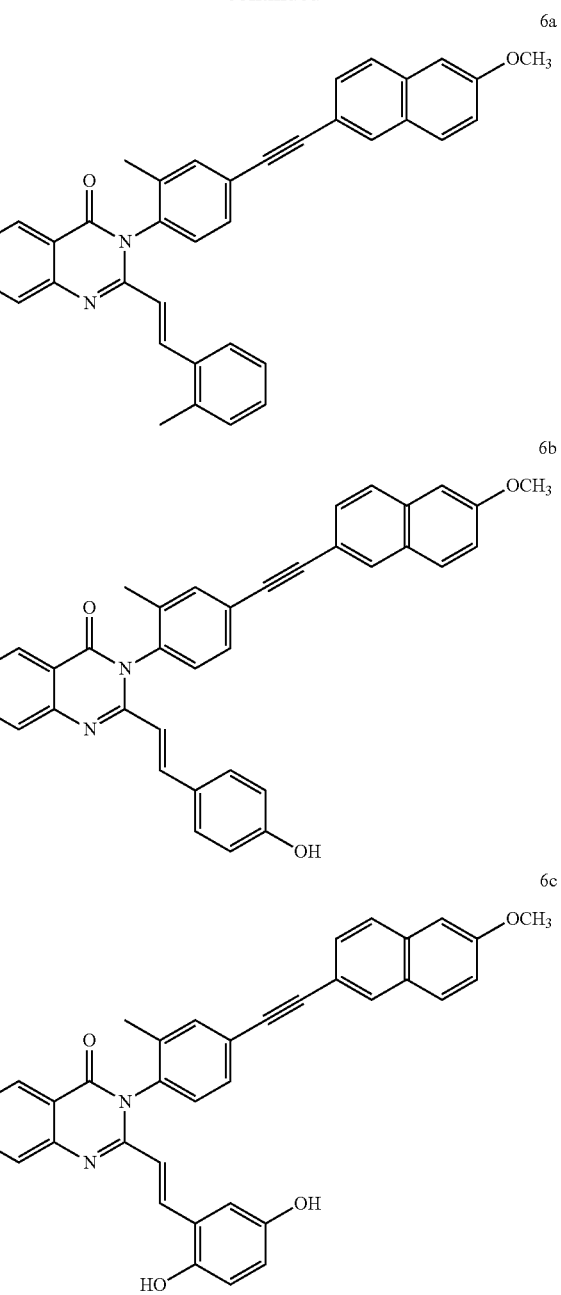

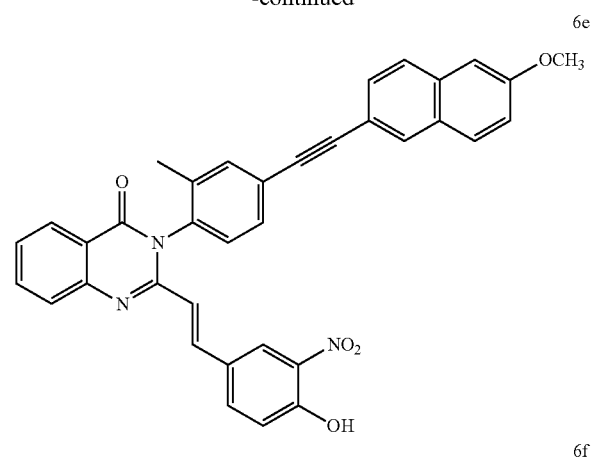
6e
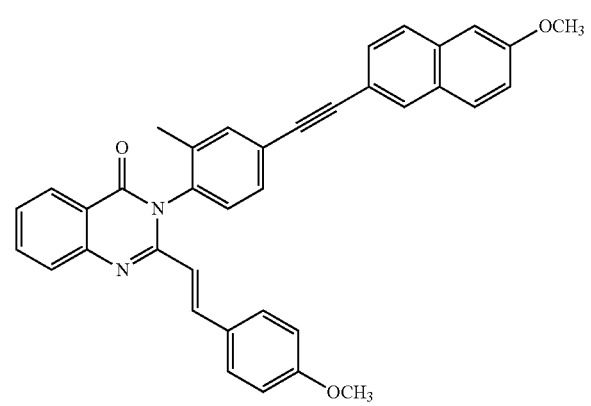
6f
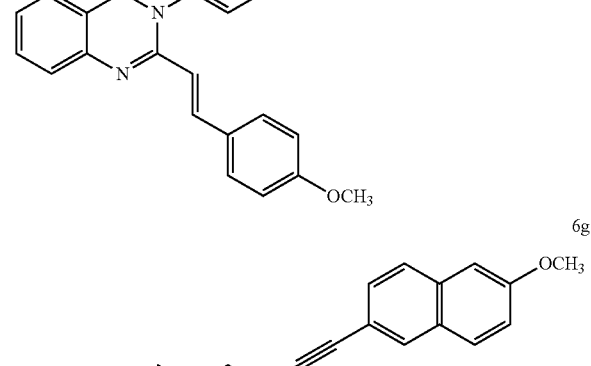
6g
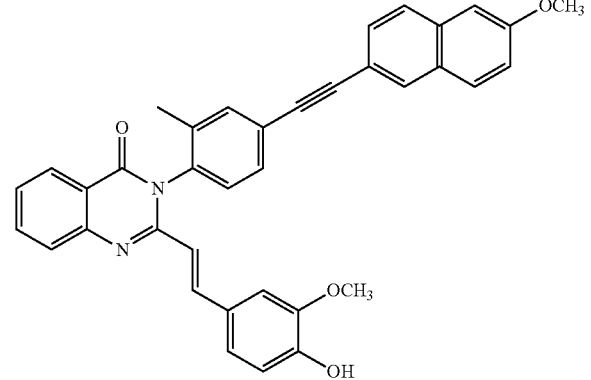
6h
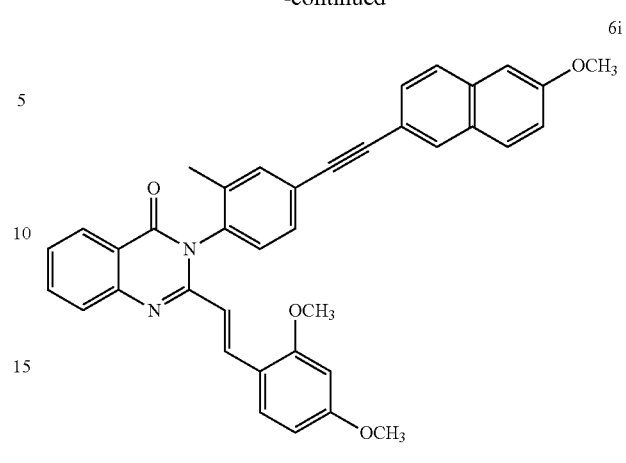
6i
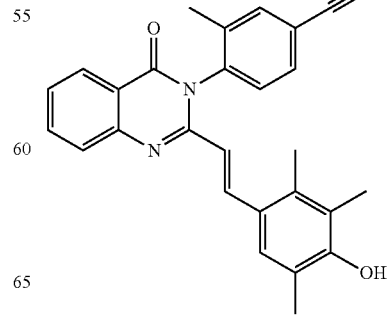
6j
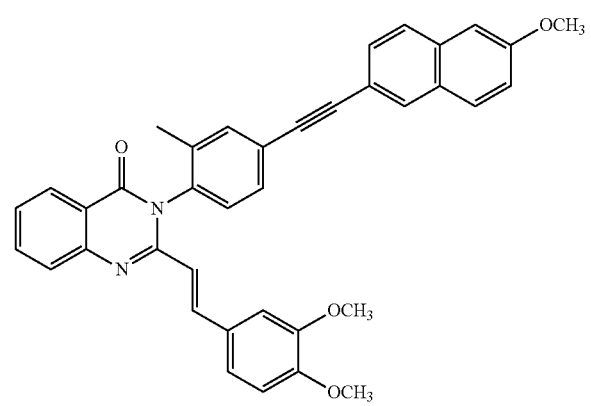
6k 6l
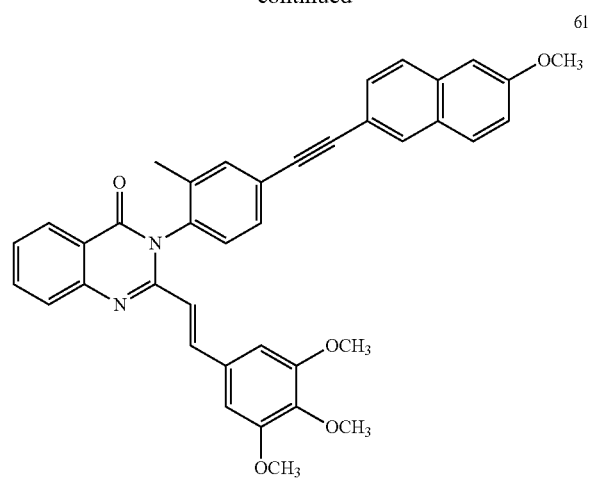
6m
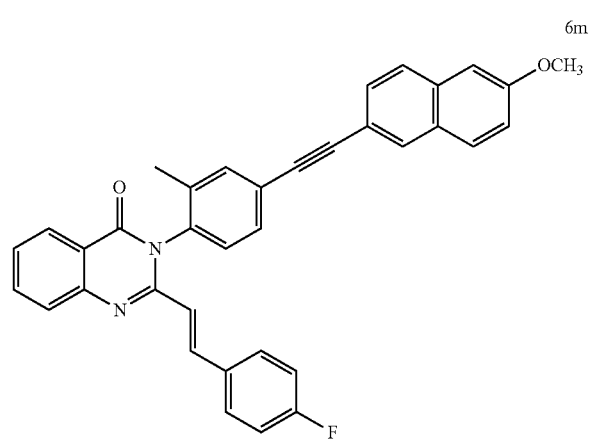
6n
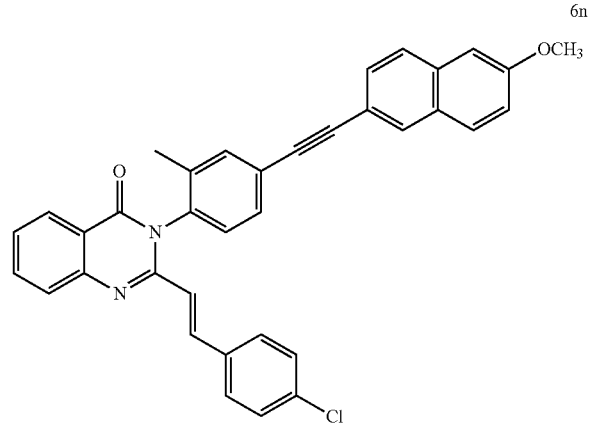
7a
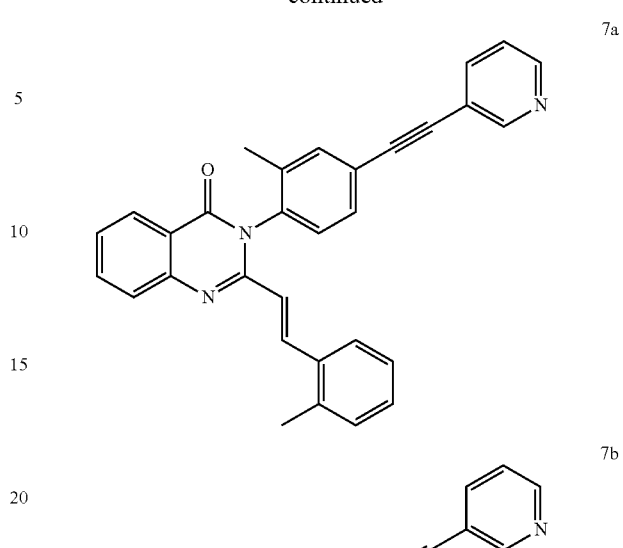
7b
7c
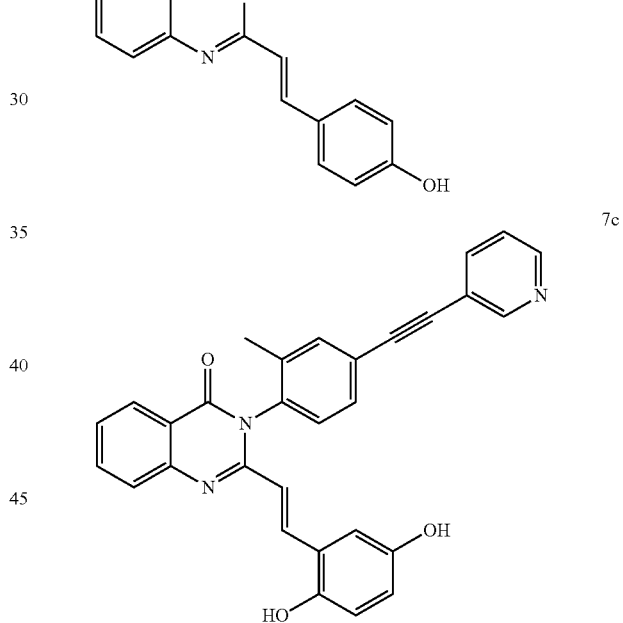
7d
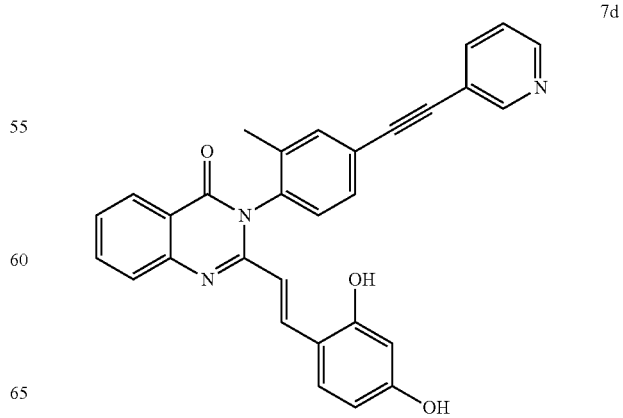

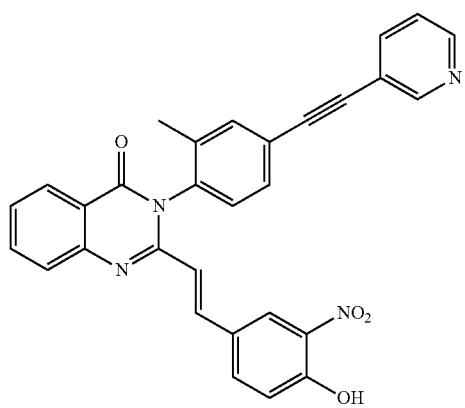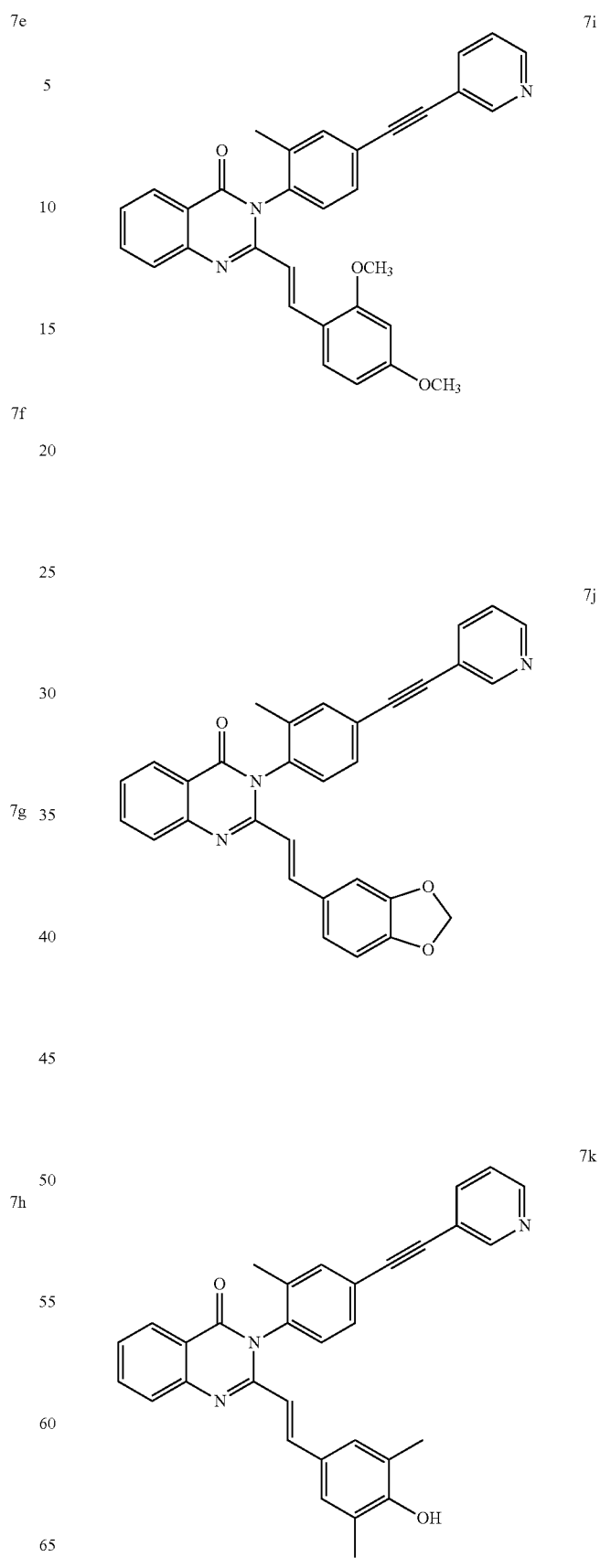

-continued
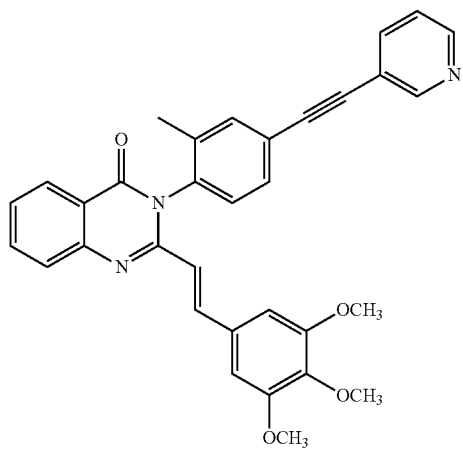
7l
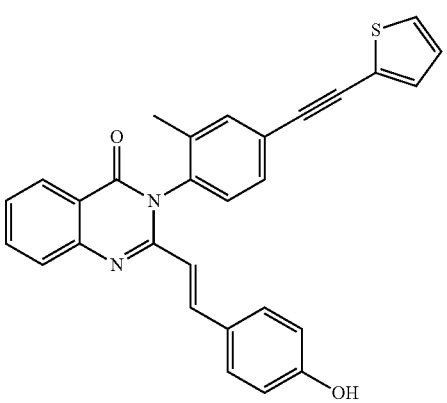
8b
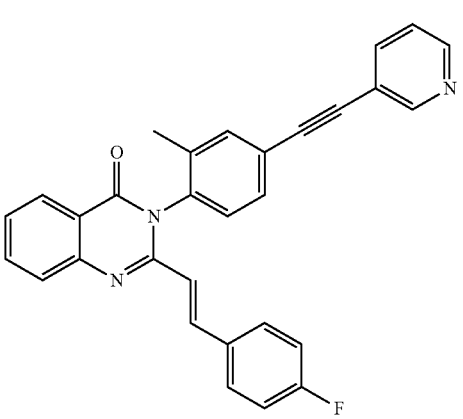
7m
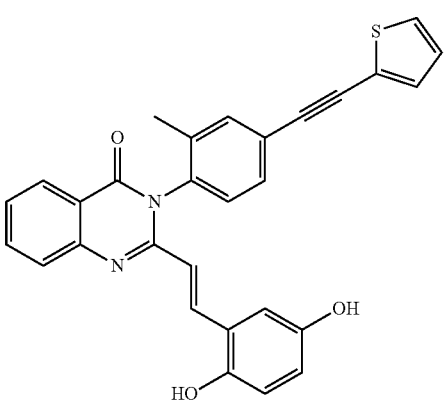
8c
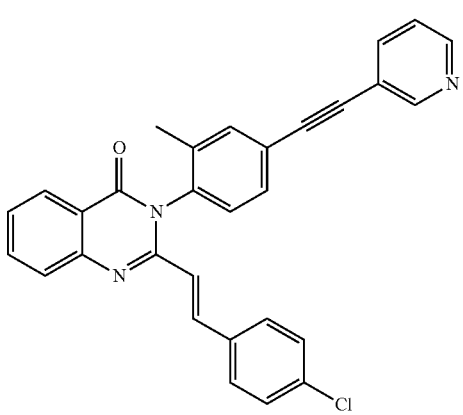
7n
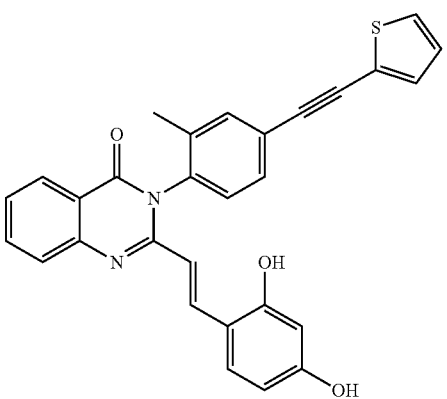
8d
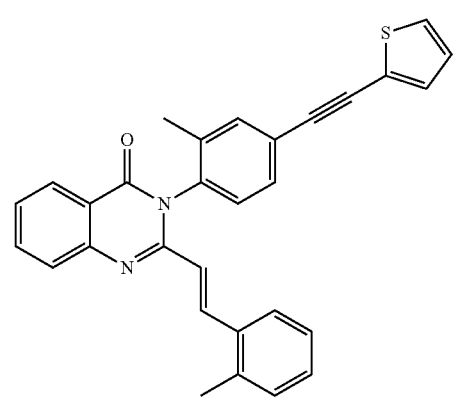
8a
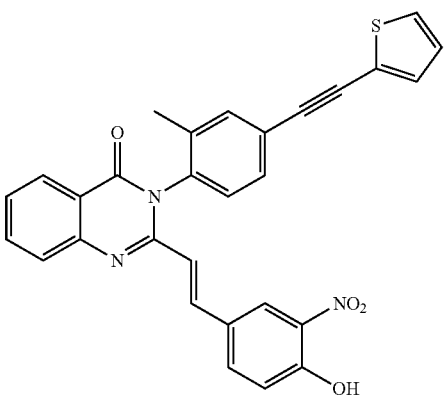
8e

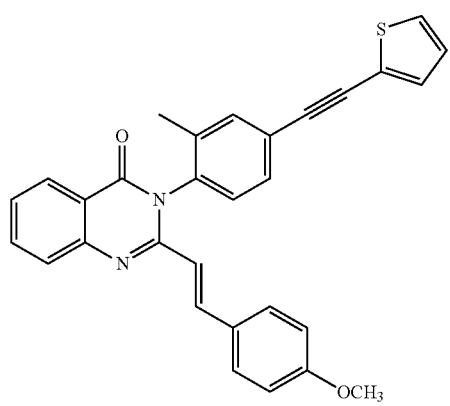
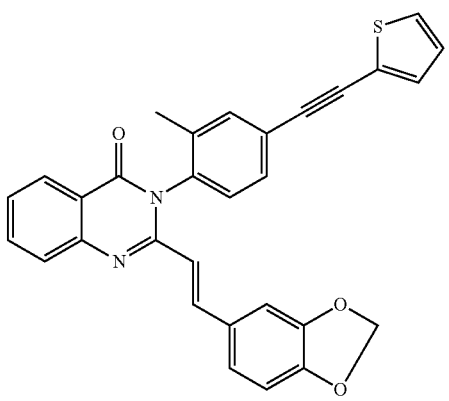

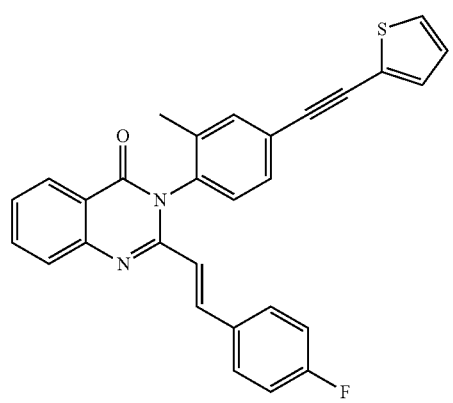
8m
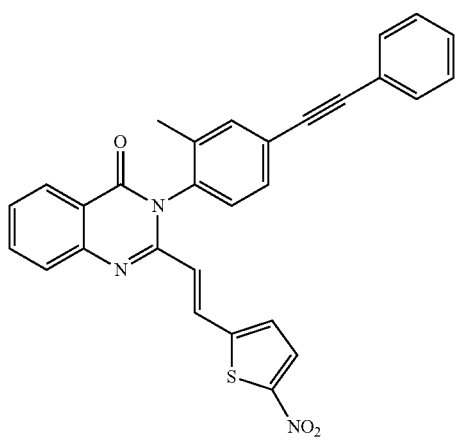
9b
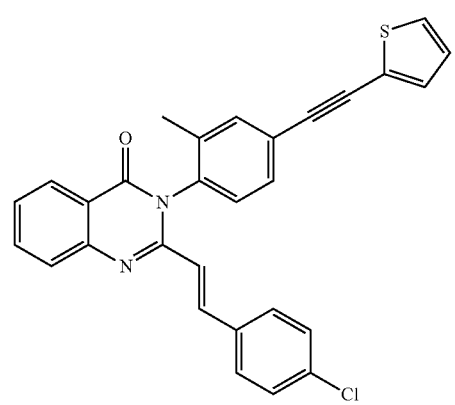
8n
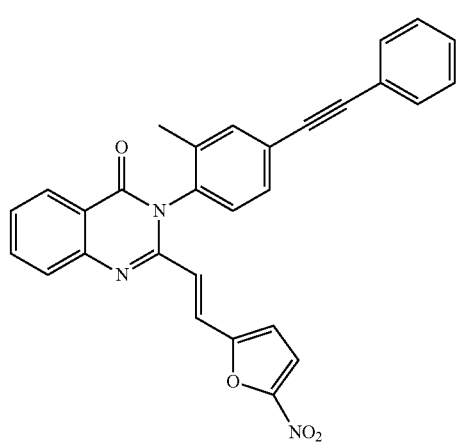
9a

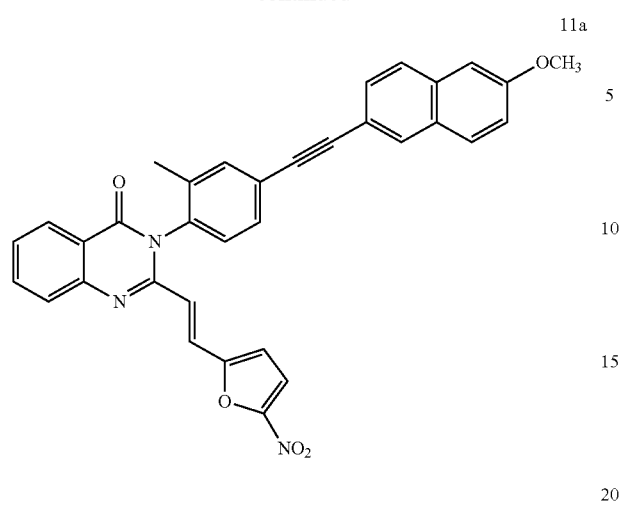
11a
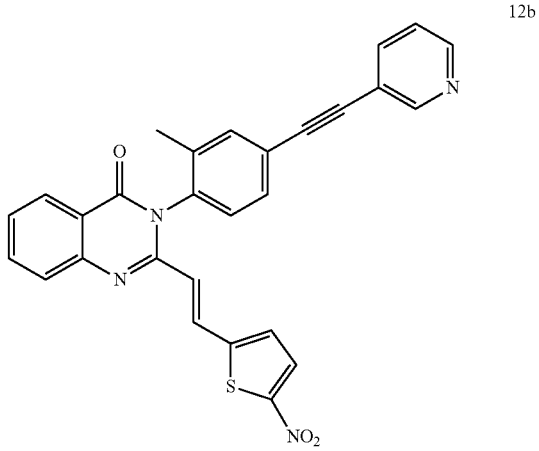
12b
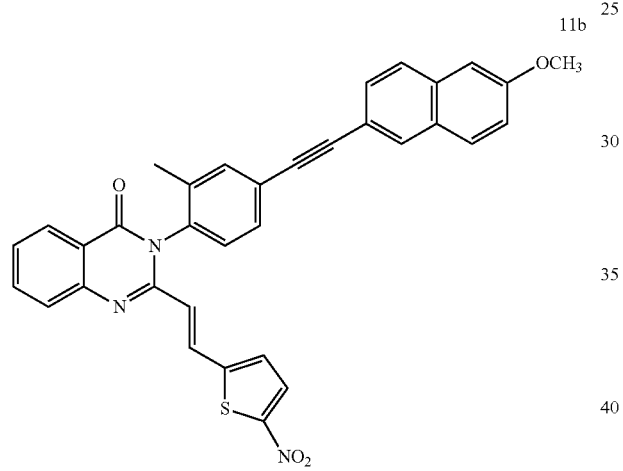
11b
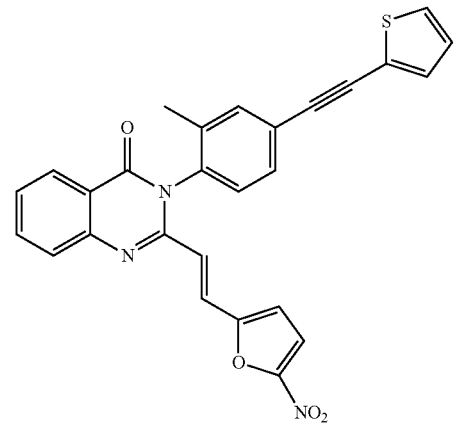
13a
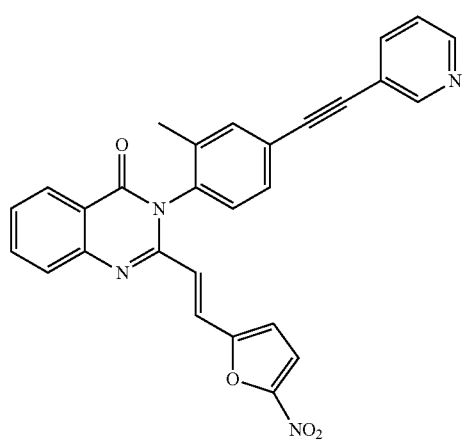
12a
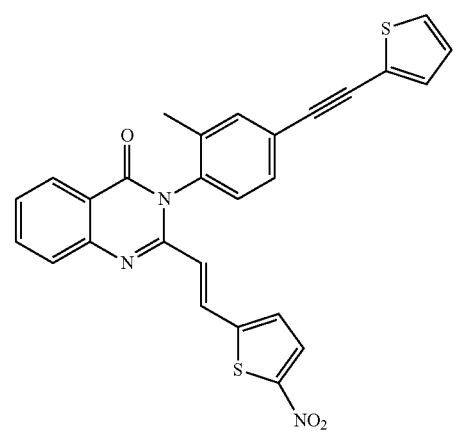
13b 35
-continued
14a
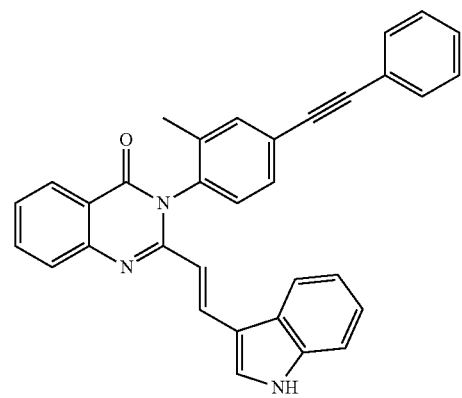
14b
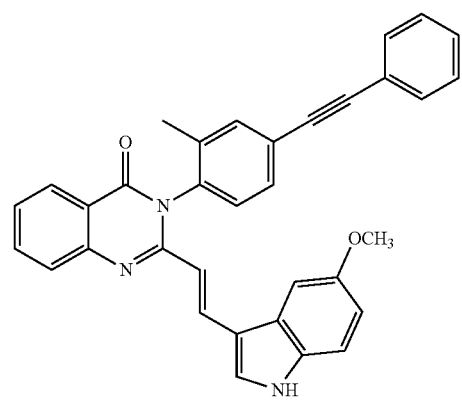
15a
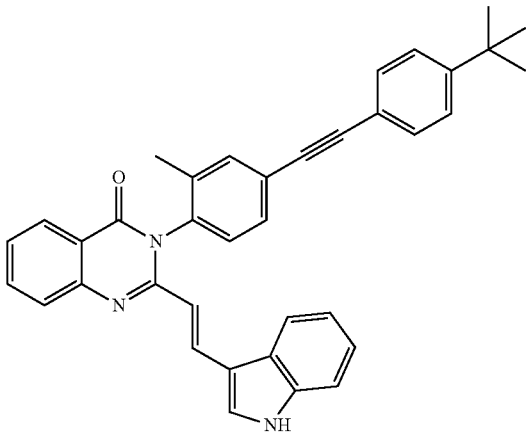
36
-continued
15b
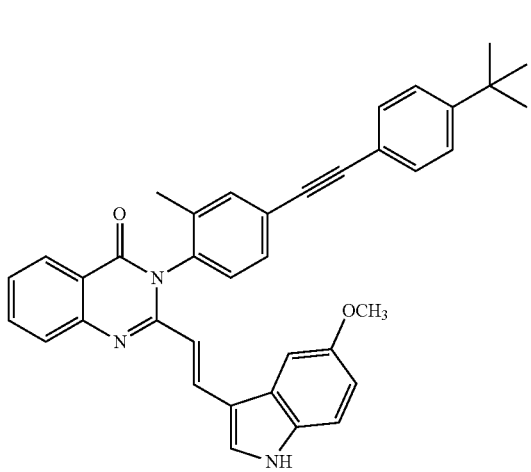
16a
16b
17a
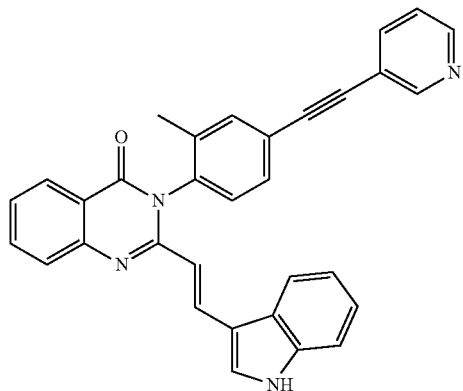

37
-continued
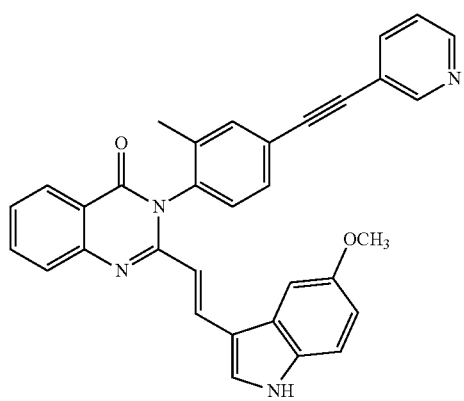
17b
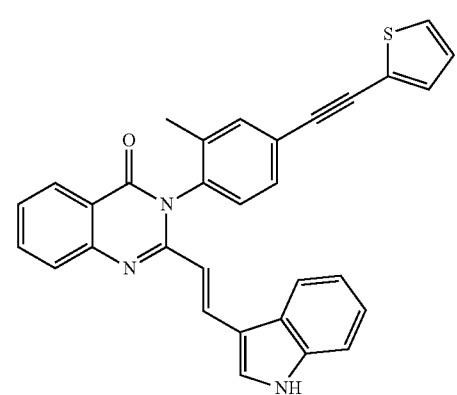
18a
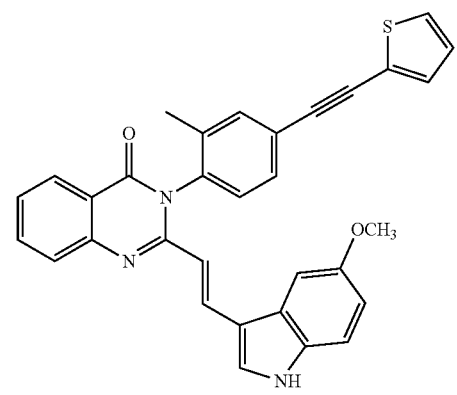
18b
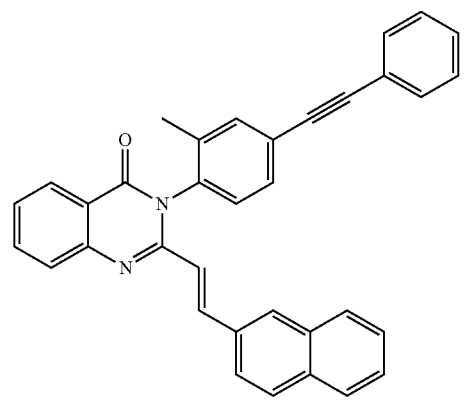
19a
38
-continued
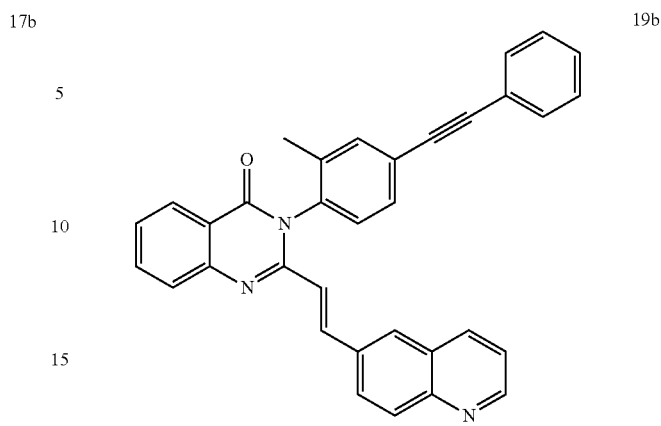
19b
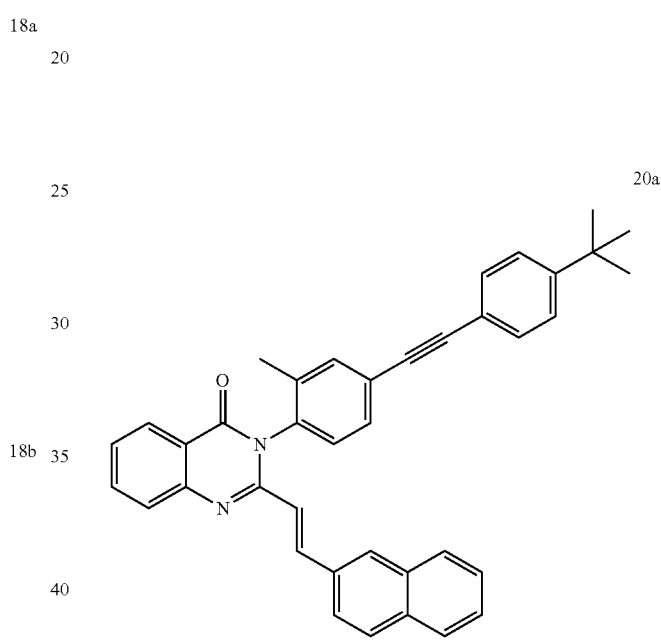
20a
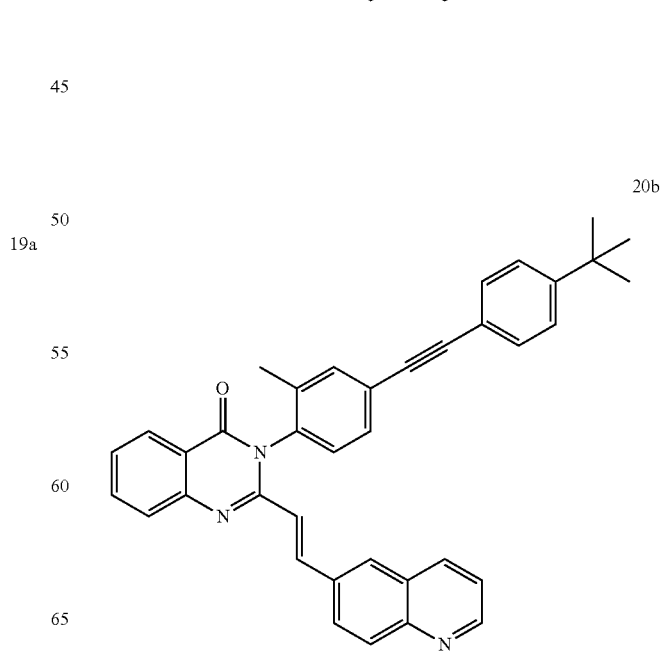
20b

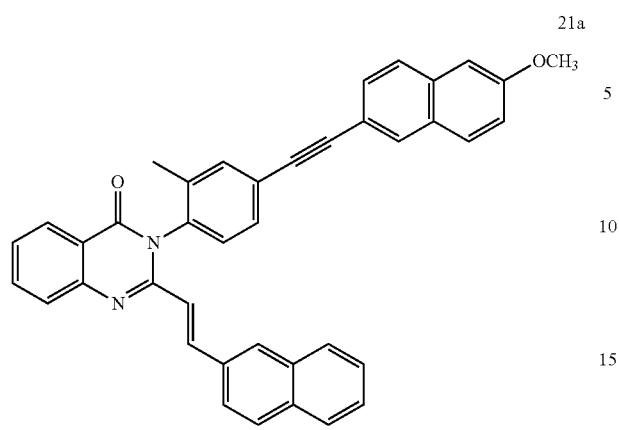

21a

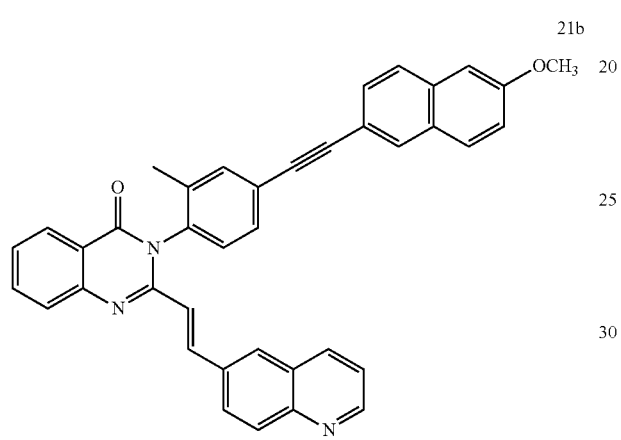

21b

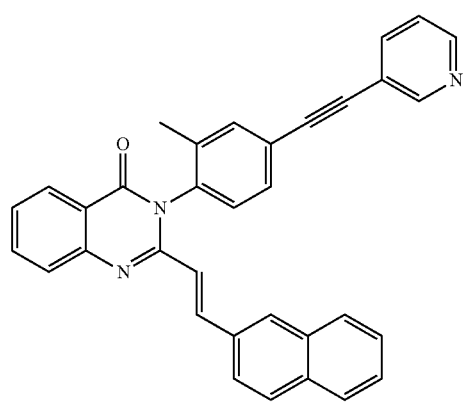

22a

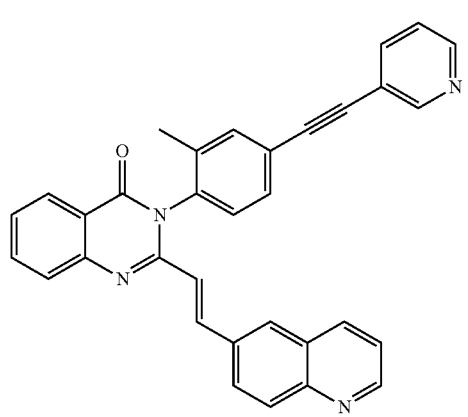

22b

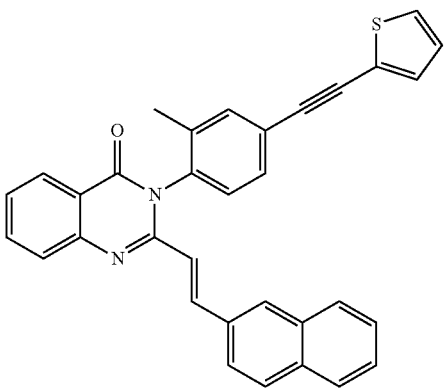

23a

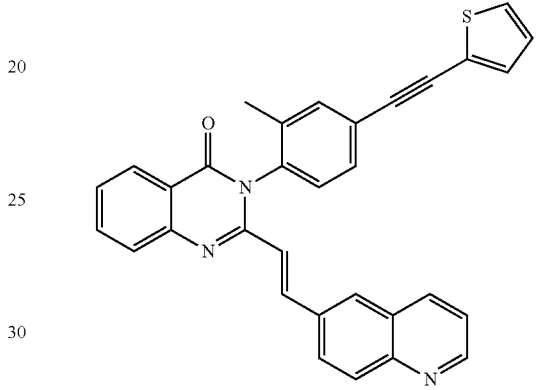

23b

In yet another embodiment of the present invention, 3-Arylethynyl substituted quinazolinone compounds are useful as anticancer agent.

In yet another embodiment of the present invention, 3-Arylethynyl substituted quinazolinone compounds of formula 4b, 4c, 5d and 6l exhibiting an in vitro anticancer activity against sixty human cancer cell lines derived from nine cancer types leukemia cell line, non small cell lung cell line, colon cell line, CNS cell line, renal cell line, prostate cell line, ovarian cell line, breast and melanoma cell line. In yet another embodiment of the present invention, 3-Arylethynyl substituted quinazolinone compounds of formula 4b, 4c, 5d and 6l exhibiting an in vitro anticancer activity against six leukemia cancer cell lines (CCRF-CEM, HL-60, K-562, MOLT-4, SR and RPMI-8226) for $GI_{50}$ are in the range of 1.66 to 3.26, 0.634 to 1.54, 2.45 to 3.85 and 0.395 to 4.66 μM, respectively at an exposure period of at least 48 h.

In yet another embodiment of the present invention, 3-Arylethynyl substituted quinazolinone compounds of formula 4b, 4c, 5d and 6l exhibiting an in vitro anticancer activity against nine non-small cell lung cancer cell lines (A549/ATCC, EKVX, HOP-62, HOP-92, NCI-H226, NCI-H23, NCI-H322M, NCI-H460 and NCI-H522) for $GI_{50}$ are in the range of 2.22 to 13.1, 1.24 to 1.71, 1.82 to 6.09 and 2.48 to 40.5 μM, respectively at an exposure period of at least 48 h.

In yet another embodiment of the present invention, 3-Arylethynyl substituted quinazolinone compounds of formula 4b, 4c, 5d and 6l exhibiting an in vitro anticancer activity against seven colon cancer cell line (COLO 205, HCC-2998, HCT-116, HCT-15, HT29, KM12 and SW-620) for $GI_{50}$ are in the range of 1.99 to 4.08, 1.03 to 1.95, 1.81 to 3.33 and 1.22 to 17.2 μM, respectively at an exposure period of at least 48 h.

In yet another embodiment of the present invention, 3-Arylethynyl substituted quinazolinone compounds of formula 4b, 4c, 5d and 6l exhibiting an in vitro anticancer activity against six CNS cancer cell line (SF-268, SF-295, SF-539, SNB-19, SNB-75 and U251) for $GI_{50}$ are in the range of 2.85 to 6.91, 1.30 to 1.62, 1.87 to 7.90, 7.40 μM, respectively at an exposure period of at least 48 h.

In yet another embodiment of the present invention, 3-Arylethynyl substituted quinazolinone compounds of formula 4b, 4c, 5d and 6l said compounds exhibiting an in vitro anticancer activity against eight renal cancer cell line (786-0, A498, ACHN, CAKI-1, SN12C, TK-10, UO-31 and RXF 393) for are in the range of 1.56 to 3.77, 0.370 to 2.15, 1.88 to 5.08, 4.91 μM, respectively at an exposure period of at least 48 h.

In yet another embodiment of the present invention, 3-Arylethynyl substituted quinazolinone compounds of formula 4b, 4c, 5d exhibiting an in vitro anticancer activity against two prostate cancer cell line (PC-3, DU-145) for $GI_{50}$ are 3.24 to 4.87, 0.419 to 2.19, 3.42 to 3.67 μM, respectively at an exposure period of at least 48 h.

In yet another embodiment of the present invention, 3-Arylethynyl substituted quinazolinone compounds of formula 4b, 4c, 5d and 6l exhibiting an in vitro anticancer activity against seven ovarian cancer cell lines (IGROV1, OVCAR-3, OVCAR-4, OVCAR-5, OVCAR-8, NCI/ADR-RES and SK-OV-3) for $GI_{50}$ are in the range of 3.09 to 20.6, 1.39 to 2.45, 2.23 to 10.9 and 19.3 μM respectively at an exposure period of at least 48 h.

In yet another embodiment of the present invention, 3-Arylethynyl substituted quinazolinone compounds of formula 4b, 4c, 5d and 6l exhibiting an in vitro anticancer activity against six breast cancer cell line (MCF-7, MDA-MB-231/ATCC, HS 578T, TD-47D, MDA-MB-468 and BT-549) for $GI_{50}$ are in the range of 2.02 to 3.89, 1.14 to 1.61, 2.20 to 8.60, 3.80 to 63.8 μM, respectively at an exposure period of at least 48 h.

In yet another embodiment of the present invention, 3-Arylethynyl substituted quinazolinone compounds of formula 4b, 4c, 5d and 6l exhibiting an in vitro anticancer activity against nine melanoma cancer cell line (LOX IMVI, MALME-3M, M14, MDA-MB-435, SK-MEL-2, SK-MEL-28, SK-MEL-5, UACC-257 and UACC-62) for $GI_{50}$ are in the range of 1.77 to 4.54, 1.35 to 1.67, 1.49 to 8.42 and 1.85 to 42.6 μM, respectively at an exposure period of at least 48 h.

In yet another embodiment of the present invention, a process for the preparation of 3-arylethynyl substituted quinazolinone compounds of general formula A and the said process comprising the steps of:
  i. treating 4-iodo-2-methylbenzenamine (24) with substituted aryl (hetero) ethynyl compounds of formulae (25a-e) which represent phenyl, 4-tertiary butyl phenyl, 6-methoxy naphthaalene, 3-pyridyl, 2-thiophenyl ethynyl compounds by employing Sonagashira coupling conditions using $Pd(PPh_3)_4$ as catalyst, CuI as cocatalyst, butyl amine as base and ether as solvent and kept the reaction for 6-8 h to gave 2-methyl-4-(phenylethynyl) benzenamine compounds (26a-e) wherein G represent phenyl, 4-tertiary-butyl phenyl, 6-methoxy naphthalene, 3-pyridyl, 2-thiophenyl;

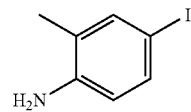

24

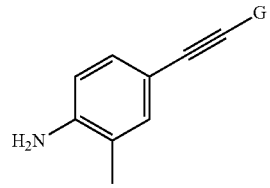

26a-e

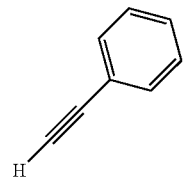

25a

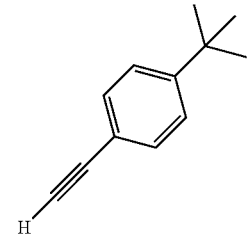

25b

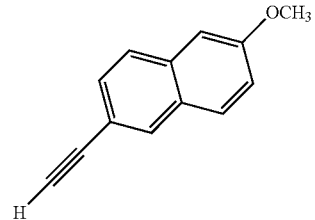

25c

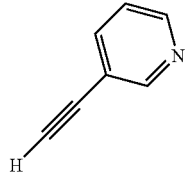

25d

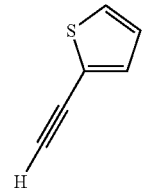

25e ii. treating anthranilic acids (27) with acetic anhydride at temperature in the range of 150-155° C. for period in the range of 30-45 min afforded 2-methyl-4H-benzo[d][1, 3]oxazin-4-one compound (28);

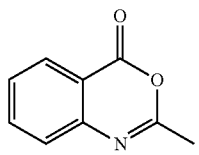

28 iii. mixing 2-methyl-4-(phenylethynyl)benzenamine compounds (26a-e) as obtained in step (i) with 2-methyl-4H-benzo[d][1,3]oxazin-4-one (28) as obtained in step (ii) in acetic acid was heated under reflux conditions (120-125° C.) for 8-10 h afford 2-methyl-3-(2-methyl-4-(phenylethynyl)phenyl)quinazolin-4(3H)-one (29a-e);

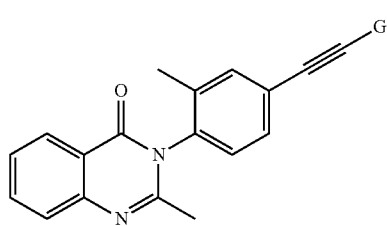

29a-e iv. treating 2-methyl-3-(2-methyl-4-(phenylethynyl)phenyl)quinazolin-4(3H)-one (29a-e) as obtained in step (iii) with aldehydes of formula 30a-n, 31a-b, 32a-b and 33a-b in acetic acid was heated under reflux conditions (120-125° C.) for 8-10 h to obtain the final compounds 4a-n to 8a-n, 9a-b to 23a-b of general formula A.

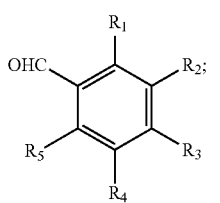

30a-n

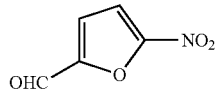

31a

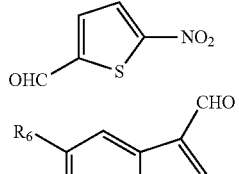

31b

32a; R₆ = H
32b; R₆ = OCH₃

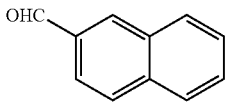

33a

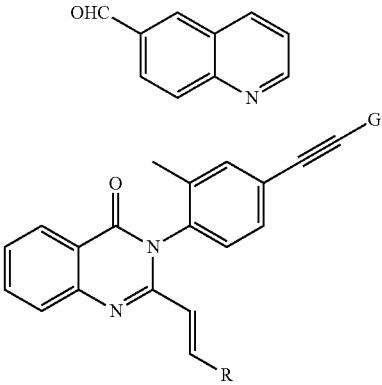

4a-i to 8a-i; 9a-b to 23a-b

DETAILED DESCRIPTION OF THE INVENTION

Figure 1:
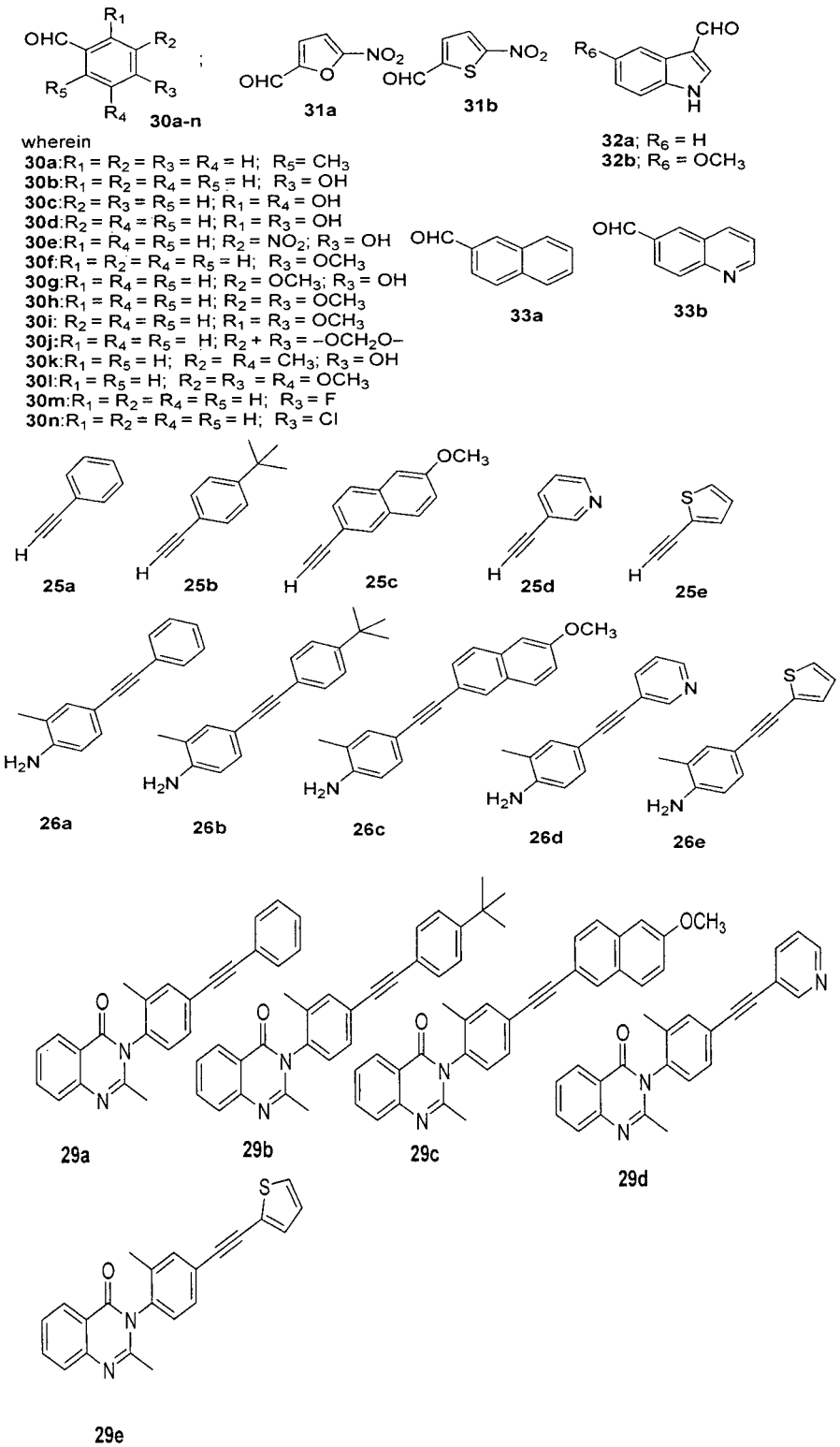
FIG. 1 represents structural formula of compounds of formula 30a-n, 31a-b, 32a-b, 33a-b, 25a-e, 26a-e, 29a-e.
Figure 2:
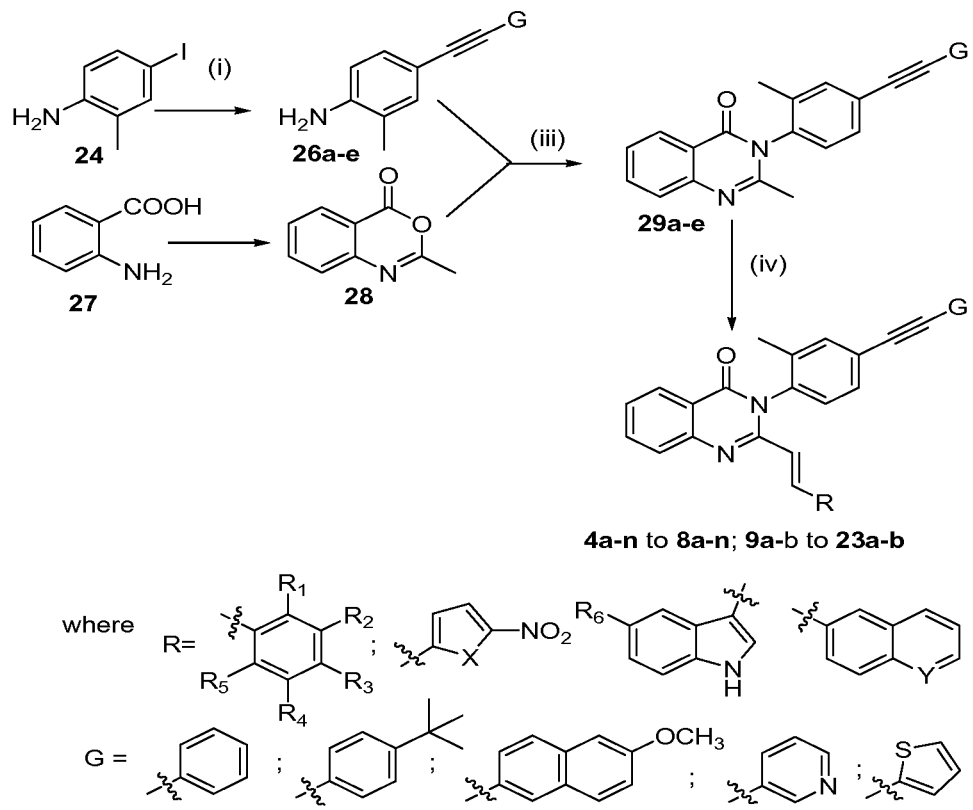
FIG. 2 (Scheme 1) represents the flow diagram for the preparation of compound of general formula A wherein reagent and conditions are (i) substituted phenyl acetylenes, Pd(PPh₃)₄, CuI, BuNH₂, ether, rt (room temperature 25 to 30° C.), 6h; (ii) Ac₂O, 150° C., 30 min; (iii) aryl ethynyl anilines, AcOH, reflux, 8 h; (iv) Substituted aldehydes, AcOH, reflux, 8 h.

3-Arylethynyl substituted quinazolinone compounds have shown promising anticancer activity in various cell lines. The molecules synthesized are of immense biological significance. This resulted in design and synthesis of new congeners as illustrated in Scheme-1, which comprise:

i. Sonagasira coupling reaction between various phenyl acetylenes and 4-iodo-2-methylbenzenamine.
ii. Cyclization of anthranilic acid on reaction with acetic anhydride at 150° C. for 30 min.
iii. Insertion reaction of 2-methyl-4-(phenylethynyl)benzenamine and 2-methyl-4H-benzo[d][1,3]oxazin-4-one in acetic acid under reflux conditions afforded 2-methyl-3-(2-methyl-4-(phenylethynyl)phenyl)quinazolin-4(3H)-one.
iv. The synthesis of 3-Arylethynyl substituted quinazolinone compounds as potential anticancer agents were synthesized by the reaction of 2-methyl-3-(2-methyl-4-(phenylethynyl)phenyl)quinazolin-4(3H)-one with various substituted aldehydes at room temperature to gave the final compounds.
v. Purification by column chromatography using different solvents like ethyl acetate, hexane, chloroform and methanol.

The 3-arylethynyl substituted quinazolinone compounds exhibited significant anticancer activity against sixty human cancer cell lines.

EXAMPLES

The following examples are given by way of illustration of the present invention and therefore should not be construed to limit the scope of the present invention.

Example 1

(E)-2-(4-hydroxystyryl)-3-(2-methyl-4-(phenylethynyl)phenyl)quinazolin-4(3H)-one (4b)

4-iodo-2-methylbenzenamine (24, 233 mg, 1 mmol) on reaction with ethynyl benzene (25a, 102 mg, 1 mmol) by employing Sonagashira coupling conditions using Pd(PPh$_3$)$_4$ (69.3 mg, 0.06 equiv) as catalyst, CuI (22.8 mg, 0.12 equiv) as cocatalyst, butyl amine (261 mg, 3 equiv) as base and ether as solvent and kept the reaction for 6 h. After completion of the reaction as indicated by TLC and the reaction mixture is extracted into ether (4×25 mL) from the aqueous layer and concentrated in vacuo. The compound was further purified by column chromatography using 60-120 silica gel (ethyl acetate/hexane, 1:9) to obtain 2-methyl-4-(phenylethynyl) benzenamine compound (26a) as pure product. Anthranilic acid (27, 137 mg, 1 mmol) on reaction with acetic anhydride at 150° C. and reflux for 30 min, after completion of reaction aqueous sodium bicarbonate solution is added and extracted in ethyl acetate (4×25 mL) from the aqueous layer and concentrated in vacuo afforded 2-methyl 4H-benzo[d][1,3]oxazin-4-one compound (28) as pure product. To a stirred solution of 2-methyl-4-(phenylethynyl)benzenamine (26a, 207 mg, 1 mmol) with 2-methyl-4H-benzo[α][1,3]oxazin-4-one (28, 161 mg, 1 mmol) in acetic acid and reflux for 8 h. After completion of the reaction as indicated by TLC. The reaction mixture was quenched with NaHCO$_3$ and extracted in ethyl acetate (4×25 mL) from the ice cold aqueous layer and dried over anhydrous Na$_2$SO$_4$ afforded 2-methyl-3-(2-methyl-4-(phenylethynyl)phenyl)quinazolin-4(3H)-one (29a). Reaction of 2-methyl-3-(2-methyl-4-(phenyl ethynyl)phenyl)quinazolin-4(3H)-one (29a, 350 mg, 1 mmol) with 4-hydroxy benzaldehyde (30b, 122 mg, 1 mmol) was taken in acetic acid Then the resulting mixture was stirred under reflux conditions for 8 h and then the reaction mixture was quenched with NaHCO$_3$ and extracted in ethyl acetate (4×25 mL) from the ice cold aqueous layer and dried over anhydrous Na$_2$SO$_4$. The resulting product (4b) was purified by column chromatography employing EtOAc/Hexane as an eluent.

Mp 161-162° C.; $^1$H NMR (CDCl$_3$+DMSO-d$_6$, 200 MHz) δ 8.29 (s, 1H), 8.27 (d, J=15.1 Hz, 1H), 7.77 (d, J=3.6 Hz, 2H), 7.57 (d, J=9.4, 1H), 7.52 (dd, J=3.9, 7.5 Hz, 2H), 7.46 (t, J=3.9 Hz, 1H), 7.40-7.27 (m, 3H), 7.26-7.06 (m, 6H), 6.25 (d, J=15.3 Hz, 1H), 2.16 (s, 3H); LRMS (ESI, m/z) 455 (M)$^+$.

Example 2

(E)-2-(2,5-dihydroxystyryl)-3-(2-methyl-4-(phenylethynyl)phenyl)quinazolin-4(3H)-one (4c)

4-iodo-2-methylbenzenamine 24 (233 mg, 1 mmol) on reaction with ethynyl benzene (25a, 102 mg, 1 mmol) by employing Sonagashira coupling conditions using Pd(PPh$_3$)$_4$ (69.3 mg, 0.06 equiv) as catalyst, CuI (22.8 mg, 0.12 equiv) as cocatalyst, butyl amine (261 mg, 3 equiv) as base and ether as solvent and kept the reaction for 6 h. After completion of the reaction as indicated by TLC and the reaction mixture is extracted into ether (4×25 mL) from the aqueous layer and concentrated in vacuo. The compound was further purified by column chromatography using 60-120 silica gel (ethyl acetate/hexane, 1:9) to obtain 2-methyl-4-(phenylethynyl) benzenamine compounds (26a) as pure product. Anthranilic acid (27, 137 mg, 1 mmol) on reaction with acetic anhydride at 150° C. and reflux for 30 min, after completion of reaction aqueous sodium bicarbonate solution is added and extracted in ethyl acetate (4×25 mL) from the aqueous layer and concentrated in vacuo afforded 2-methyl 4H-benzo[d][1,3]oxazin-4-one compound (28) as pure product. To a stirred solution of 2-methyl-4-(phenylethynyl)benzenamine (26a, 207 mg, 1 mmol) with 2-methyl-4H-benzo[d][1,3]oxazin-4-one (28, 161 mg, 1 mmol) in acetic acid and reflux for 8 h. After completion of the reaction as indicated by TLC. The reaction mixture was quenched with NaHCO$_3$ and extracted in ethyl acetate (4×25 mL) from the ice cold aqueous layer and dried over anhydrous Na$_2$SO$_4$ afforded 2-methyl-3-(2-methyl-4-(phenylethynyl)phenyl)quinazolin-4(3H)-one (29a). Reaction of 2-methyl-3-(2-methyl-4-(phenylethynyl)phenyl)quinazolin-4(3H)-one (29a, 350 mg, 1 mmol) with 2,5-dihydroxy benzaldehyde (30c, 138 mg, 1 mmol) was taken in acetic acid Then the resulting mixture was stirred under reflux conditions for 8 h and then the reaction mixture was quenched with NaHCO$_3$ and extracted in ethyl acetate (4×25 mL) from the ice cold aqueous layer and dried over anhydrous Na$_2$SO$_4$. The resulting product (4c) was purified by column chromatography employing EtOAc/Hexane as an eluent.

Mp 170-172° C.; $^1$H NMR (CDCl$_3$+DMSO-d$_6$, 200 MHz) δ 8.26 (s, 1H), 8.02 (d, J=15.2 Hz, 1H), 7.88-7.62 (m, 3H), 7.57-7.33 (m, 6H), 7.26-7.16 (m, 3H), 7.03 (d, J=8.3 Hz, 1H), 6.81 (d, J=8.3 Hz, 1H), 6.52 (d, J=15.2 Hz, 1H), 1.82 (s, 3H); LRMS (ESI, m/z) 471 (M)$^+$.

Example 3

(E)-3-(4-((4-tert-butylphenyl)ethynyl)phenyl)-2-(2,4-dihydroxystyryl)quinazolin-4(3H)-one (5d)

4-iodo-2-methylbenzenamine 24 (233 mg, 1 mmol) on reaction with 1-tert-butyl-4-ethynylbenzene (25b, 158 mg, 1 mmol) by employing Sonagashira coupling conditions using Pd(PPh$_3$)$_4$ (69.3 mg, 0.06 equiv) as catalyst, CuI (22.8 mg, 0.12 equiv) as cocatalyst, butyl amine (261 mg, 3 equiv) as base and ether as solvent and kept the reaction for 6 h. After completion of the reaction as indicated by TLC and the reaction mixture is extracted into ether (4×25 mL) from the aqueous layer and concentrated in vacuo. The compound was further purified by column chromatography using 60-120 silica gel (ethyl acetate/hexane, 1:9) to obtain 4-((4-tert-butylphenyl)ethynyl)-2-methyl benzene amine (26b) as pure product. Anthranilic acid (27, 137 mg, 1 mmol) on reaction with acetic anhydride at 150° C. and reflux for 30 min, after completion of reaction aqueous sodium bicarbonate solution is added and extracted in ethyl acetate (4×25 mL) from the aqueous layer and concentrated in vacuo afforded 2-methyl 4H-benzo[d][1,3]oxazin-4-one compound (28) as pure product. To a stirred solution of 4-((4-tert-butylphenyl)ethynyl)-2-methylbenzenamine (26b, 263 mg, 1 mmol) with 2-methyl-4H-benzo[d][1,3]oxazin-4-one (28, 161 mg, 1 mmol) in acetic acid and reflux for 8 h After completion of the reaction as indicated by TLC. then the reaction mixture was quenched with NaHCO$_3$ and extracted in ethyl acetate (4×25 mL) from the ice cold aqueous layer and dried over anhydrous Na$_2$SO$_4$ afforded 3-(4-((4-tert-butylphenyl)ethynyl)-2-methylphenyl)-2-methylquinazolin-4(3H)-one (29b). Reaction of 3-(4-((4-tert-butylphenyl)ethynyl)-2-methylphenyl)-2-methyl quinazolin-4(3H)-one (29b, 406 mg, 1 mmol) with 2,4-dihydroxybenzaldehyde (30d, 138 mg, 1 mmol) was taken in acetic acid Then the resulting mixture was stirred under reflux conditions for 8 h and then the reaction mixture was quenched with NaHCO$_3$ and extracted in ethyl acetate (4×25 mL) from the ice cold aqueous layer and dried over anhydrous Na$_2$SO$_4$. The resulting product (5d) was purified by column chromatography employing EtOAc/Hexane as an eluent.

Mp 93-95° C.; $^1$H NMR (CDCl$_3$+DMSO-d$_6$, 200 MHz) δ 8.23 (d, J=15.9 Hz, 1H), 8.20 (s, 1H), 7.79-7.66 (m, 3H), 7.51-7.34 (m, 6H), 7.26 (s, 1H), 7.10 (d, J=8.3 Hz, 1H), 6.89 (d, J=8.3 Hz, 1H), 6.21 (d, J=15.2 Hz, 1H), 6.18 (s, 1H), 2.06 (s, 3H), 1.14 (s, 9H); LRMS (ESI, m/z) 527 (M)$^+$

Example 4

(E)-3-(4-((6-methoxynaphthalen-2-yl)ethynyl)-2-methylphenyl)-2-(3,4,5-trimethoxystyryl)quinazolin-4(3H)-one (61)

4-iodo-2-methylbenzenamine 24 (233 mg, 1 mmol) on reaction with 2-ethynyl-6-methoxynaphthalene (25c, 182 mg, 1 mmol) by employing Sonagashira coupling conditions using Pd(PPh$_3$)$_4$ (69.3 mg, 0.06 equiv) as catalyst, CuI (22.8 mg, 0.12 equiv) as cocatalyst, butyl amine (261 mg, 3 equiv) as base and ether as solvent and kept the reaction for 6 h. After completion of the reaction as indicated by TLC and the reaction mixture is extracted into ether (4×25 mL) from the aqueous layer and concentrated in vacuo. The compound was further purified by column chromatography using 60-120 silica gel (ethyl acetate/hexane, 1:9) to obtain 4-((6-methoxynaphthalen-2-yl) ethynyl)-2-methyl benzenamine (26c) as pure product. Anthranilic acid (27, 137 mg, 1 mmol) on reaction with acetic anhydride at 150° C. and reflux for 30 min, after completion of reaction aqueous sodium bicarbonate solution is added and extracted in ethyl acetate (4×25 mL) from the aqueous layer and concentrated in vacuo afforded 2-methyl-4H-benzo[d][1,3]oxazin-4-one compound (28) as pure product. To a stirred solution of 4-((6-methoxynaphthalen-2-yl)ethynyl)-2-methylbenzenamine (26c) with 2-methyl-4H-benzo[d][1,3]oxazin-4-one (28, 161 mg, 1 mmol) in acetic acid and reflux for 8 h After completion of the reaction as indicated by TLC. then the reaction mixture was quenched with NaHCO$_3$ and extracted in ethyl acetate (4×25 mL) from the ice cold aqueous layer and dried over anhydrous Na$_2$SO$_4$ afforded 3-(4-((6-methoxynaphthalen-2-yl)ethynyl)-2-methylphenyl)-2-methylquinazolin-4(3H)-one (29c). Reaction of 3-(4-((6-methoxynaphthalen-2-yl)ethynyl)-2-methylphenyl)-2-methylquinazolin-4(3H)-one (29c, 430 mg, 1 mmol) with 3,4,5-trimethoxybenzaldehyde (30l, 196 mg, 1 mmol) was taken in acetic acid Then the resulting mixture was stirred under reflux conditions for 8 h and then the reaction mixture was quenched with NaHCO$_3$ and extracted in ethyl acetate (4×25 mL) from the ice cold aqueous layer and dried over anhydrous Na$_2$SO$_4$. The resulting product (61) was purified by column chromatography employing EtOAc/Hexane as an eluent.

Mp 129-130° C.; $^1$H NMR (CDCl$_3$+DMSO-d$_6$, 200 MHz) δ 8.79 (t, J=8.5, 1H), 7.99 (s, 1H), 7.87 (d, J=14.5 Hz, 1H), 7.81-7.63 (m, 5H), 7.59-7.44 (m, 3H), 7.24 (d, J=10.2 Hz, 1H), 7.14 (dd, J=2.9, 7.7 Hz, 2H), 7.08 (s, 1H), 6.49 (s, 1H), 6.41 (d, J=15.3 Hz, 1H), 3.93 (s, 3H), 3.80 (s, 9H), 2.20 (s, 3H); LRMS (ESI, m/z) 609 (M)$^+$

Biological Activity

Some of biological activity studies were carried out at the National Cancer Institute (NCI), Maryland, USA.

Anticancer Activity:

The compounds were evaluated for anticancer activity against sixty human cancer cells derived from nine cancer types (leukemia cell line, non-small-cell lung cell line, colon cell line, CNS cell line, melanoma cell line, ovarian cell line, prostate cell line, renal cell line and breast cancer cell line) as shown in Table 1. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth.

TABLE 1

The GI$_{50}$ (the concentration needed to reduce the growth of treated cells to half that of untreated cells) values for compounds 4b, 4c, 5d, and 6l in sixty cancer cell lines

| Cancer panel/ cell line | Growth Inhibition GI$_{50}$ (μM) | | | |
|---|---|---|---|---|
| | NSC: 754027 (4b) | NSC: 754031 (4c) | NSC753534 (5d) | NSC;754032 (6l) |
| Leukemia | | | | |
| CCRF-CEM | 3.26 | 1.54 | 3.85 | —$^b$ |
| HL-60(TB) | 1.66 | 0.634 | —$^a$ | 0.686 |
| K-562 | 2.00 | 1.42 | 3.28 | 0.882 |
| MOLT-4 | 2.36 | 1.14 | 2.45 | 4.66 |
| SR | 2.45 | 1.10 | 2.45 | 0.395 |
| RPMI-8226 | 2.33 | 1.26 | 3.10 | 0.821 |
| Non-small lung | | | | |
| A549/ATCC | 3.14 | 1.28 | 2.83 | —$^b$ |
| EKVX | 2.43 | 1.24 | 3.67 | 24.1 |
| HOP-62 | 13.1 | 1.71 | 5.88 | —$^b$ |
| HOP-92 | 2.50 | 1.54 | 2.82 | —$^b$ |
| NCI-H226 | 3.99 | 1.52 | 2.17 | —$^b$ |
| NCI-H23 | 3.62 | 1.48 | 2.42 | 40.5 |
| NCI-H322M | 2.93 | 1.62 | 6.09 | —$^b$ |
| NCI-H460 | 2.22 | 1.57 | 1.82 | 2.48 |
| NCI-H522 | 2.26 | 1.29 | 1.83 | —$^b$ |
| Colon | | | | |
| COLO 205 | 1.99 | 1.48 | 3.02 | 6.96 |
| HCC-2998 | 2.35 | 1.36 | 1.93 | —$^b$ |
| HCT-116 | 2.66 | 1.46 | 2.89 | 3.53 |
| HCT-15 | 2.50 | 1.03 | 2.74 | 1.22 |
| HT29 | 3.33 | 1.95 | 2.08 | 3.41 |
| KM12 | 3.24 | 1.65 | 3.33 | 4.30 |
| SW-620 | 4.08 | 1.71 | 1.81 | 17.2 |
| CNS | | | | |
| SF-268 | 4.56 | 1.31 | 4.82 | —$^b$ |
| SF-295 | 2.85 | 1.35 | 3.83 | —$^b$ |
| SF-539 | 5.65 | 1.60 | 4.37 | —$^b$ |
| SNB-19 | 6.91 | 1.62 | 7.90 | —$^b$ |
| SNB-75 | 3.66 | 1.30 | 1.87 | —$^b$ |
| U251 | 4.33 | 1.45 | 2.11 | 7.40 |
| Ovarian | | | | |
| IGROV1 | 20.6 | 2.45 | 7.48 | —$^b$ |
| OVCAR-3 | 3.60 | 1.49 | 2.23 | 19.3 |
| OVCAR-4 | 3.17 | 2.40 | 3.15 | —$^b$ |
| OVCAR-5 | 4.59 | 1.39 | 4.25 | —$^b$ |
| OVCAR-8 | 3.98 | 1.94 | 3.55 | —$^b$ |
| NCI/ADR-RES | 3.09 | 2.06 | 3.17 | —$^b$ |
| SK-OV-3 | 9.91 | 1.83 | 10.9 | —$^b$ |
| Renal | | | | |
| 786-0 | 3.65 | 1.74 | 5.08 | —$^b$ |
| A498 | 1.56 | 0.370 | 2.98 | —$^b$ |
| ACHN | 2.46 | 1.44 | 3.26 | —$^b$ |
| CAKI-1 | 3.30 | 2.15 | 2.87 | 4.91 |
| SN12C | 3.77 | 1.62 | 1.88 | —$^b$ |
| TK-10 | 2.62 | 2.03 | 3.82 | —$^b$ |
| UO-31 | 2.06 | 1.16 | 2.63 | —$^b$ |
| RXF 393 | —$^a$ | | 1.88 | —$^b$ |
| Prostate | | | | |
| PC-3 | 3.24 | 2.19 | 3.67 | —$^b$ |
| DU-145 | 4.87 | 0.419 | 3.42 | —$^b$ |
| Breast | | | | |
| MCF7 | 2.72 | 1.45 | 2.39 | 63.8 |
| MDA-MB-231/ATCC | 3.89 | 1.56 | 3.06 | 37.0 |
| HS 578T | 2.48 | 1.54 | 2.20 | —$^b$ |
| BT-549 | —$^a$ | —$^a$ | 8.60 | —$^a$ |

TABLE 1-continued

The GI50 (the concentration needed to reduce the growth of treated cells to half that of untreated cells) values for compounds 4b, 4c, 5d, and 6l in sixty cancer cell lines

| Cancer panel/ cell line | Growth Inhibition GI$_{50}$ (μM) | | | |
|---|---|---|---|---|
| | NSC: 754027 (4b) | NSC: 754031 (4c) | NSC753534 (5d) | NSC;754032 (6l) |
| T-47D | 2.02 | 1.14 | 3.85 | —[b] |
| MDA-MB-468 | 3.78 | 1.61 | 2.20 | 3.80 |
| Melanoma | | | | |
| LOX IMVI | 2.78 | 1.37 | 1.49 | 5.96 |
| MALME-3M | 2.12 | 1.50 | 8.42 | 42.6 |
| M14 | 3.26 | 1.54 | 5.91 | 12.7 |
| MDA-MB-435 | 2.82 | 1.67 | 3.08 | —[b] |
| SK-MEL-2 | 1.93 | 1.40 | 3.52 | —[b] |
| SK-MEL-28 | 4.54 | 1.53 | 2.42 | —[b] |
| SK-MEL-5 | 1.77 | 1.35 | 1.77 | 1.85 |
| UACC-257 | 4.18 | 1.56 | 6.91 | 6.24 |
| UACC-62 | 3.48 | 1.52 | 3.52 | 2.19 |

—[a] not done on that cell line;
—[b] means GI$_{50}$ values not attained at the concentrations used.

TABLE 2

The mean graph midpoint values (MG_MID) of Log$_{10}$GI$_{50}$ (log values of concentration in mol/L causing 50% inhibition of net cell growth) values for compounds 4b, 4c, 5d and 6l in sixty cancer cell lines.

| Cancer cell lines Log$_{10}$GI$_{50}$ | 4b | 4c | 5d | 6l |
|---|---|---|---|---|
| Leukemia | −5.64 | −5.94 | −5.53 | −5.67 |
| Non-small cell lung | −5.47 | −5.83 | −5.53 | −4.32 |
| Colon | −5.55 | −5.83 | −5.60 | −5.16 |
| CNS | −5.35 | −5.85 | −5.43 | −4.18 |
| Melanoma | −5.54 | −5.83 | −5.45 | −4.79 |
| Ovarian | −5.33 | −5.72 | −5.34 | −4.10 |
| Renal | −5.52 | −5.86 | −5.54 | −4.16 |
| Prostate | −5.40 | −6.17 | −5.45 | −4.00 |
| Breast | −5.54 | −5.84 | −5.49 | −4.51 |

TABLE 3

The mean graph midpoint values (MG_MID) of Log$_{10}$LC$_{50}$ values (log value of the concentration of compounds leading to 50% net cell death) for compounds 4b, 4c, 5d and 6l in sixty cancer cell lines.

| Cancer cell lines Log$_{10}$ LC$_{50}$ | 4b | 4c | 5d | 6l |
|---|---|---|---|---|
| Leukemia | >−4.00 | −4.40 | >−4.00 | >−4.00 |
| Non-small cell lung | −4.04 | −4.91 | −4.51 | >−4.00 |
| Colon | −4.15 | −5.23 | −5.41 | >−4.00 |
| CNS | >−4.00 | −5.15 | −4.35 | >−4.00 |
| Melanoma | −4.16 | −5.22 | −4.02 | >−4.00 |
| Ovarian | >−4.00 | −4.61 | −4.19 | >−4.00 |
| Renal | >−4.00 | −4.93 | −4.5 | >−4.00 |
| Prostate | >−4.00 | −4.68 | −4.24 | >−4.00 |
| Breast | >−4.00 | −4.66 | −4.25 | >−4.00 |

TABLE 4

The mean graph midpoint values (MG_MID) of log$_{10}$ TGI (log value of concentration of the compound resulting in total inhibition of net cell growth) for compounds 4b, 4c, 5d and 6l in sixty cancer cell lines.

| Cancer cell lines Log$_{10}$TGI$_{50}$ | 4b | 4c | 5d | 6l |
|---|---|---|---|---|
| Leukemia | −4.49 | −5.38 | −4.72 | >−4.00 |
| Non-small cell lung | −4.32 | −5.44 | −4.45 | >−4.00 |
| Colon | −4.83 | −5.53 | −5.15 | >−4.00 |
| CNS | −4.21 | −5.50 | −4.83 | >−4.00 |
| Melanoma | −4.79 | −5.52 | −4.96 | >−4.00 |
| Ovarian | −4.23 | −5.31 | −4.77 | >−4.00 |
| Renal | −4.65 | −5.43 | −4.97 | >−4.00 |
| Prostate | >−4.00 | −5.43 | −4.83 | >−4.00 |
| Breast | −4.58 | −5.39 | −4.93 | >−4.00 |

ADVANTAGES OF THE INVENTION

1. The present invention provides 3-arylethynyl substituted quinazolinone compounds of general formula A.
2. It also provides a process for the preparation of 3-aryl-ethynyl substituted quinazolinone compounds of general formula A.

We claim:

1. A 3-Arylethynyl substituted quinazolinone compound of formula A:

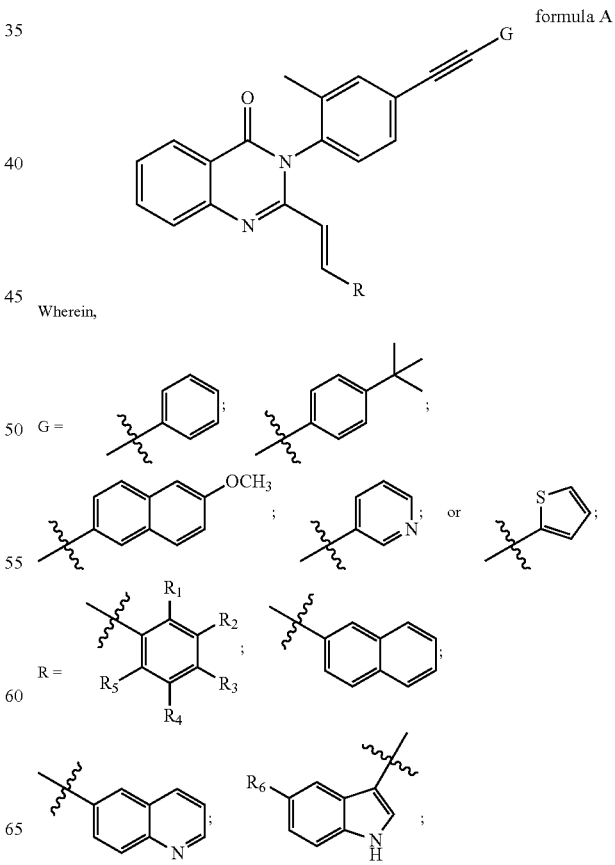

Wherein,

G =

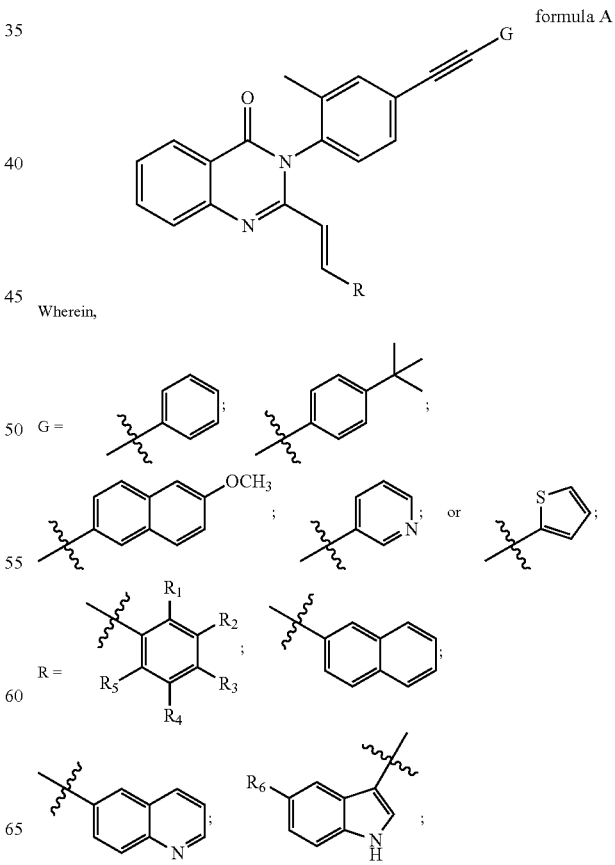

-continued
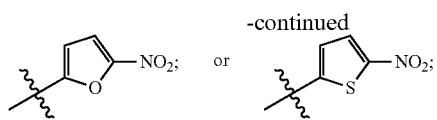 or
R$_1$=H, OH, or OCH$_3$;
R$_2$=H, OH, CH$_3$, OCH$_3$, or NO$_2$; R$_3$=H, OH, OCH$_3$, F, or Cl; or R$_2$ and R$_3$ taken together form the group —OCH$_2$O—:
R$_4$=H, OH, CH$_3$, or OCH$_3$;
R$_5$=H, OH, CH$_3$, or OCH$_3$; and
R$_6$=H, or OCH$_3$.
2. A 3-Arylethynyl substituted quinazolinone compound of formula A as claimed in claim 1, wherein the structural formula of the compound is:
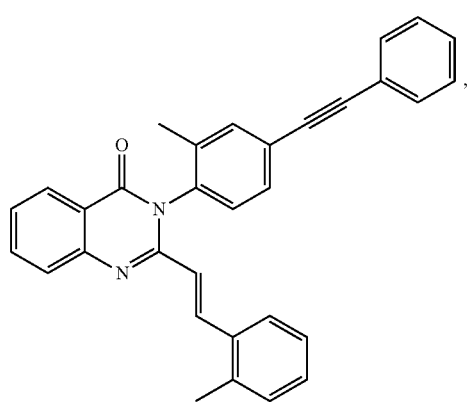
4a
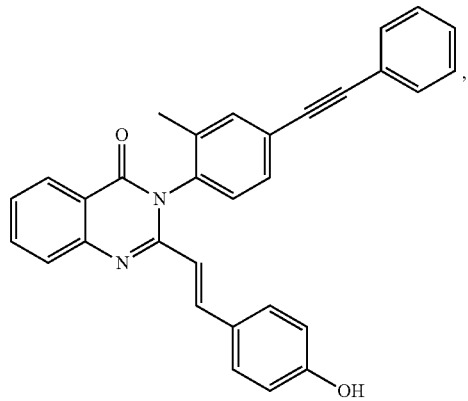
4b
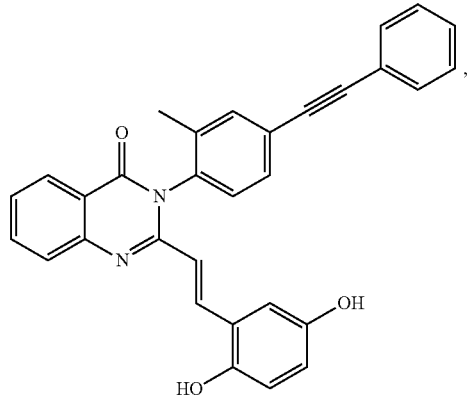
4c
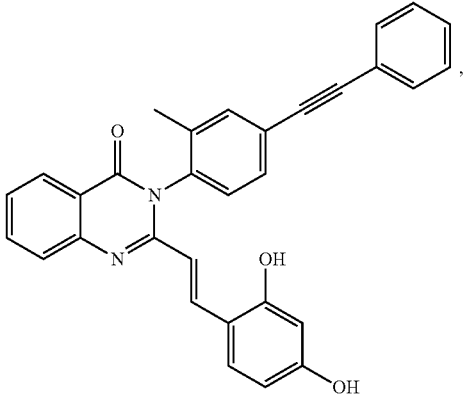
4d
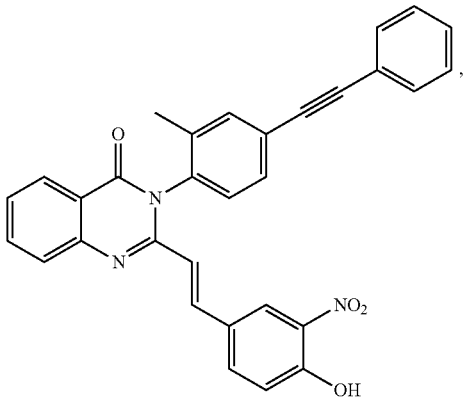
4e
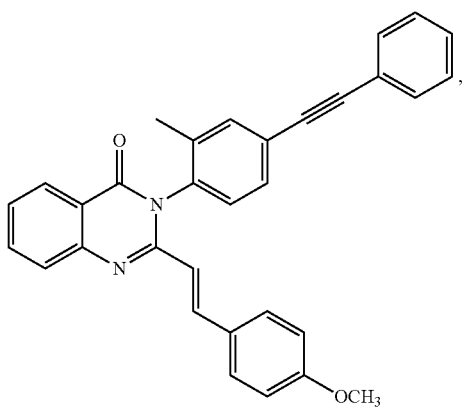
4f
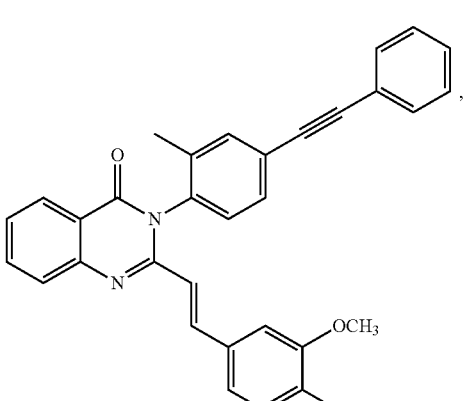
4g

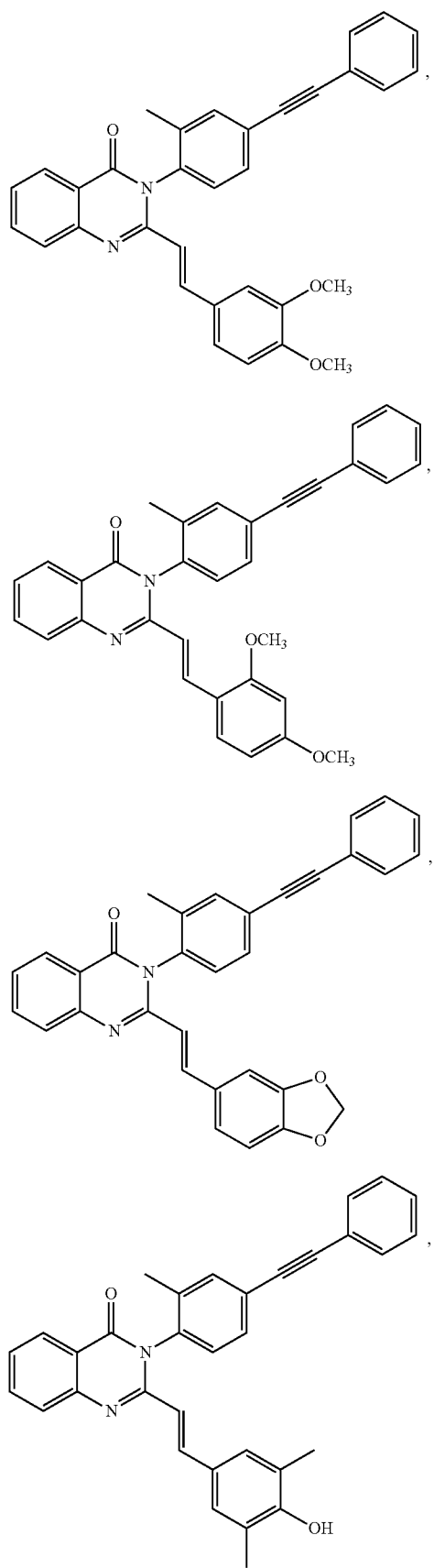
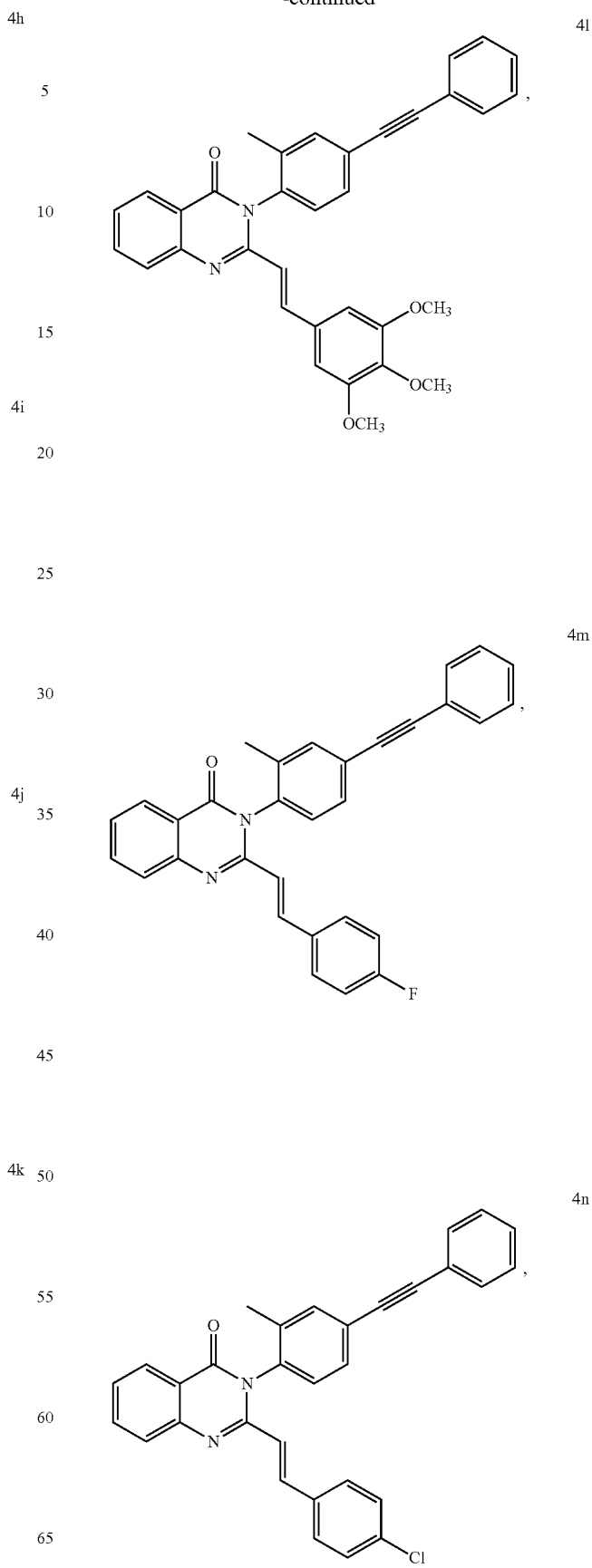

5a
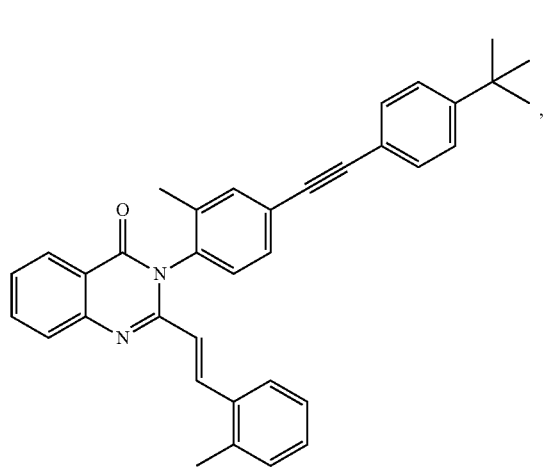
5d
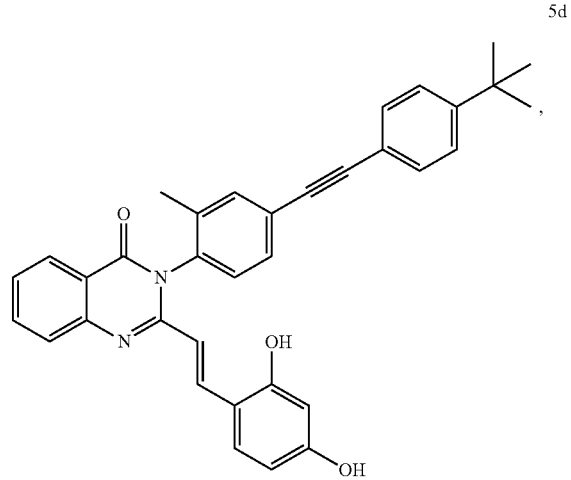
5b
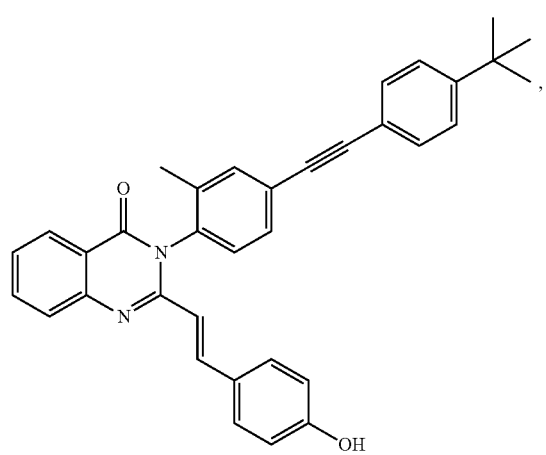
5e
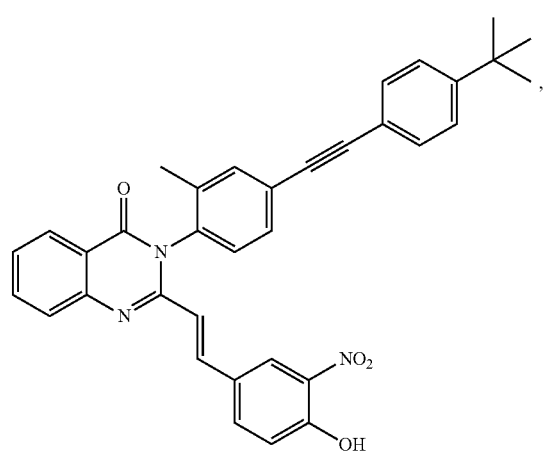
5c
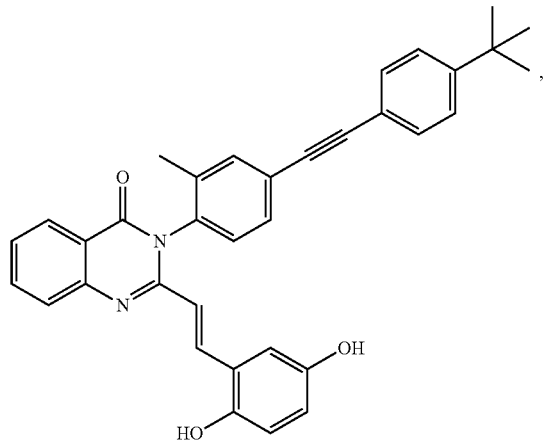
5f
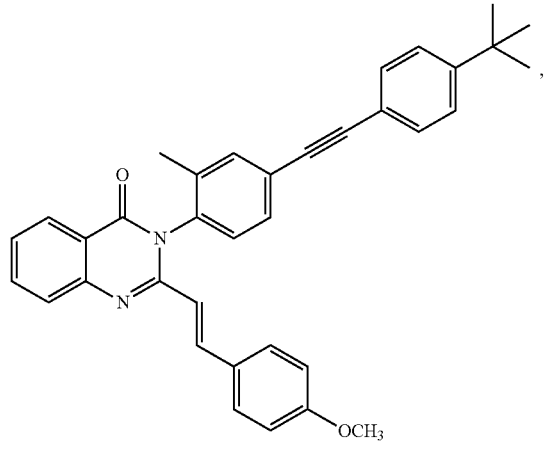

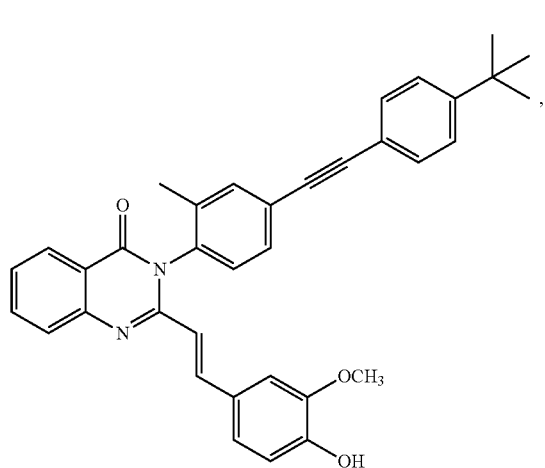
5g
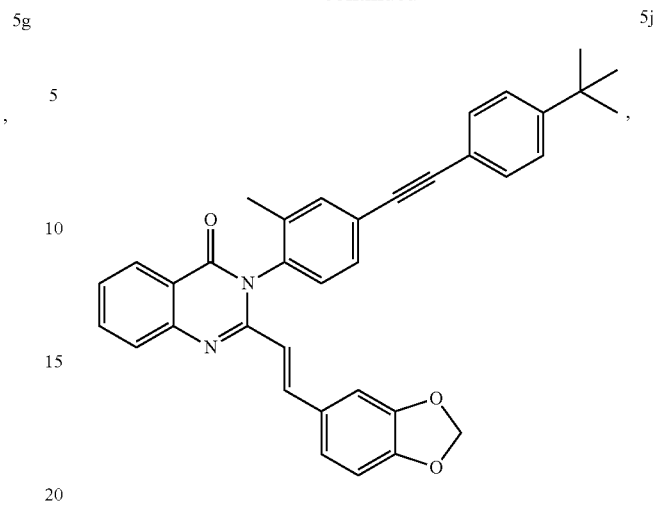
5j
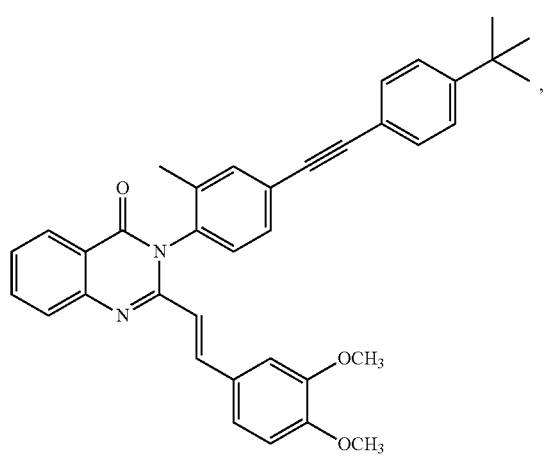
5h
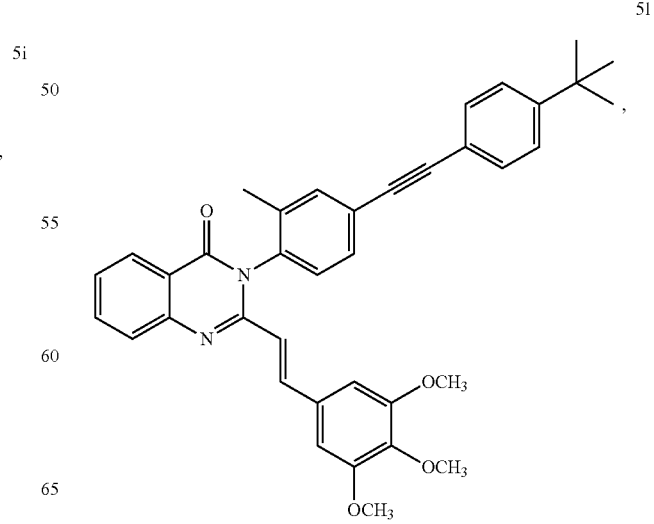
5k
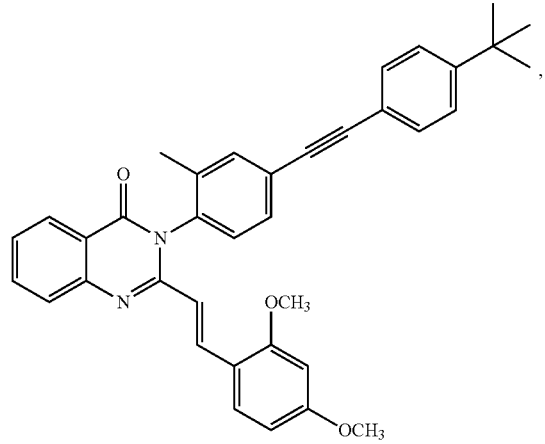
5i
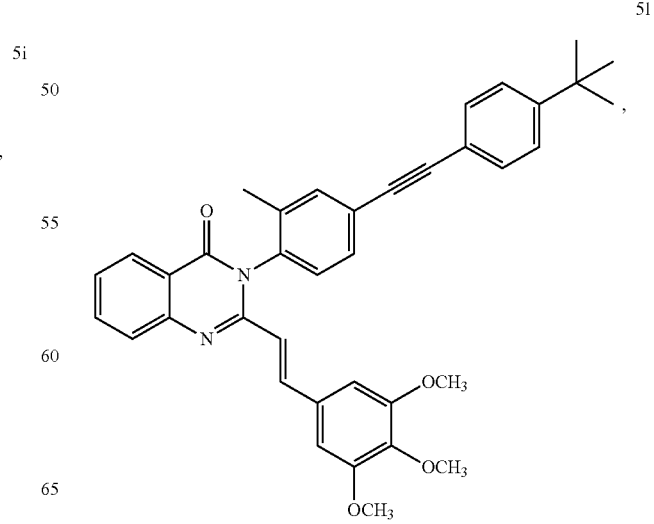
5l

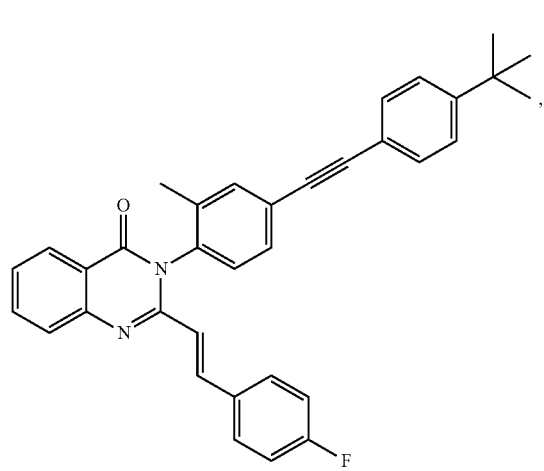
5m
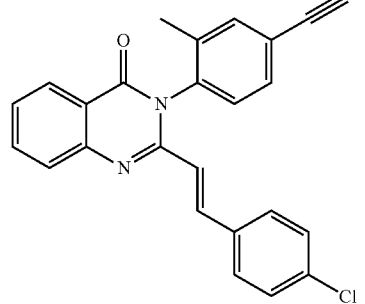
5n
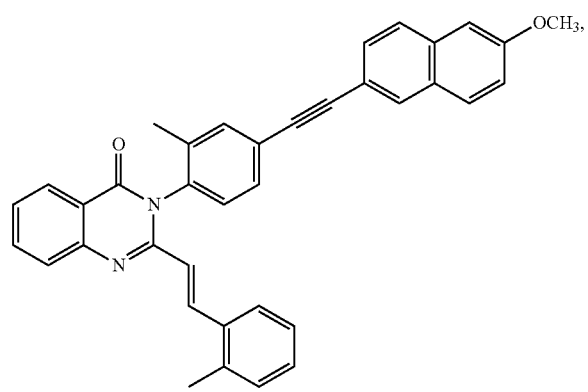
6a
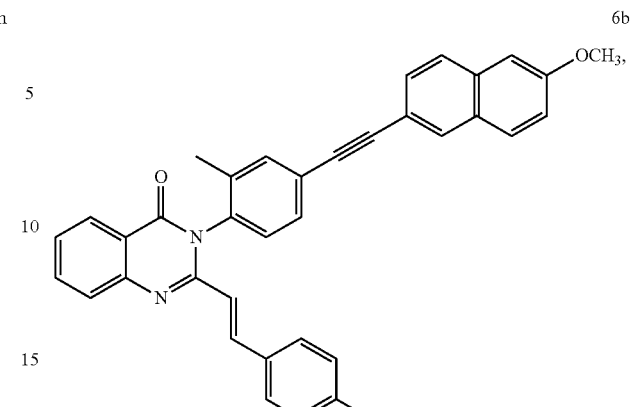
6b
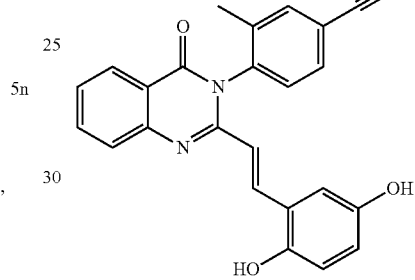
6c
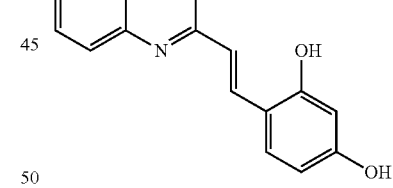
6d
6e

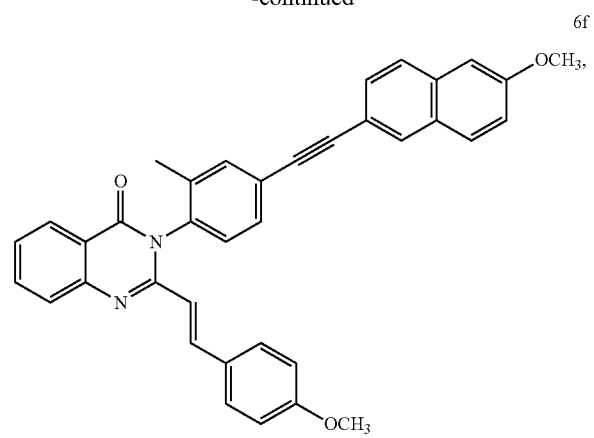
6f
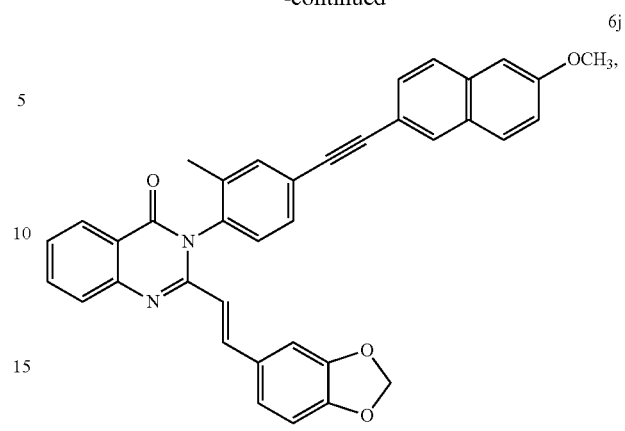
6j
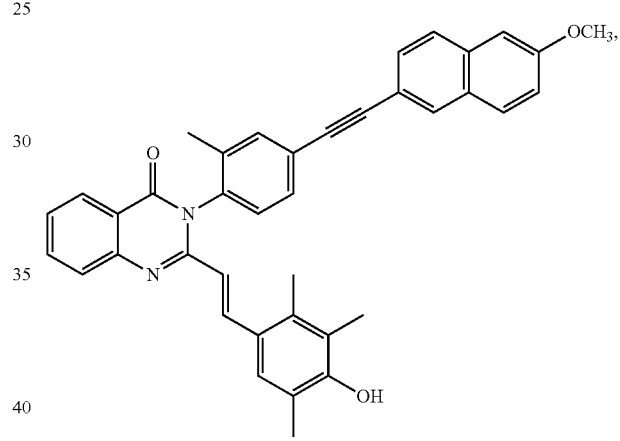
6k
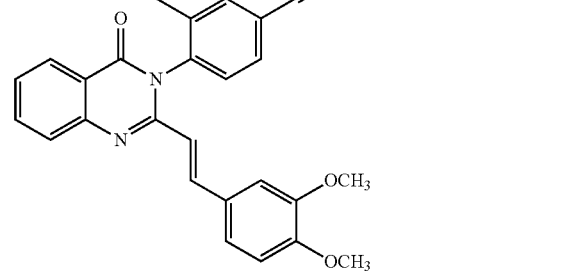
6g
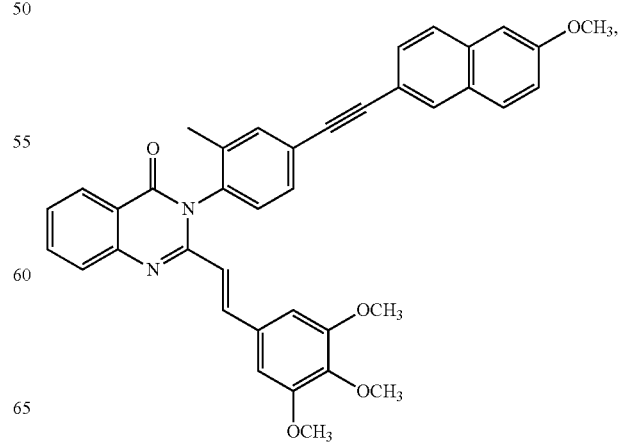
6l

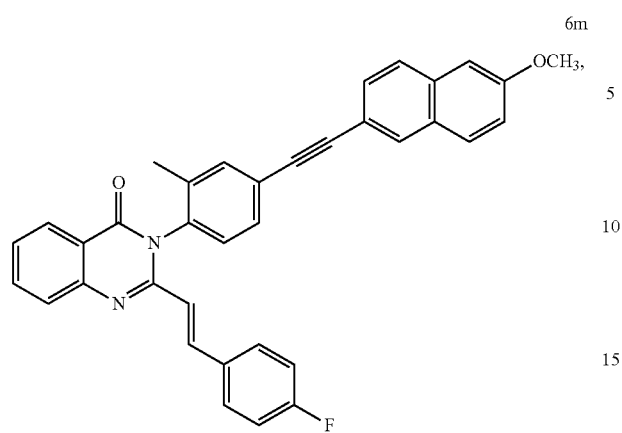
6m
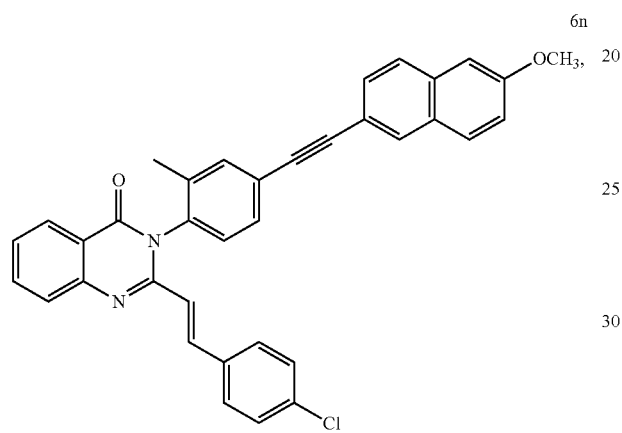
6n
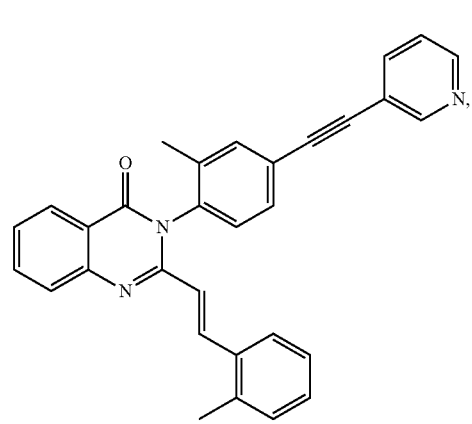
7a
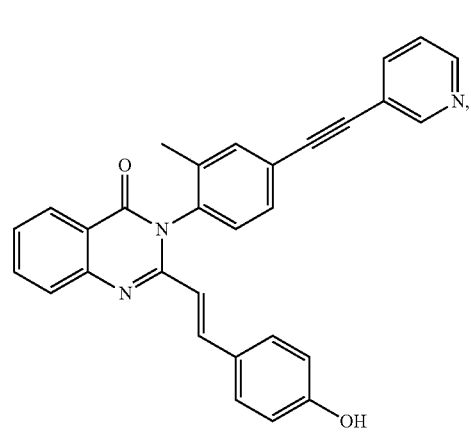
7b
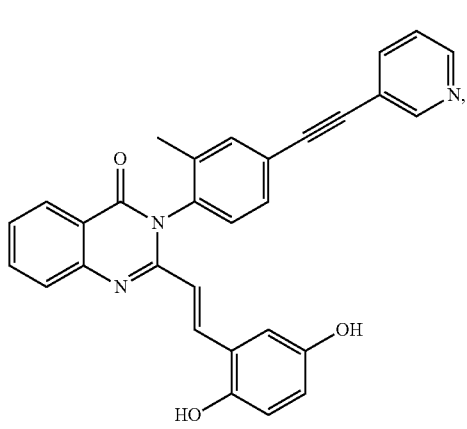
7c
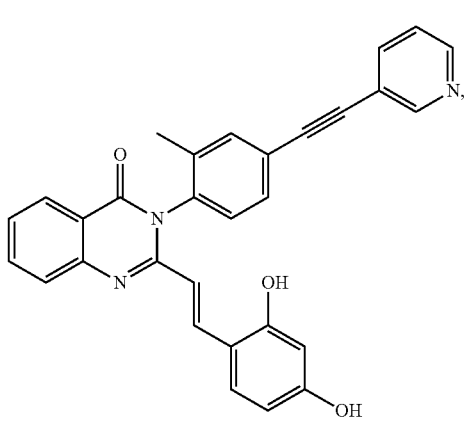
7d
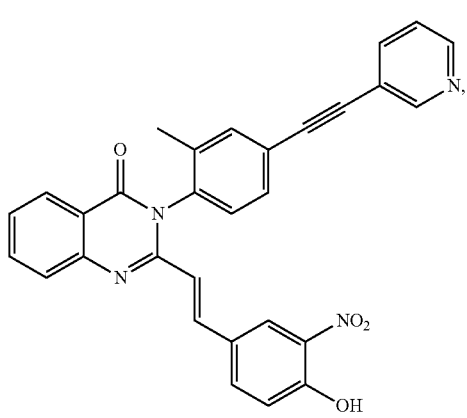
7e
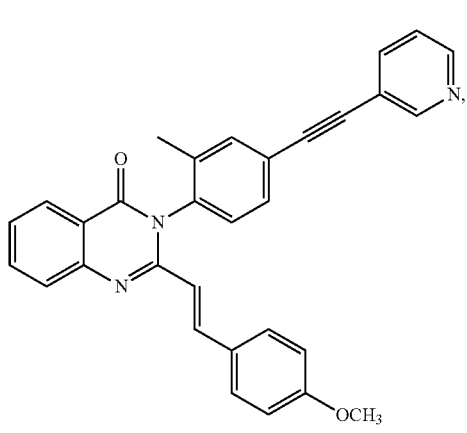
7f -continued
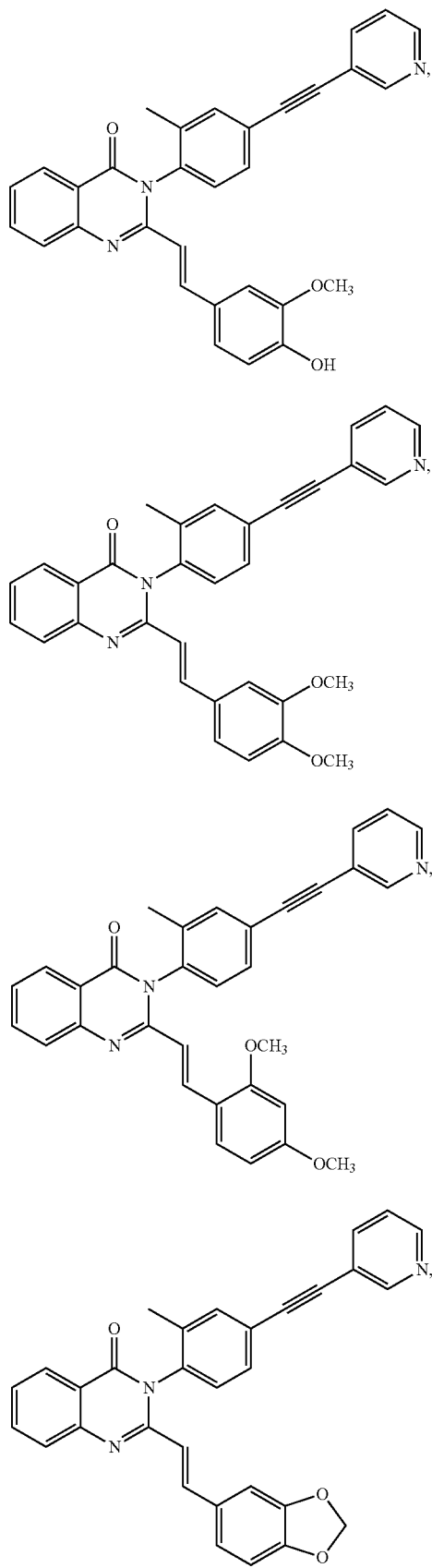
7g
7h
7i
7j
-continued
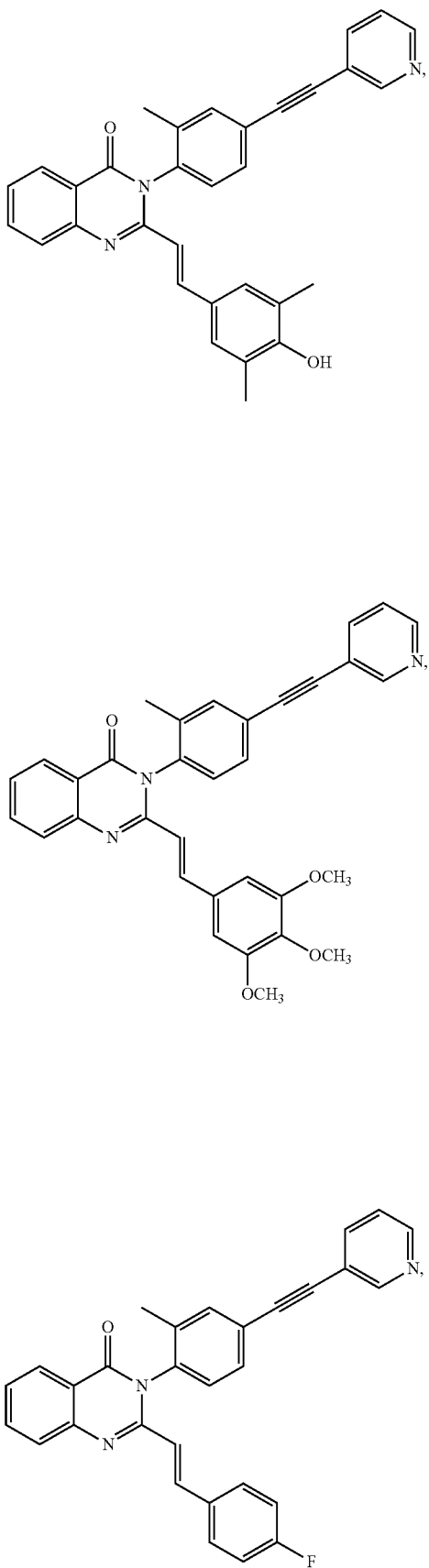
7k
7l
7m

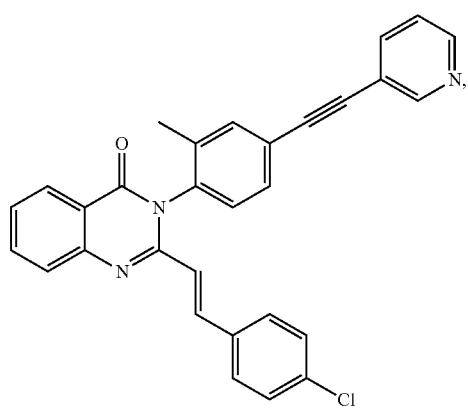 7n
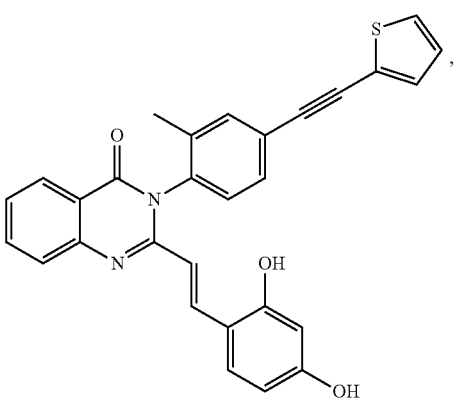 8d
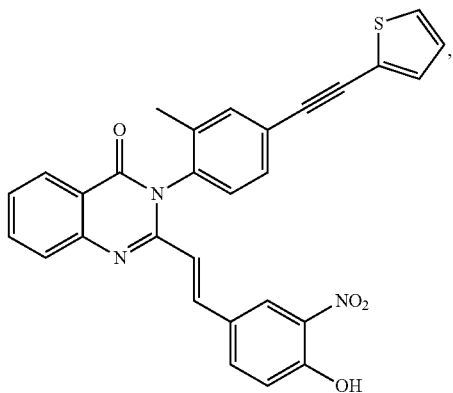 8e
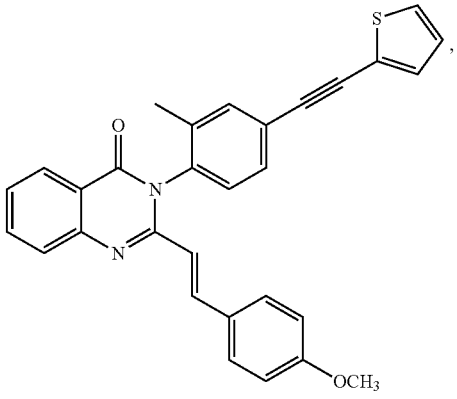 8f
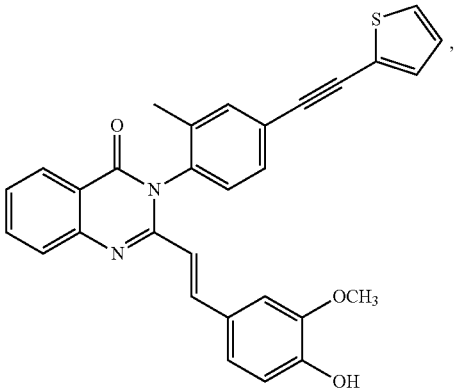 8g

8h
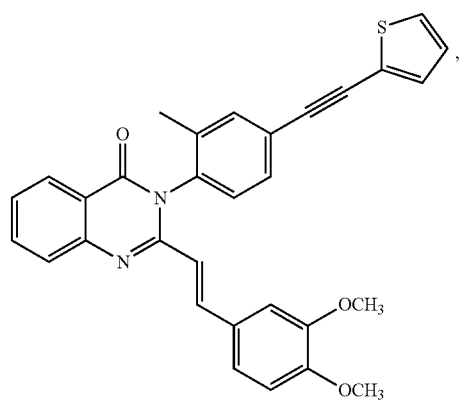
8i
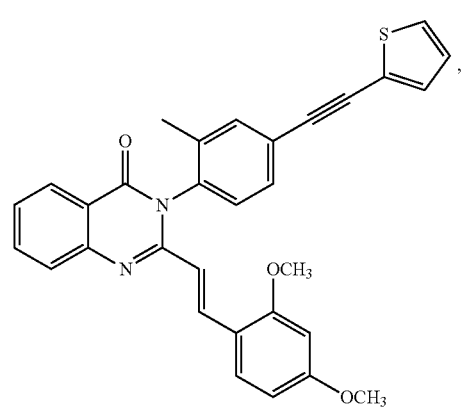
8j
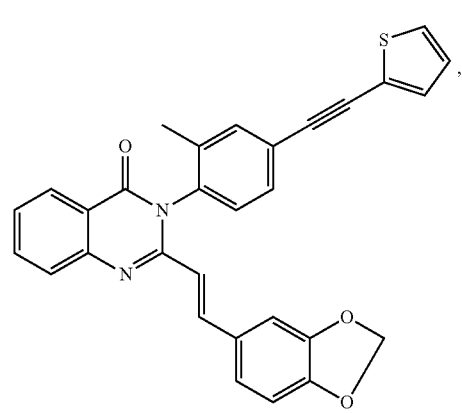
8k
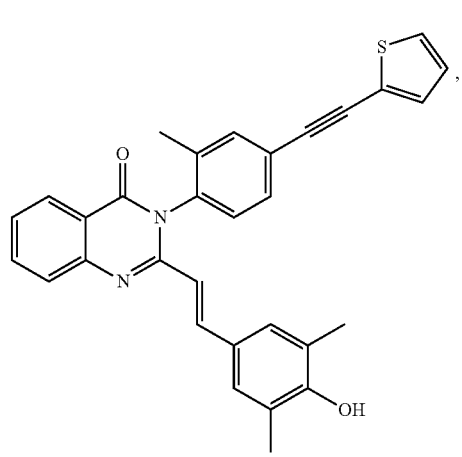
8l
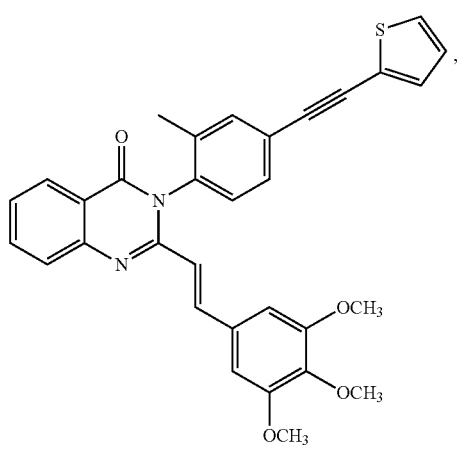
8m
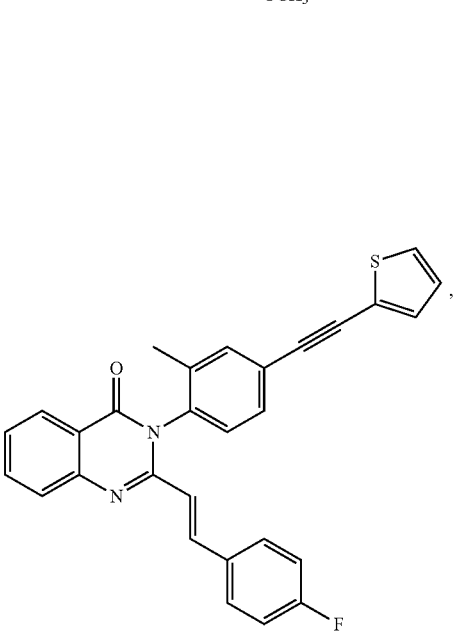
8n
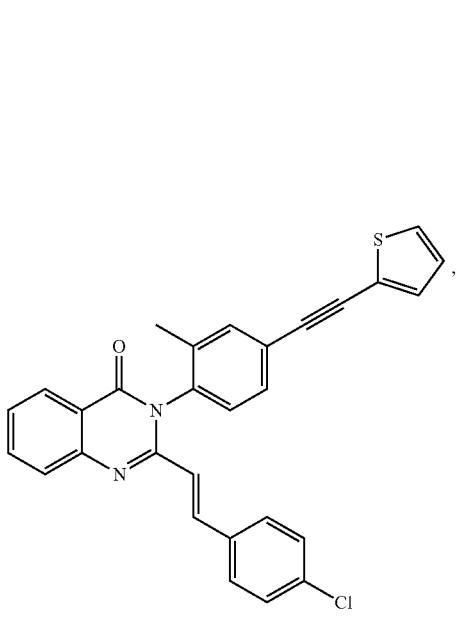

-continued
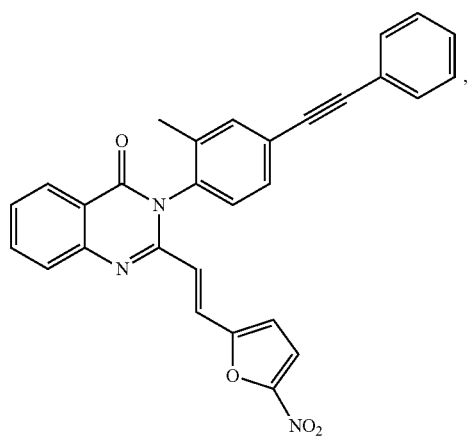
9a
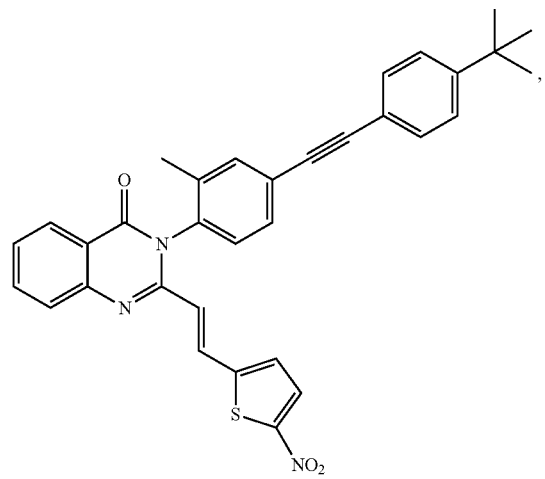
10b
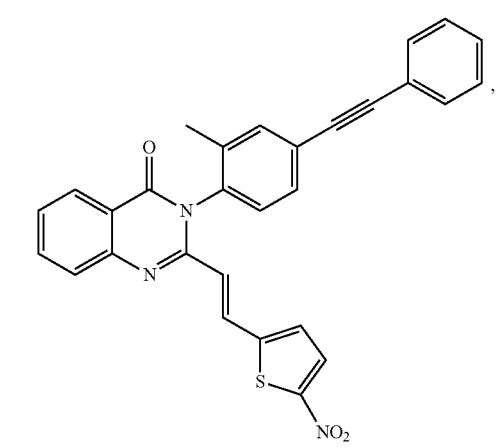
9b
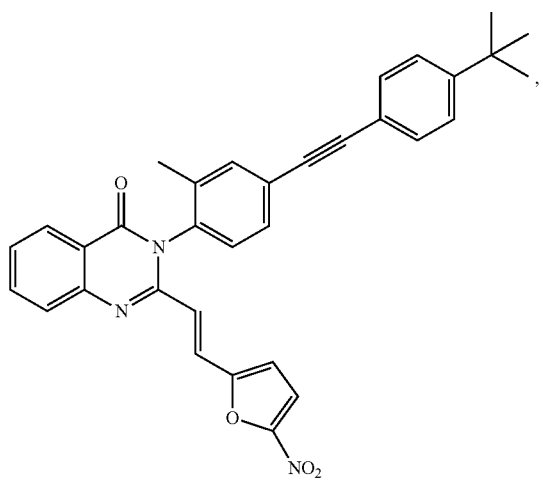
10a
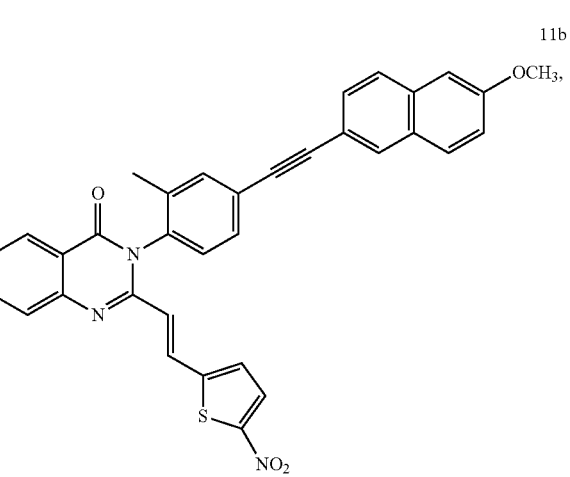
11b

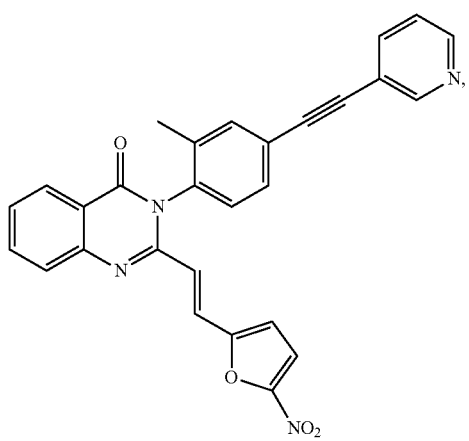
12a
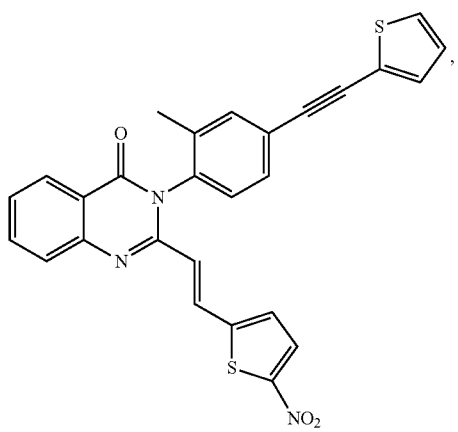
13b
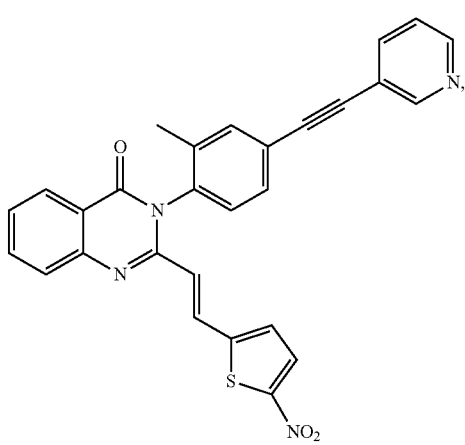
12b
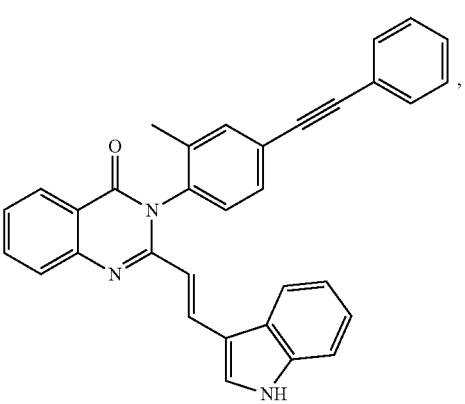
14a
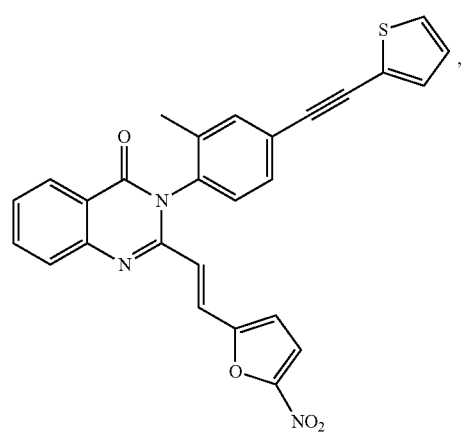
13a
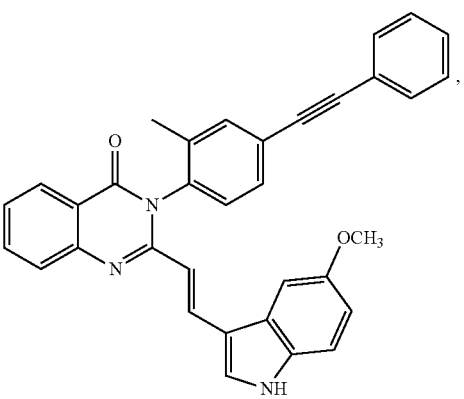
14b

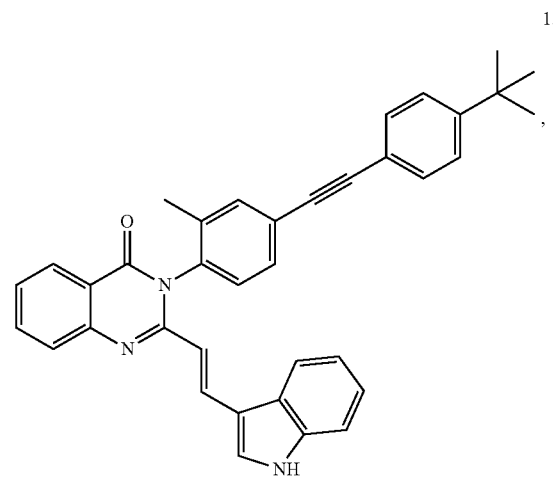
15a
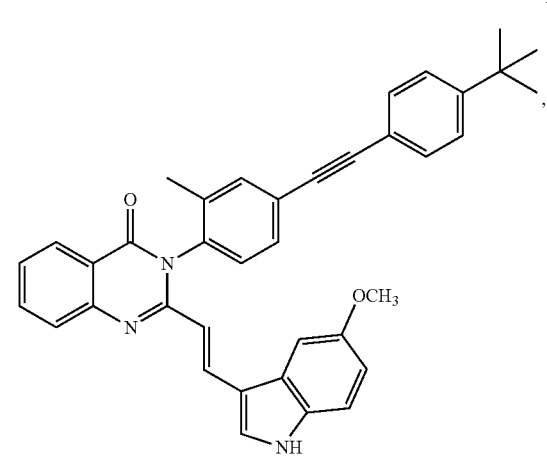
15b
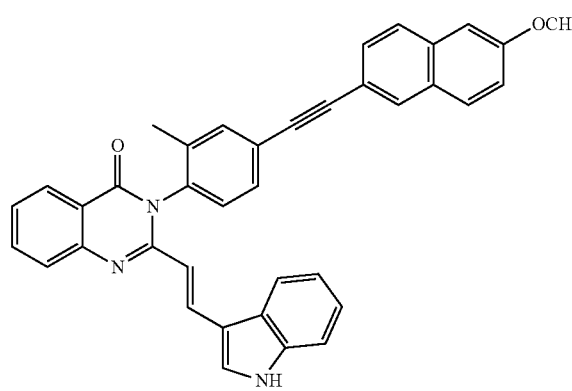
16a
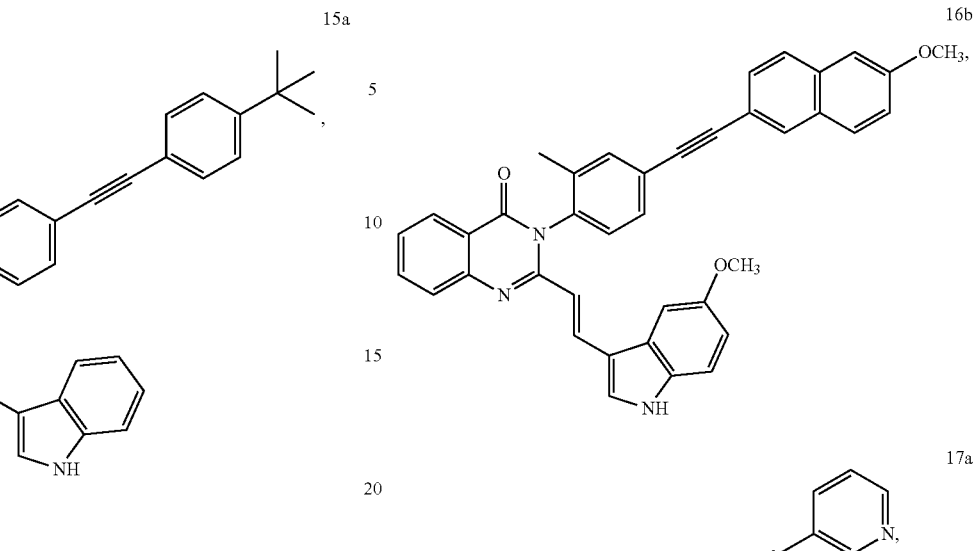
16b
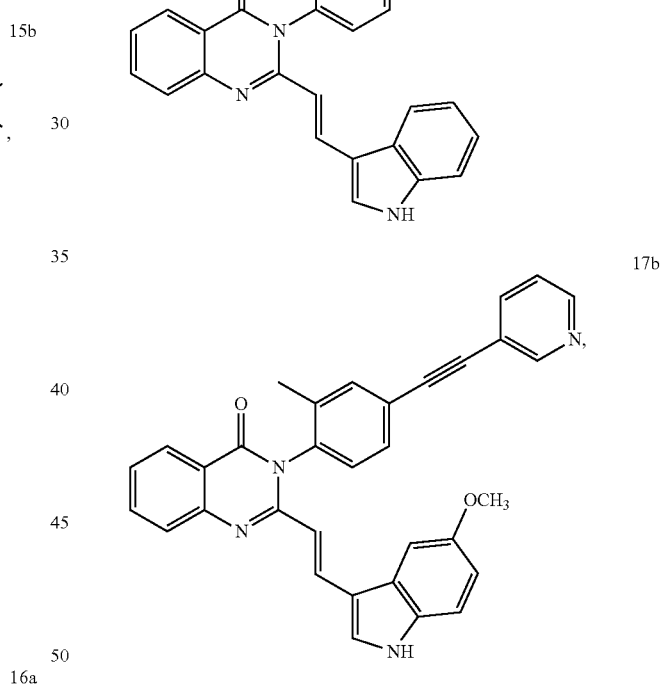
17a
17b
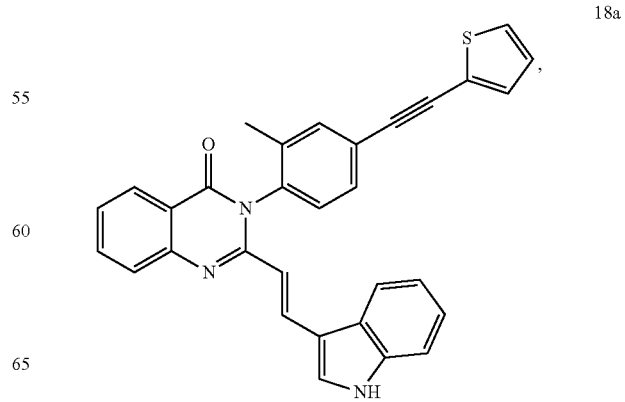
18a

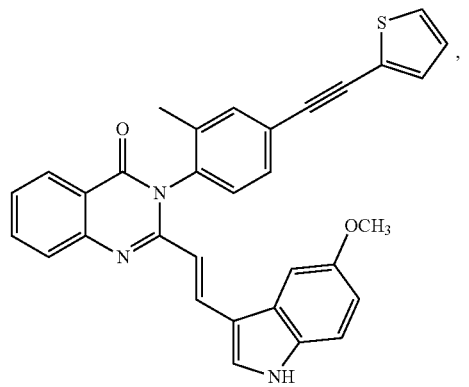
18b
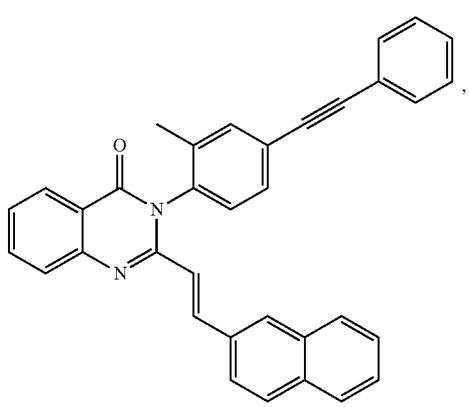
19a
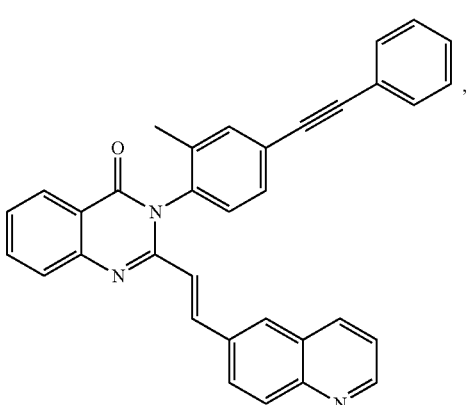
19b
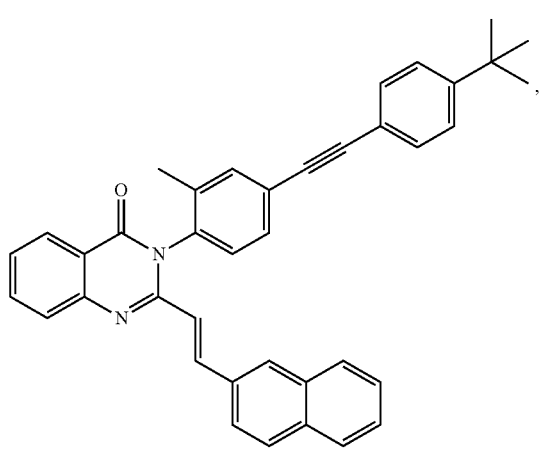
20a
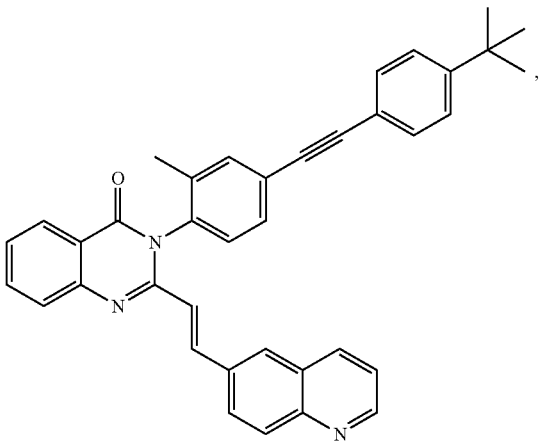
20b
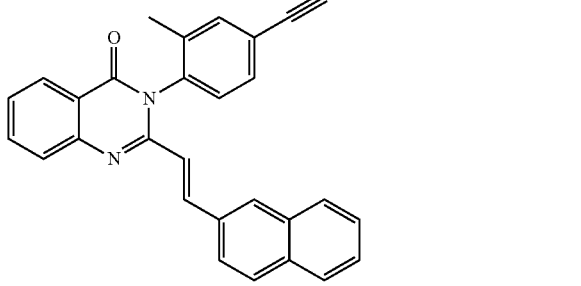
21a
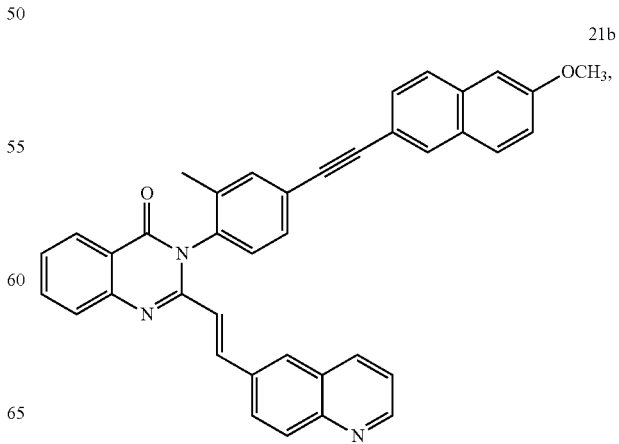
21b -continued

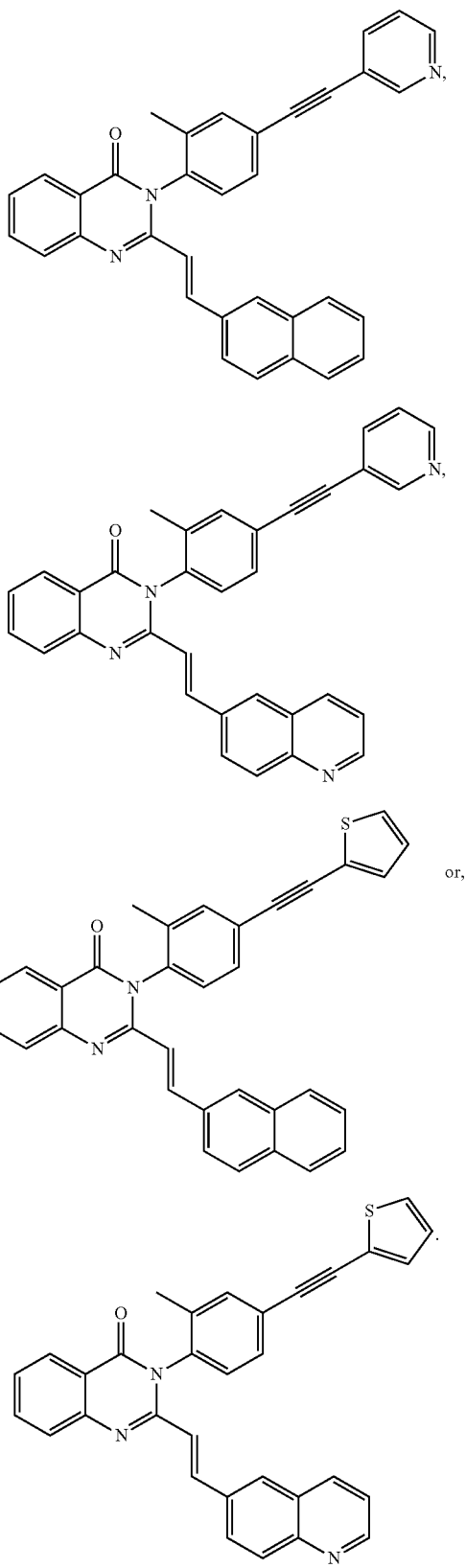

3. A method for treating leukemia, small cell lung cancer, colon cancer, CNS cancer, renal cancer, prostate cancer, ovarian cancer, breast cancer or melanoma in a patient comprising administering to said patient a 3-arylethynyl substituted quinazoline compound of formula A as claimed in claim 1.

4. The method of claim 3 wherein the compound of formula A is

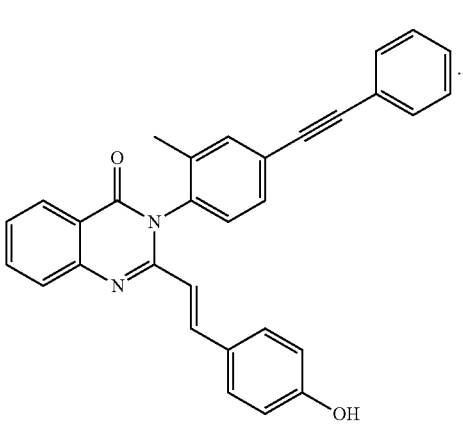

5. The method of claim 3 wherein the compound of formula A is

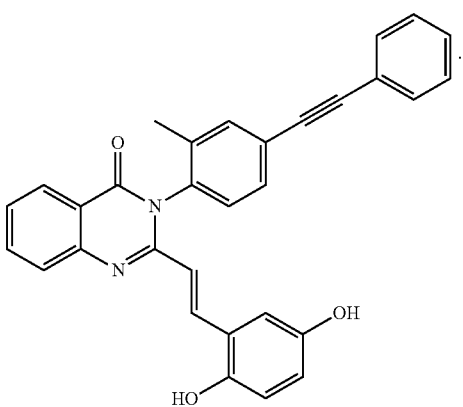

6. The method of claim 3 wherein the compound of formula A is

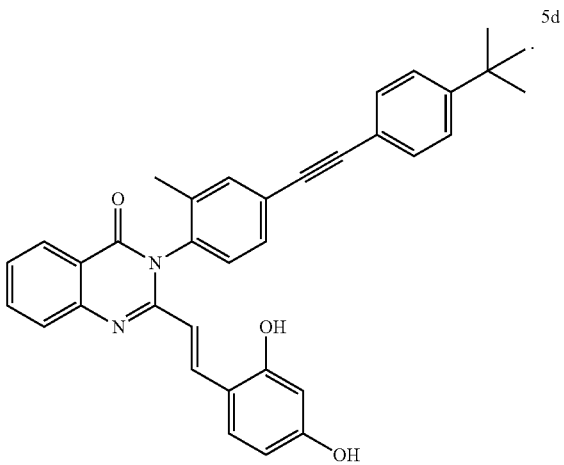 [SMILES: Cc1cc(C#Cc2ccc(C(C)(C)C)cc2)ccc1-n1c(/C=C/c2ccc(O)cc2O)nc2ccccc2c1=O]

7. The method of claim 3 wherein the compound of formula A is

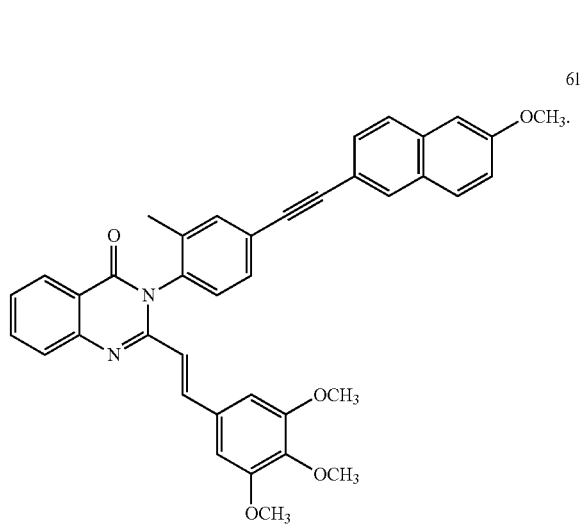 [SMILES: COc1ccc2cc(C#Cc3ccc(-n4c(/C=C/c5cc(OC)c(OC)c(OC)c5)nc5ccccc5c4=O)c(C)c3)ccc2c1]
61

8. A process for the preparation of 3-arylethynyl substituted quinaiolinone compounds of formula A according of claim 1 comprising the steps of:

i. reacting 4-iodo-2-methylbenzenamine (24) with a substituted aryl or heteroaryl ethynyl compound of formula 25-a, 25-h, 25-c, 25-d, or 25-e under Sonagashira coupling conditions using Pd(PPh$_3$)$_4$ as a catalyst, CuI as a cocatalyst, butyl amine as a base and ether as a solvent a for 6-8 hours to give a 2-methyl-4-(phenylethynyl)benzenamine compound of formula 26-a, 26-b, 26-c, 26-d, or 26-e;

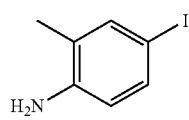
24

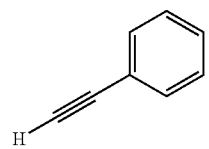
25a

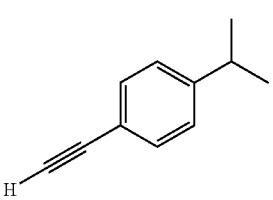
25b

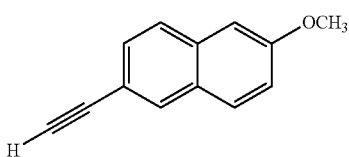
25c

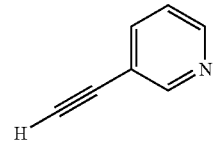
25d

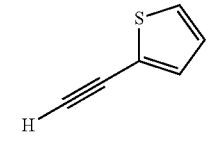
25e

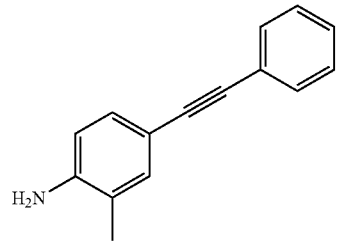
26a

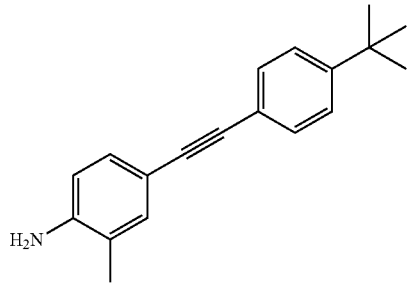
26b

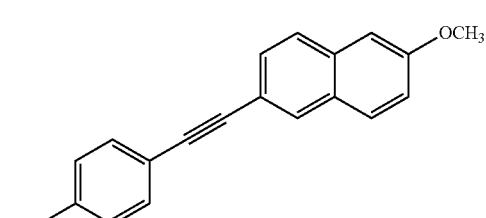
26c

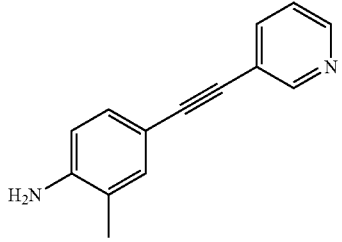
26d

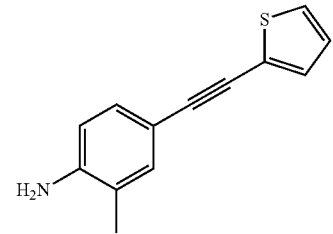
26e ii. reacting an anthranilic acid with an acetic anhydride at a temperature in the range of 150-155° C. for period in the range of 30-45 min to give a 2-methyl-4H-benzo[d][1,3]oxazin-4-one compound (28);

28

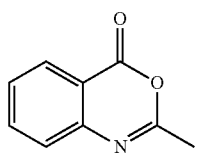

iii. mixing a 2-methyl-4-(phenylethynyl)benzenamine compound of formula 26-a, 26-b, 26-c, 26-d, or 26-e as obtained in step (i) with 2-methyl-4H-benzo[d][1,3]oxazin-4-one as obtained in step (ii) in acetic acid and heating the mixture under reflux conditions for 8-10 hours to give a 2-methyl-3-(2-methyl-4-(phenylethynyl)phenyl)quinazolin-4(3H)-one compound of formula 29-a, 29-b, 29-c, 29-d, or 29-e;

29a

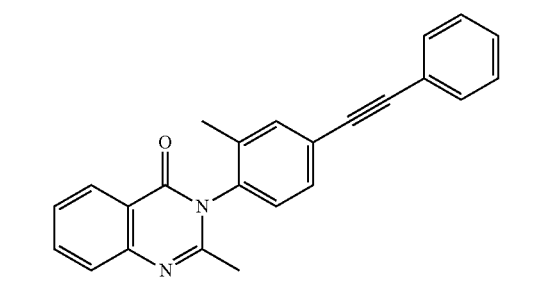

29b

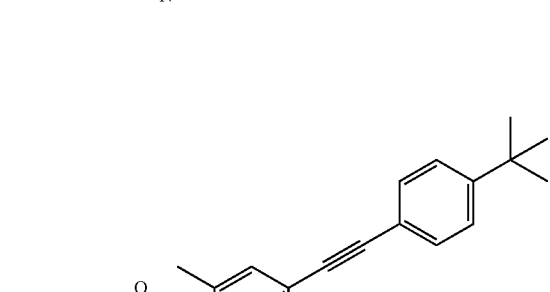

29c

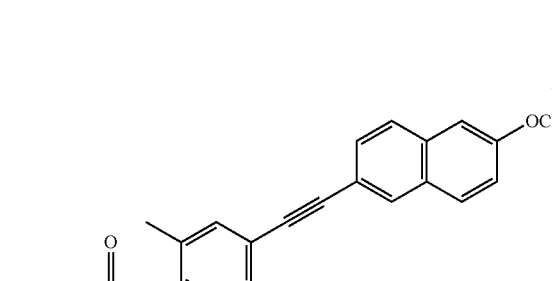

29d

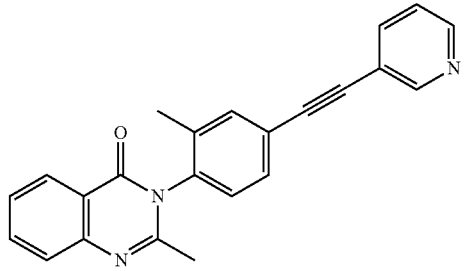

29e

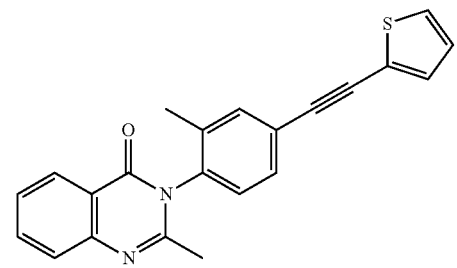

and iv. reacting a 2-methyl-3-(2-methyl-4-(phenylethynyl)phenyl)quinazolin-4(3H)-one of formula 29-a, 29-b, 29-c, 29-d, or 29-e as obtained in step (iii) with an aldehyde of formula 30a, 30b, 30c, 30d, 30e, 30f, 30g, 30h, 30i, 30j, 30k, 30l, 30m, 30n, 31a, 31b, 32a, 32b, 33a, or 33b in acetic acid and heating said reaction under reflux conditions for 8-10 hours to obtain a compound of formula A 30a

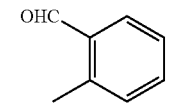

30b

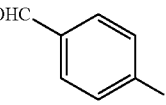

30c

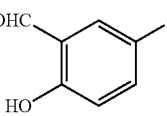

30d

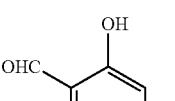

30e

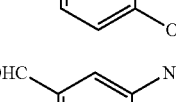

30f

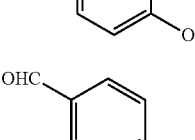

-continued
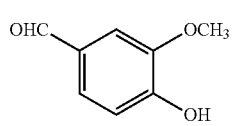 30g
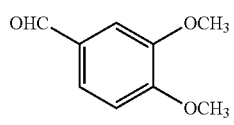 30h
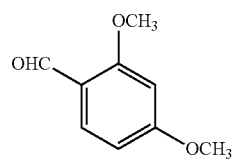 30i
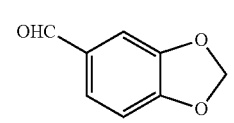 30j
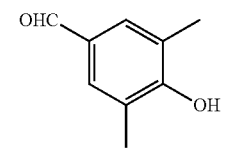 30k
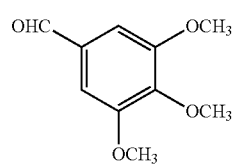 30l
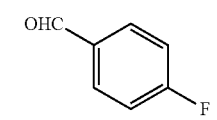 30m
-continued
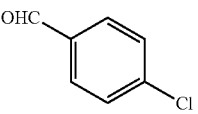 30n
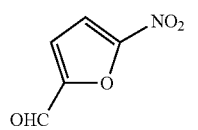 31a
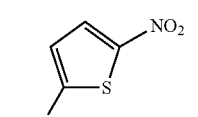 31b
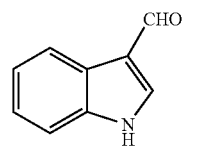 32a
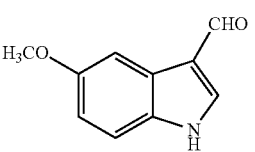 32b
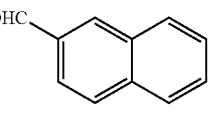 33a
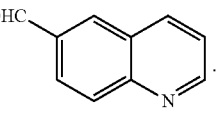 33b
* * * * *